(12) United States Patent
Jackson et al.

(10) Patent No.: US 11,160,709 B2
(45) Date of Patent: Nov. 2, 2021

(54) SURGICAL TABLE WITH MOVEMENT CAPABILITIES OF LOWER BODY SUPPORT STRUCTURES

(71) Applicant: Warsaw Orthopedic, Inc., Warsaw, IN (US)

(72) Inventors: Roger P. Jackson, Prairie Village, KS (US); Lawrence E. Guerra, Overland Park, KS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 79 days.

(21) Appl. No.: 16/310,370

(22) PCT Filed: Jun. 14, 2017

(86) PCT No.: PCT/US2017/037516
§ 371 (c)(1),
(2) Date: Dec. 14, 2018

(87) PCT Pub. No.: WO2017/218683
PCT Pub. Date: Dec. 21, 2017

(65) Prior Publication Data
US 2019/0209409 A1    Jul. 11, 2019

Related U.S. Application Data

(60) Provisional application No. 62/516,939, filed on Jun. 8, 2017, provisional application No. 62/492,561, filed on (Continued)

(51) Int. Cl.
*A61G 13/04* (2006.01)
*A61B 6/04* (2006.01)
(Continued)

(52) U.S. Cl.
CPC ............ *A61G 13/04* (2013.01); *A61B 6/0407* (2013.01); *A61G 7/05* (2013.01); *A61G 13/122* (2013.01);
(Continued)

(58) Field of Classification Search
CPC ........ A61G 13/04; A61G 13/122; A61G 7/05; A61G 13/1235; A61G 2210/50;
(Continued)

(56) References Cited

U.S. PATENT DOCUMENTS 5,131,106 A * 7/1992 Jackson .......................... 5/613
6,046,525 A    6/2000 Hoffman
(Continued)

FOREIGN PATENT DOCUMENTS

WO    2017218683 A1    12/2017

OTHER PUBLICATIONS

International Search Report and Written Opinion of the International Searching Authority, PCT/US2017/037516, dated Oct. 6, 2017.
(Continued)

*Primary Examiner* — Myles A Throop
(74) *Attorney, Agent, or Firm* — Sorell, Lenna & Schmidt, LLP

(57) ABSTRACT

A surgical table for prone and lateral positioning of a patient, where the table includes a base and a patient support structure. The base may include a head and a foot end support structure. The patient support structure may include an upper body support structure cantilevered off of the head end support structure at a first end and a lower body support structure cantilevered off of the foot end support structure at a second end. The upper body support structure may include a chest pad. The lower body support structure may include
(Continued)

a lower body translation and rotation structure and at least one pelvic pad supported thereon.

11 Claims, 47 Drawing Sheets

Related U.S. Application Data on May 1, 2017, provisional application No. 62/425,539, filed on Nov. 22, 2016, provisional application No. 62/361,967, filed on Jul. 13, 2016, provisional application No. 62/350,065, filed on Jun. 14, 2016.

(51) Int. Cl.
*A61G 7/05* (2006.01)
*A61G 13/12* (2006.01)
*A61G 13/08* (2006.01)

(52) U.S. Cl.
CPC .......... *A61G 13/1235* (2013.01); *A61G 13/08* (2013.01); *A61G 13/123* (2013.01); *A61G 2200/322* (2013.01); *A61G 2200/325* (2013.01); *A61G 2210/50* (2013.01)

(58) Field of Classification Search
CPC ........ A61G 2200/322; A61G 2200/325; A61G 13/123; A61G 13/08; A61B 6/0407
See application file for complete search history.

(56) References Cited

U.S. PATENT DOCUMENTS

| | | | | |
|---|---|---|---|---|
| 6,076,525 | A | 6/2000 | Hoffman | |
| 7,152,261 | B2 | 12/2006 | Jackson et al. | |
| 7,343,635 | B2 | 3/2008 | Jackson et al. | |
| 7,565,708 | B2 | 7/2009 | Jackson et al. | |
| 7,739,762 | B2 | 6/2010 | Jackson et al. | |
| 8,060,960 | B2 * | 11/2011 | Jackson | A61B 6/0407 5/611 |
| 8,140,402 | B1 | 3/2012 | Mesaros | |
| 8,584,281 | B2 * | 11/2013 | Diel | A61G 13/0036 5/608 |
| 8,677,529 | B2 | 3/2014 | Jackson et al. | |
| 8,707,484 | B2 | 4/2014 | Jackson et al. | |
| 8,719,979 | B2 | 5/2014 | Jackson et al. | |
| 8,826,474 | B2 | 9/2014 | Jackson et al. | |
| 8,826,475 | B2 | 9/2014 | Jackson et al. | |
| 8,839,471 | B2 | 9/2014 | Jackson et al. | |
| 8,844,077 | B2 | 9/2014 | Jackson et al. | |
| 8,844,735 | B1 | 9/2014 | Jackson et al. | |
| 8,856,986 | B2 | 10/2014 | Jackson et al. | |
| 8,938,826 | B2 | 1/2015 | Jackson et al. | |
| 8,941,312 | B2 | 1/2015 | Jackson et al. | |
| 8,978,180 | B2 | 3/2015 | Jackson et al. | |
| 9,180,062 | B2 | 11/2015 | Jackson et al. | |
| 9,186,291 | B2 | 11/2015 | Jackson et al. | |
| 9,198,817 | B2 | 12/2015 | Jackson et al. | |
| 9,205,013 | B2 | 12/2015 | Jackson et al. | |
| 9,211,223 | B2 | 12/2015 | Jackson et al. | |
| 9,226,865 | B2 | 1/2016 | Jackson et al. | |
| 9,264,900 | B2 | 2/2016 | Jackson et al. | |
| 9,265,679 | B2 * | 2/2016 | Jackson | A61G 13/123 |
| 9,289,342 | B2 | 3/2016 | Jackson et al. | |
| 9,295,433 | B2 | 3/2016 | Jackson et al. | |
| 9,301,897 | B2 * | 4/2016 | Jackson | A61G 13/0036 |
| 9,308,145 | B2 * | 4/2016 | Jackson | A61G 7/001 |
| 9,339,430 | B2 * | 5/2016 | Jackson | A61G 13/04 |
| 9,358,170 | B2 | 6/2016 | Jackson et al. | |
| 9,364,380 | B2 | 6/2016 | Jackson et al. | |
| 9,402,775 | B2 | 8/2016 | Jackson et al. | |
| 9,414,982 | B2 | 8/2016 | Jackson et al. | |
| 9,456,945 | B2 | 10/2016 | Jackson et al. | |
| 9,468,576 | B2 | 10/2016 | Jackson et al. | |
| 9,504,622 | B2 * | 11/2016 | Jackson | A61G 13/0054 |
| 9,510,987 | B2 | 12/2016 | Jackson et al. | |
| 9,549,863 | B2 | 1/2017 | Jackson et al. | |
| 9,561,145 | B2 | 2/2017 | Jackson et al. | |
| 9,572,734 | B2 | 2/2017 | Jackson et al. | |
| 9,610,206 | B2 | 4/2017 | Jackson et al. | |
| 9,622,928 | B2 | 4/2017 | Jackson et al. | |
| 9,629,766 | B2 | 4/2017 | Jackson et al. | |
| 9,636,266 | B2 | 5/2017 | Jackson et al. | |
| 9,642,760 | B2 * | 5/2017 | Jackson | A61G 13/104 |
| 9,687,399 | B2 | 5/2017 | Jackson et al. | |
| 9,744,087 | B2 | 8/2017 | Jackson et al. | |
| 9,744,089 | B2 | 8/2017 | Jackson et al. | |
| 9,757,300 | B2 | 9/2017 | Jackson et al. | |
| 2006/0123546 | A1 * | 6/2006 | Horton | A61G 13/0054 5/613 |
| 2010/0192300 | A1 | 8/2010 | Tannoury et al. | |
| 2011/0107517 | A1 | 5/2011 | Lamb et al. | |
| 2012/0022651 | A1 | 1/2012 | Akyuz et al. | |
| 2012/0246829 | A1 | 10/2012 | Jackson et al. | |
| 2013/0219623 | A1 * | 8/2013 | Jackson | A61G 13/0036 5/613 |
| 2013/0312181 | A1 * | 11/2013 | Jackson | A61G 7/001 5/601 |
| 2014/0020181 | A1 * | 1/2014 | Jackson | A61G 13/1295 5/607 |
| 2014/0109316 | A1 | 4/2014 | Jackson et al. | |
| 2015/0040319 | A1 * | 2/2015 | Doak | A61G 13/04 5/620 |
| 2015/0150743 | A1 | 6/2015 | Jackson et al. | |
| 2016/0193099 | A1 * | 7/2016 | Drake | A61G 13/125 5/624 |
| 2016/0317373 | A1 | 11/2016 | Jackson et al. | |
| 2016/0346148 | A1 | 12/2016 | Jackson et al. | |
| 2016/0346149 | A1 | 12/2016 | Jackson et al. | |
| 2017/0071809 | A1 | 3/2017 | Jackson et al. | |
| 2017/0151115 | A1 | 6/2017 | Jackson et al. | |
| 2017/0181908 | A1 | 6/2017 | Jackson et al. | |
| 2017/0189254 | A1 | 7/2017 | Jackson et al. | |
| 2017/0202523 | A1 | 7/2017 | Jackson et al. | |
| 2017/0209325 | A1 | 7/2017 | Jackson et al. | |
| 2017/0319411 | A1 | 11/2017 | Jackson et al. | |
| 2017/0333276 | A1 | 11/2017 | Jackson et al. | |
| 2017/0348171 | A1 | 12/2017 | Jackson et al. | |

OTHER PUBLICATIONS

International Search Report of the International Searching Authority (US) dated Oct. 6, 2017 of International PCT Application No. PCT/US2017/037516 filed on Jun. 14, 2017.

* cited by examiner

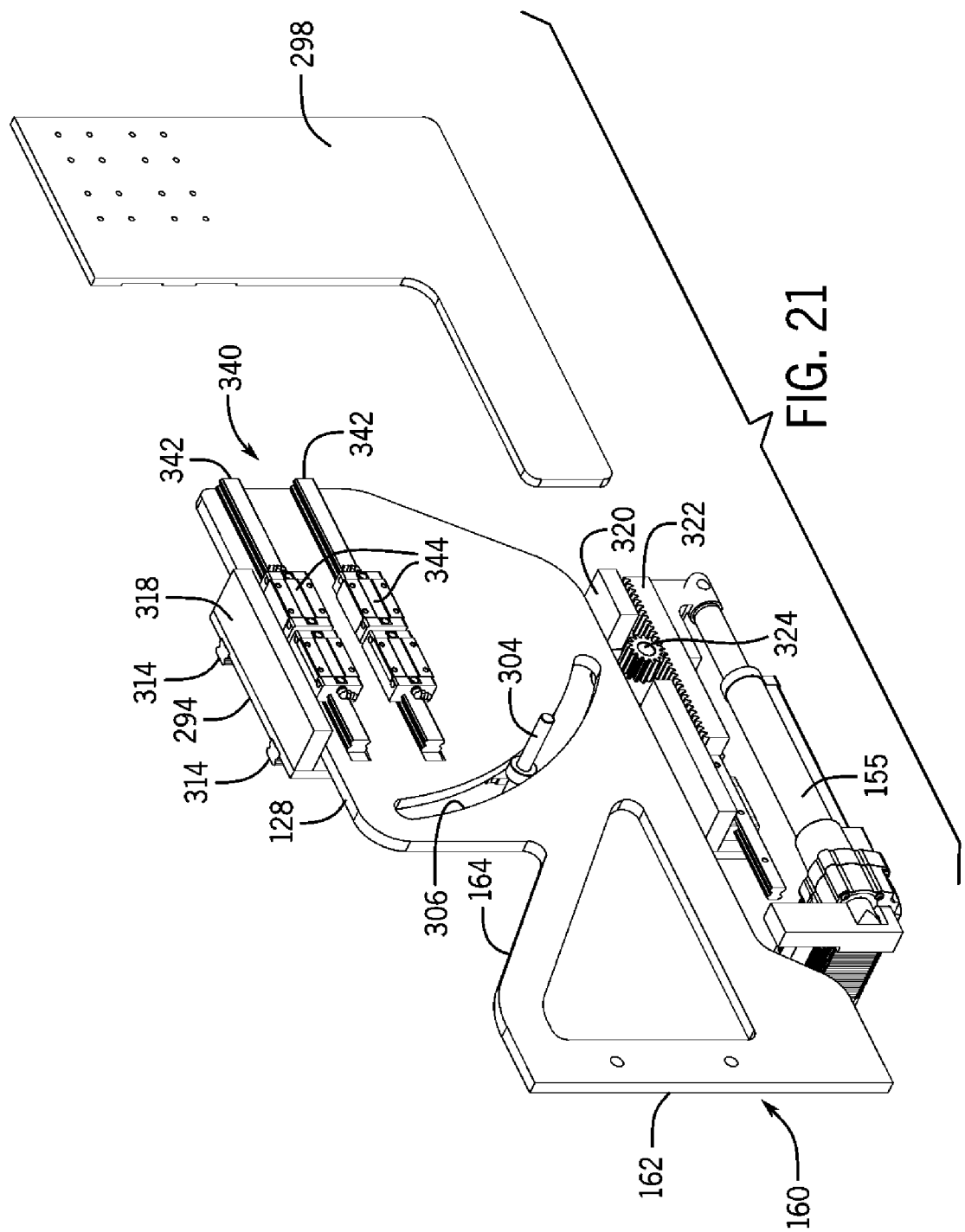

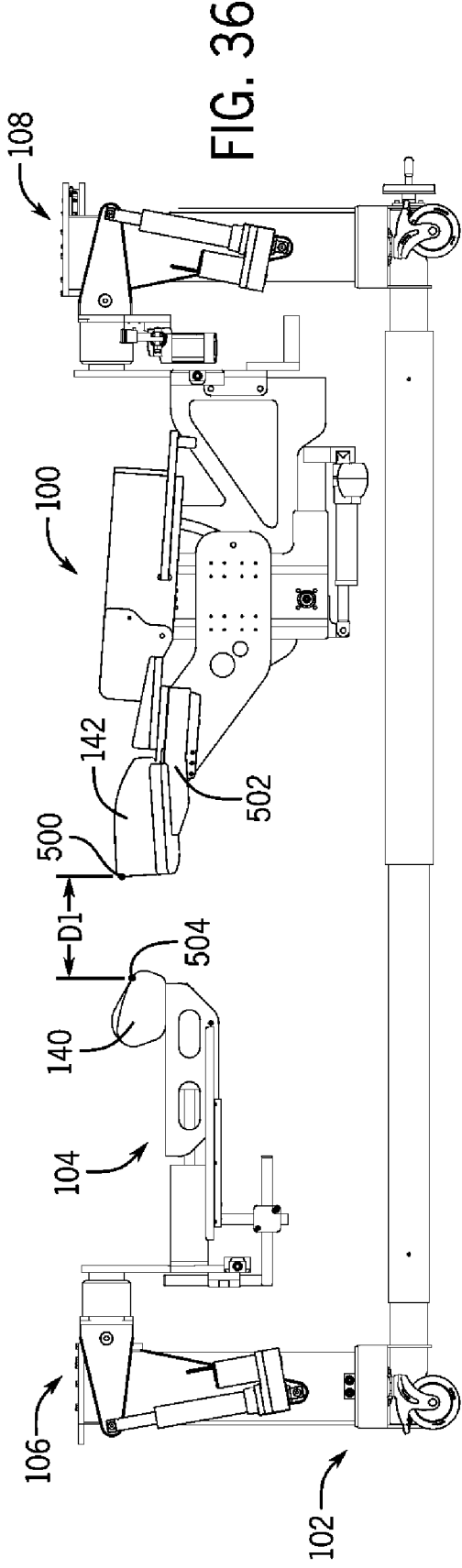
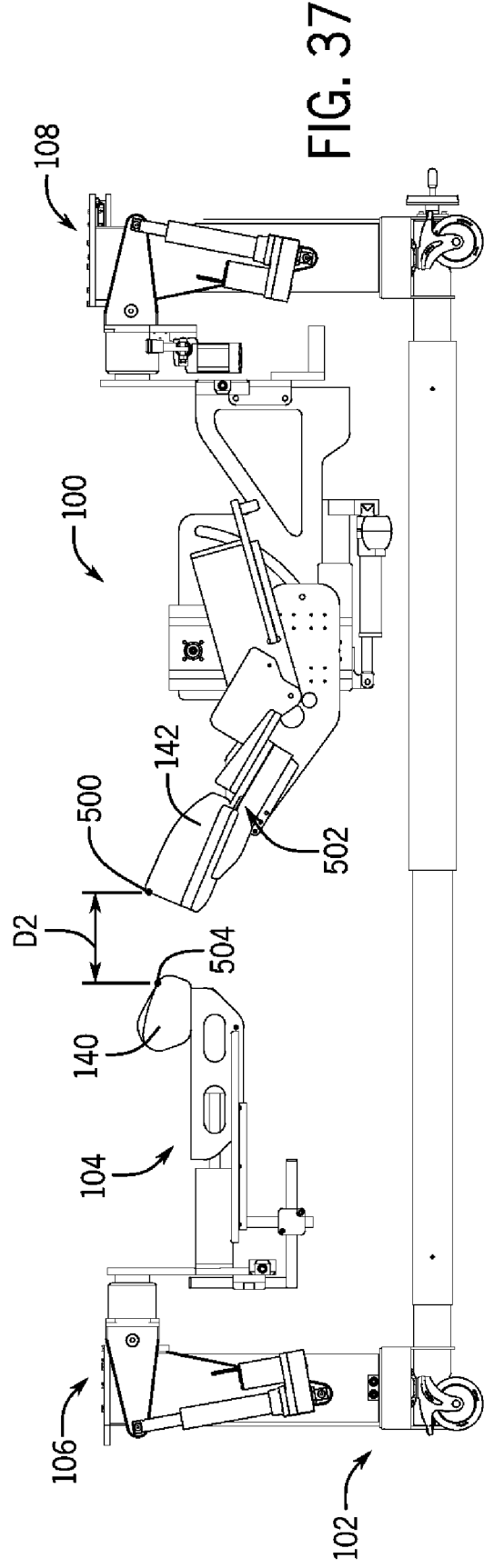

SURGICAL TABLE WITH MOVEMENT CAPABILITIES OF LOWER BODY SUPPORT STRUCTURES

CROSS-REFERENCE TO RELATED APPLICATIONS

The present application is related to and incorporates by reference the following Patent Applications in their entireties: U.S. patent application Ser. No. 14/793,359, filed Jul. 7, 2015; U.S. patent application Ser. No. 14/793,050, filed Jul. 7, 2015; U.S. patent application Ser. No. 14/792,280, filed Jul. 6, 2015; and, U.S. patent application Ser. No. 14/792,216, filed Jul. 6, 2015.

The present application claims priority under 35 U.S.C. § 119 to the following U.S. Provisional Patent Applications, which are incorporated by reference in their entireties: U.S. Provisional Patent Application No. 62/516,939, filed Jun. 8, 2017, entitled "PRONE AND LATERAL SURGICAL TABLE"; U.S. Provisional Patent Application No. 62/491,561, filed Apr. 28, 2017, entitled "PRONE AND LATERAL SURGICAL TABLE"; U.S. Provisional Patent Application No. 62/425,539, filed Nov. 22, 2016, entitled "PRONE AND LATERAL SURGICAL TABLE"; U.S. Provisional Patent Application No. 62/361,967, filed Jul. 13, 2016, entitled "PRONE AND LATERAL SURGICAL TABLE"; and U.S. Provisional Patent Application No. 62/350,065, filed Jun. 14, 2016, entitled "PRONE AND LATERAL SURGICAL TABLE".

TECHNICAL FIELD

Aspects of the present disclosure involve a surgical table for prone and lateral positioning.

BACKGROUND

Current surgical approaches often utilize surgical procedures involving multiple access angles to a surgical site. For example, some surgical procedures move the patient to different positions (e.g. Trendelenburg, reverse Trendelenburg, supine, prone, lateral, lateral-decubitus, flexion, extension, etc.) throughout the procedure to change and access the surgical site from different angles. Further, some surgical procedures, such as spinal surgery, may involve access through more than one surgical site and with the spine in different positions. Because these sites may not be in the same plane or anatomical location, the patient needs to be moved intra-operatively to and supported in different positions during the procedure. However, many conventional tables providing adjustable patient positioning do not allow easy access to the surgical sites with unrestricted imaging capabilities. Further, many conventional tables have complex and expensive mechanical parts and arrangements that are not radiolucent. Further yet, many conventional table are unable to position a patient in prone and lateral positions without having to re-position the patient and re-prep and drape the surgical sites.

With these thoughts in mind, among others, aspects of the prone and lateral surgical table, disclosed herein, were conceived and developed.

SUMMARY

Aspects of the present disclosure may involve a surgical table for prone and lateral positioning of a patient. In certain instances, the table may include a base and a patient support structure. The base may be supported on the floor and may include a head end support structure, a foot end support structure opposite the head end support structure, a rail connecting the head and foot end support structures, and a longitudinal axis extending between the head and foot end support structures. The patient support structure may include an upper body support structure cantilevered off of the head end support structure at a first end and a lower body support structure cantilevered off of the foot end support structure at a second end. The upper body support structure may include a third end opposite the first end. The lower body support structure may include a fourth end opposite the second end. The third end and the fourth end may be non-joined with each other. The upper body support structure may include a chest pad, and the lower body support structure may include a lower body translation and rotation structure and at least one pelvic pad supported thereon. The at least one pelvic pad may be rotationally coupled with the lower body translation and rotation structure via a shaft configured to rotate about a rotation axis that is generally perpendicular to the longitudinal axis, wherein, when the patient support structure changes from a neutral position to a flexed position, the lower body translation and rotation structure is configured to translate the at least one pelvic pad towards the chest pad, and rotate the at least one pelvic pad about the rotation axis.

In certain instances, the lower body support structure may include an actuator configured to cause the lower body translation and rotation structure to translate and rotate the at least one pelvic pad via actuation of the actuator.

In certain instances, the third and fourth ends define a gap therebetween.

In certain instances, the lower body translation and rotation structure may be slidably supported on a central support structure that is coupled to the foot end support structure.

In certain instances, the lower body translation and rotation structure may include an inner translation structure and an outer translation structure, the inner translation structure slidably coupled with the central support structure, the outer translation structure slidably coupled with the inner translation structure, the inner and outer translation structures configured to facilitate horizontal and vertical translation of the at least one pelvic pad supported thereon relative to the central support structure.

In certain instances, a combined rotation and translation of the at least one pelvic pad defines a virtual pivot axis about which the at least one pelvic pad is configured to rotate. The virtual pivot axis may be configured to maintain a substantially constant height when the patient support structure changes from a neutral position to a flexed position.

In certain instances, the virtual pivot axis may extend transverse through a distal portion of the at least one pelvic pad.

In certain instances, the surgical table may further include a pair of non-hinged outer frame members supported at a head end by the head end support structure and supported at a foot end by the foot end support structure, the pair of non-hinged outer frame members may include a right lateral side member and a left lateral side member.

In certain instances, when the patient support structure changes from the neutral position to an extended position, the lower body translation and rotation structure is configured to translate the at least one pelvic pad away the chest pad, and rotate the at least one pelvic pad about the rotation axis.

Aspects of the present disclosure may involve surgical table for prone and lateral positioning of a patient. In certain instances, the table may include a base and a patient support structure. The base may be supported on the floor and may include a head end support structure, a foot end support structure opposite the head end support structure, and a rail connecting the head and foot end support structures. The patient support structure may include an upper body support structure cantilevered off of the head end support structure at a first end, and a lower body support structure cantilevered off of the foot end support structure at a second end. The upper body support structure may include a third end opposite the first end. The lower body support structure may include a fourth end opposite the second end. The third end and the fourth end may be non-joined with each other. The lower body support structure may include a right and left lower body support sections and a central support structure, where each of the right and left lower body support sections may include a pelvic support member supporting a pelvic pad, a thigh support member, and a lower leg support assembly. The central support structure may be coupled to the foot end support structure. The right and left lower body support sections may be coupled to the central support structure and configured to move relative to the central support structure when moving the patient between flexed and extended positions.

In certain instances, the patient support structure may include a pair of non-hinged outer frame members supported at a head end by the head end support structure and supported at a foot end by the foot end support structure, the pair of non-hinged outer frame members may include a right lateral side member and a left lateral side member.

In certain instances, the pelvic support member of the left lower body support section is pivotally coupled with a portion of the left lower body support section so as to pivot laterally outward from the portion of the left lower body support section to provide access to a left anterior portion of the patient.

In certain instances, the pelvic support member of the right lower body support section may be pivotally coupled with a portion of the right lower body support section so as to pivot laterally outward from the portion of the right lower body support section to provide access to a right anterior portion of the patient.

In certain instances, the lower body support structure may include an inner translation structure slidingly coupled to the central support structure and an outer translation structure slidingly coupled to the inner translation structure, wherein the inner and outer translation structures are configured to facilitate vertical and horizontal translation of the right and left lower body support sections relative to the central support structure.

Aspects of the present disclosure may involve a method of positioning a patient having arms, a lower back, a flank, a lower abdomen, a spine, and a pelvis on a patient support structure of a surgical table and inserting a spinal implant into the patient's spine. The method may include positioning the patient prone on the patient support structure having a chest pad and a pair of pelvic pads. The method may further include stabilizing the patient's arms on a pair of arm supports, rolling the patient into a lateral decubitus position so that one pelvic pad is oriented upwardly over the other pelvic pad, moving the upwardly oriented pelvic pad away from the patient's pelvis, sterilely prepping and draping at least the patient's flank and making an incision therein so as to proceed to insert the implant into the patient's spine, closing the incision and moving the pelvic pad back into position with respect to the patient's pelvis after a sterile cover is placed over the pelvic pad, and rolling the patient back into a prone position.

In certain instances, the pelvic pad is moved away from the patient's pelvis and is positioned against the patient's lower abdomen.

In certain instances, the pelvic pad is rotatable away from and towards the patient's pelvis.

In certain instances, the implant is inserted into a disc space of the patient's spine.

In certain instances, when the patient is in the prone position, an incision is made on the patient's lower back.

In certain instances, the surgical table may include: a base supported on the floor and may include a head end support structure and a foot end support structure opposite the head end support structure; and the patient support structure may include an lower body support structure and a rigid, open, and non-hinged outer frame supported at a head end by the head end support structure and supported at a foot end by the foot end support structure, the outer frame may include a right lateral side member and a left lateral side member, each extending between the head and foot end support structures, the lower body support structure may include a right and a left lower body support section and a central member, each right and left lower body support section may include an upper leg member coupled with a lower leg member.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE FIGURES

The description will be more fully understood with reference to the following figures, which are presented as various embodiments of the disclosure and should not be construed as a complete recitation of the scope of the disclosure, wherein:

FIG. 21 depicts a perspective view of a right portion of the central support structure for prone and lateral positioning with the right side translation panel moved from the central support structure, in one embodiment.

FIG. 36 depicts a side view of a surgical table with a patient support structure in a neutral position.

FIG. 37 depicts a side view of a surgical table with a patient support structure in a flexed position.

DETAILED DESCRIPTION

Various embodiments of the disclosure are discussed in detail below. While specific implementations are discussed, it should be understood that this is done for illustration purposes only. A person skilled in the relevant art will understand that other components and configurations can be used without parting from the spirit and scope of the disclosure.

It should be understood at the outset that although illustrative implementations of one or more embodiments are illustrated below, the disclosed device can be implemented using any number of techniques. The disclosure should in no way be limited to the illustrative implementations, drawings, and techniques illustrated herein, but can be modified within the scope of the appended claims along with their full scope of equivalents.

Unless otherwise specified, any use of any form of the terms "connect," "engage," "couple," "attach," or any other term describing an interaction between elements is not meant to limit the interaction to direct interaction between the elements and can also include indirect interaction between the elements described. In the following discussion and in the claims, the terms "including" and "comprising" are used in an open-ended fashion, and thus should be interpreted to mean "including, but not limited to . . . ". The various characteristics described in more detail below, will be readily apparent to those skilled in the art with the aid of the present disclosure upon reading the following detailed description, and by referring to the accompanying drawings.

The present disclosure generally relates to a surgical table for prone and lateral positioning. More particular, the surgical table is configured for positioning a patient laterally while also being able to position a patient prone during the same procedure without manually moving the patient and re-prepping and re-draping. In the prone position, the patient may be positioned neutrally, in flexion, or in extension. In an embodiment, the table can be configured for prone-only patient positioning, as further disclosed herein. Additionally, the patient may be positioned in other positions that do not involve flexing of the patient's midsection, such as Trendelenburg and reverse Trendelenburg. FIGS. 1-25 depict various views of a surgical table for prone and lateral positioning. FIGS. 26-33 depict a method of performing a surgery involving positioning a patient prone, moving the patient into a lateral position, moving a portion of the patient support structure away from the surgical site, inserting an implant, repositioning the portion of the patient support structure back to the surgical site, and positioning the patient back into a prone position.

Figure 1:
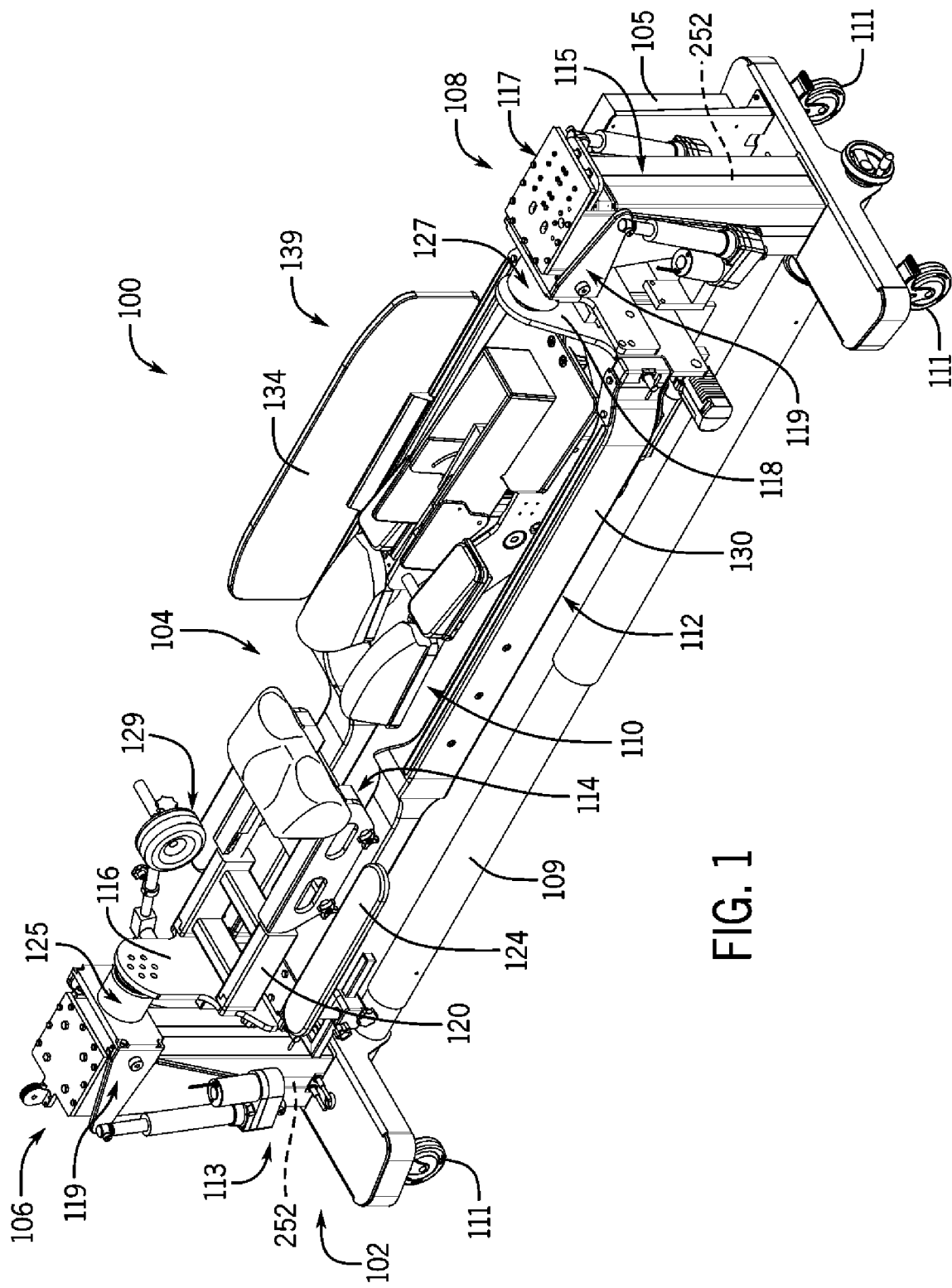
FIG. 1 depicts a perspective view of a surgical table for prone and lateral positioning, in one embodiment.
Figure 2A:
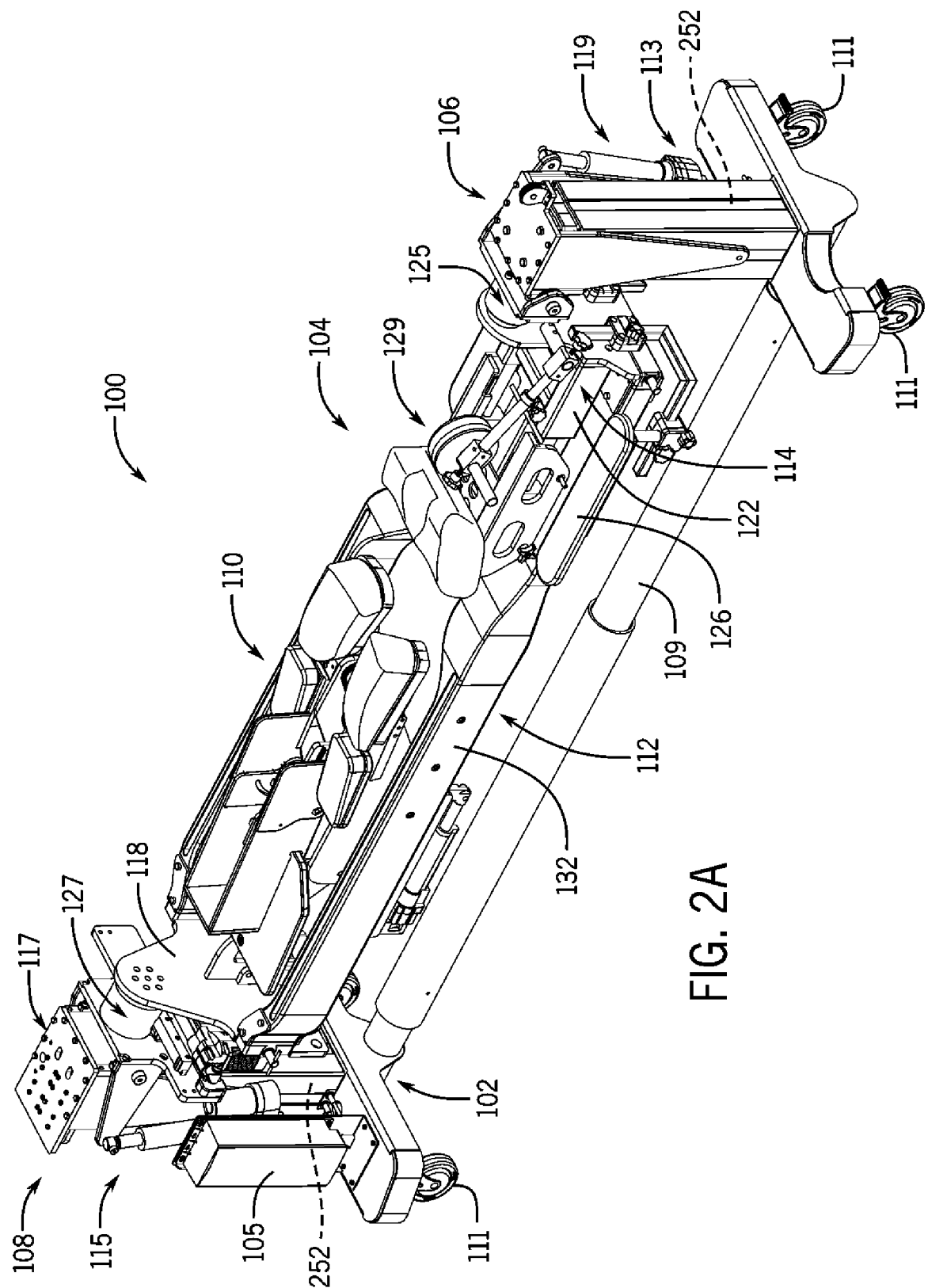
FIG. 2A depicts a perspective view of a surgical table for prone and lateral positioning, in one embodiment.
Figure 2B:
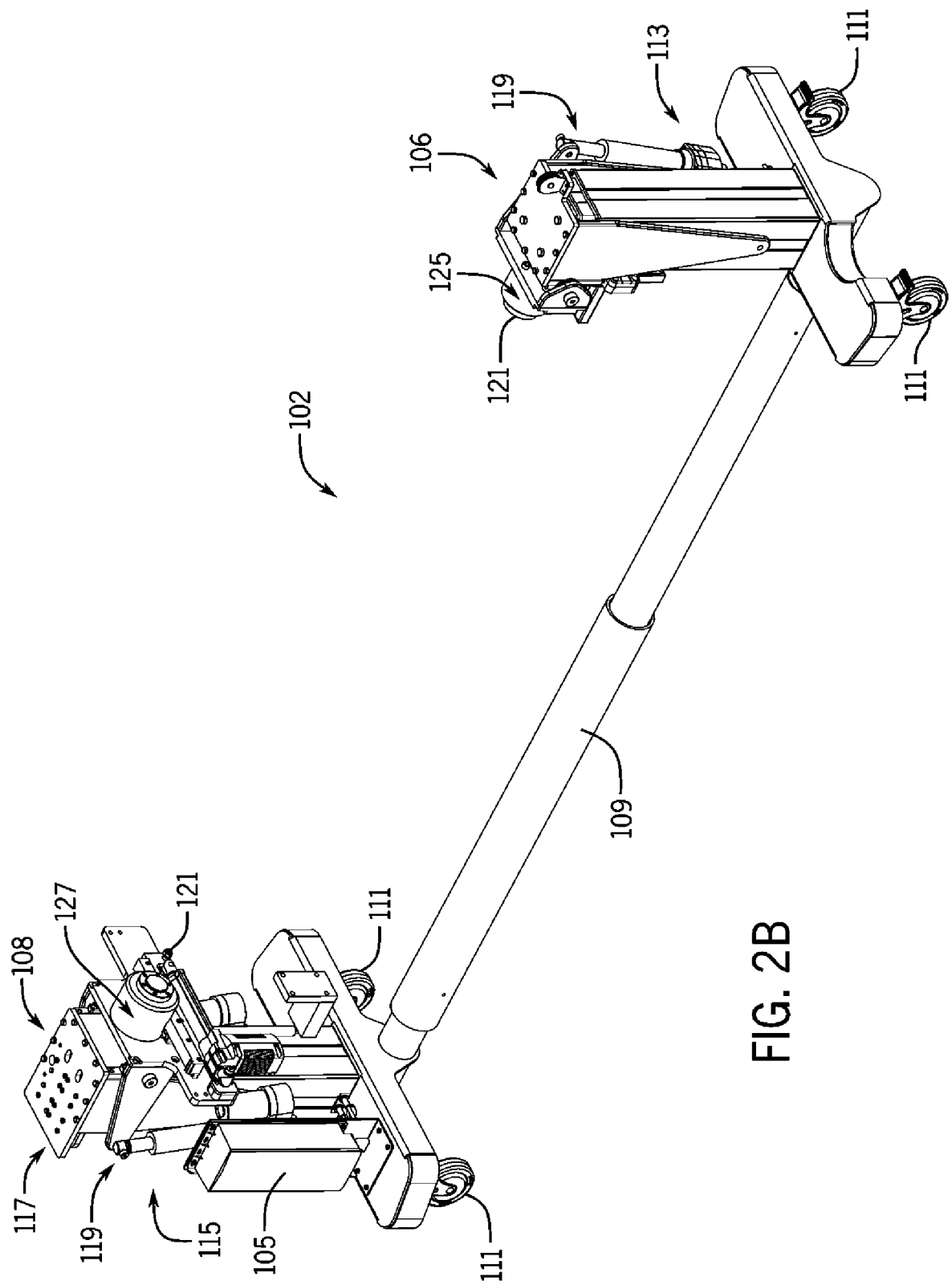
FIG. 2B depicts a perspective view of the base of the surgical table, in one embodiment.

As seen in FIGS. 1, 2A, and 2B the surgical table 100 includes a base 102 having opposed end support structures, including a head end support structure 106 and a foot end support structure 108, coupled together near the floor with a rail 109. In certain instances, the rail 109 is telescoping so the end support structures 106, 108 can be moved closer together as the rail 109 telescopes. For example, the rail 109 may telescope such that the end support structures 106, 108 move closer together when the table 100 is stored, as will be discussed in reference to FIG. 34. This may provide convenient transportation and storage of the surgical table 100 and, in particular, the base 102.

The dual column base 102 is supported on the floor by wheels 111 and supports a patient support structure 104, as seen in FIGS. 1 and 2A, extending between the head end support structure 106 and the foot end support structure 108. Each end support structure 106, 108 may include an upwardly extending system or support column 113, 115 that is elongatable. The upwardly extending systems 113, 115 may provide for vertical height adjustment of the end support structures 106, 108. In some embodiments, there may be actuators 252 (e.g., linear actuators) within the upwardly extending elongatable systems 113, 115 that cause cylinders to telescope upwards and downwards. In an embodiment, there may be three nested cylinders that telescope upwardly when actuated by the actuators 252. In such a way, each of the head and foot end support structures 106, 108 are capable of independent height adjustment via actuation of the actuators 252 in the upwardly extending systems 113, 115, respectively.

As seen in FIGS. 1, 2A, and 2B, the end support structures 106, 108 may further include a pivoting assembly 119. In some embodiments, pivoting assemblies 119 pivot in response to upward and downward movement of the end support structures 106, 108 and are located at or near the top of the end support structures 106, 108. It is foreseen that the pivoting assembly 119, one or both, may be actively or passively driven to actively maintain coaxial alignment of a roll axis of the patient support structure 104, as taught in the related applications. For example, active or powered angulation that maintains coaxial alignment of the roll axis may be accomplished, for example, with a base 102 as described in U.S. patent application Ser. No. 14/793,050, filed Jul. 7, 2015, the entirety of which is incorporated by reference herein. Even with passive pivot assemblies, as seen in U.S. Provisional Patent Application No. 62/516,939, filed Jun. 8, 2017, entitled "PRONE AND LATERAL SURGICAL TABLE", which is incorporated by reference herein in its entirety, a roll axis extending through shafts of opposed rotation assemblies 125, 127 is maintained in coaxial alignment because of the rigid outer frame 112, which will be discussed subsequently.

As seen in FIGS. 1, 2A, and 2B, the head end support structure 106 may include a head end rotation assembly 127 and the foot end support structure 108 may include a foot end rotation assembly 125. In some embodiments, the foot end rotation assembly 125 and the head end rotation assembly 127 may be active or passive. As seen in FIG. 2B, the rotation assemblies 125, 127 includes a shaft 121 configured to be coupled with a plate of the pivoting assembly 119 and a foot end plate 118 and/or a head end plate 116 that extends downward towards the floor. The foot end plate 118 and head end plate 116 are coupled to a foot end or head end of an outer frame 112 of the patient support structure 104. In an embodiment, one or both of the rotation assemblies 125, 127 may be active and include an actuator 107 that causes rotation of the shaft 121 via linear movement of the actuator 107. In a non-limiting example, the actuator 107 may be a linear actuator. Rotational movement of the shaft 121 causes the patient support structure 104 to rotate. It is noted that one or both of the head end and foot end may include actuators 107 to facilitate rotation of the shafts 121 of the rotation assemblies 125, 127. In certain embodiments, the rotation assembly 125, 127 may rotate the patient support 104 about ninety degrees. In certain embodiments, the rotation assembly 125, 127 may rotate the patient support eighty to ninety degrees in a first direction from neutral and ten to twenty degrees in a second direction from neutral. It is foreseen that the surgical table 100 may rotate other degrees, such as those taught in the related applications incorporated by reference. In another embodiment, the shaft 119 of the rotation assembly 125, 127 can be passive. In various examples, one rotation assembly may be active and one rotation assembly may be passive or both rotation assemblies may be actively driven. In one example, as seen in FIGS. 1, 2A and 2B, the foot end rotation assembly 127 may be active and the head end rotation assembly 125 may be passive.

In an embodiment, as seen in FIG. 2A, a controller 105 is coupled to the foot end support structure 108. The controller 105 may be linked with a pendant (not shown) for controlling certain operations of the surgical table 100 such as raising and lowering the upwardly extending systems 113, 115. In an embodiment, the controller 105 is linked with a computer and display (not shown) for controlling and/or operating the surgical table 100.

In an embodiment, as seen in FIG. 2B, which is a perspective view of the base 102, the foot end support structure 108 may include a foot end rotation assembly 127, a foot end angulation or pivot assembly 119, and the foot end upwardly extending system 115. Opposite the foot end support structure 108, the head end support structure 106 may include a head end rotation assembly 125, a head end angulation or pivot assembly 119, and the head end upwardly extending system 113.

Figure 2C:
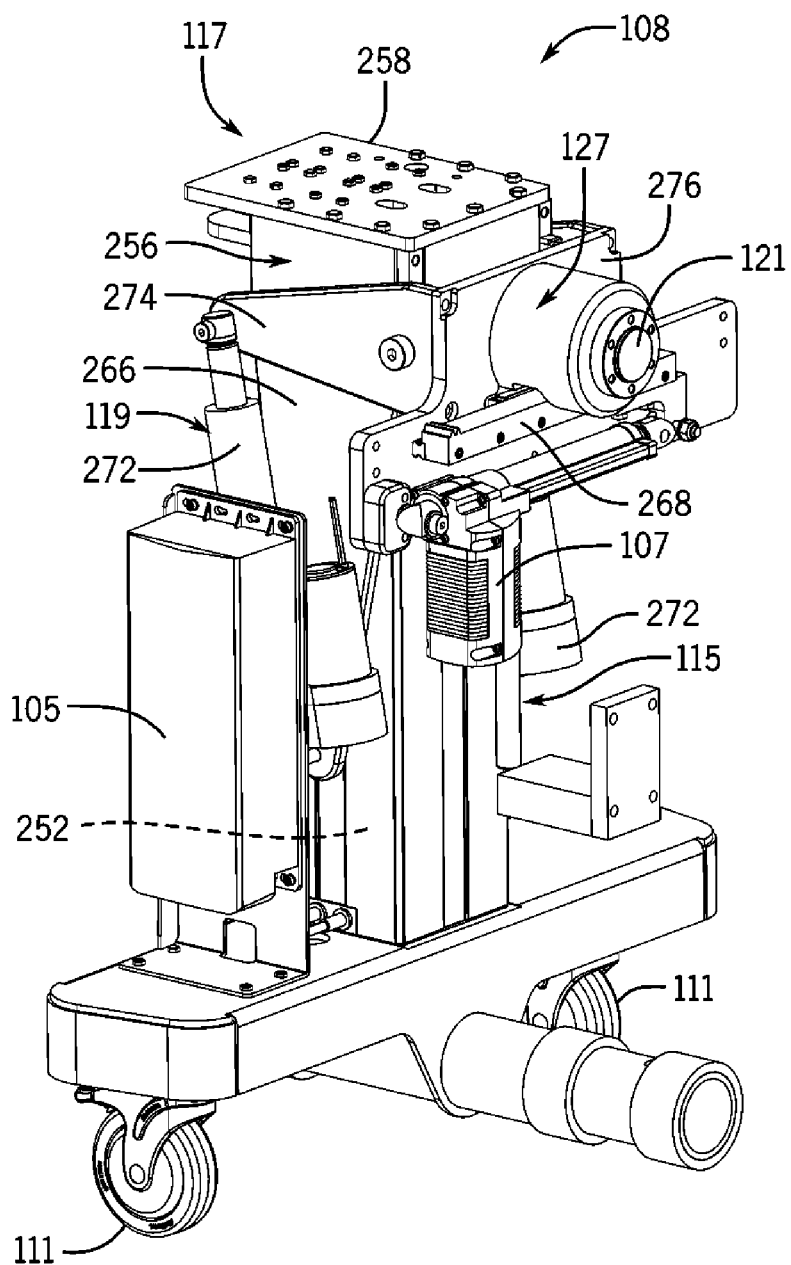
FIG. 2C depicts a perspective view of a foot end support structure of the surgical table, in one embodiment.
Figure 2D:
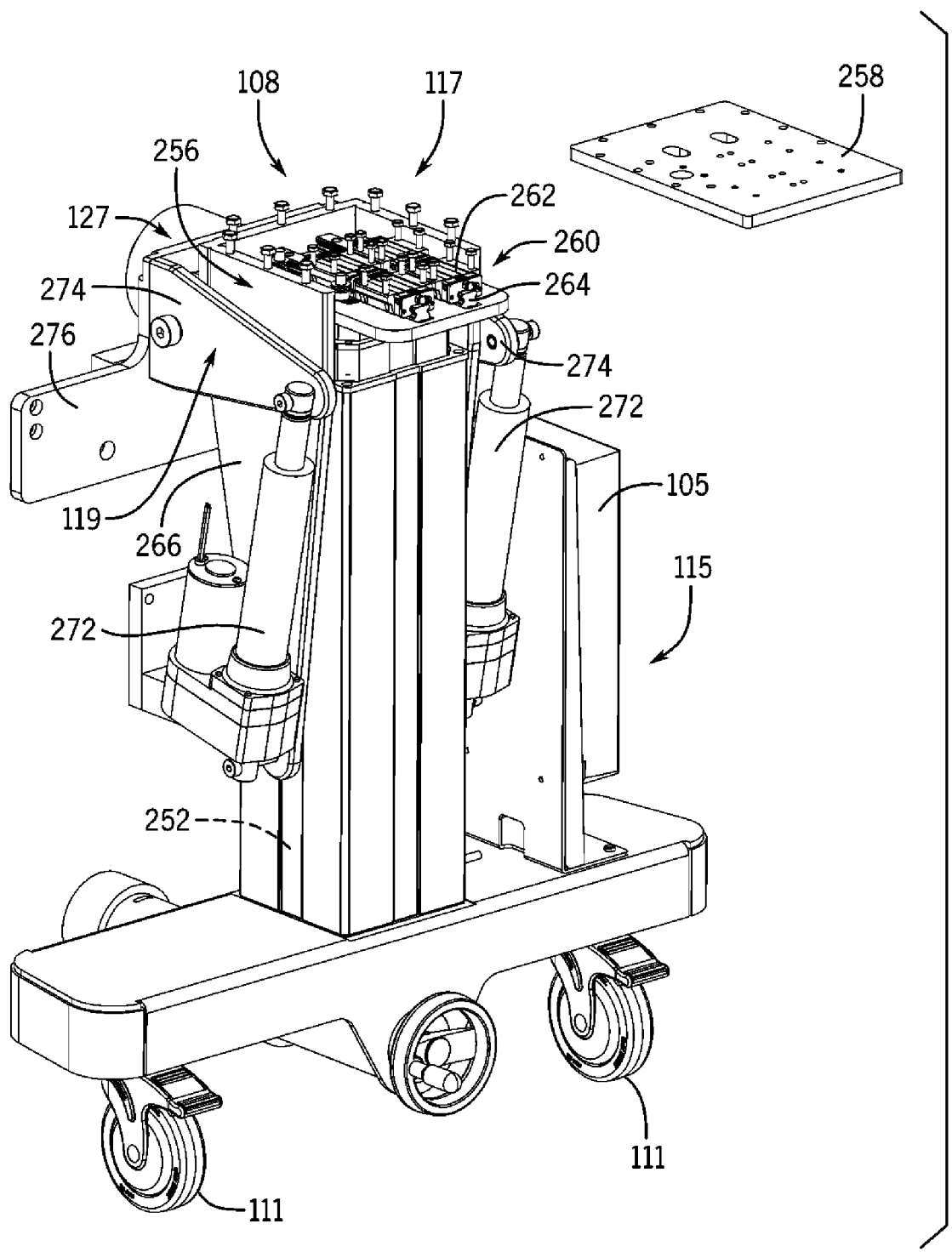
FIG. 2D depicts a perspective view of the foot end support structure with a top plate moved so as to view the lateral translation assembly, in one embodiment.

As seen in FIGS. 2C and 2D, which are perspective views of the foot end support structure 108 from the front and back, respectively, a longitudinal translation compensation assembly 117 may be included to provide for longitudinal adjustment to the table 100 when the patient support structure 104 changes its angular position at the angulation assemblies 125, 127. As seen in FIGS. 2C and 2D, the longitudinal translation compensation assembly 117 may include a housing 256 including a top plate 258, and a slide assembly 260. As seen in FIG. 2C, the top plate 258 is secured to carriages 262 of the slide assembly 260, and the carriages 262 may slide on rails 264 of the slide assembly 260, which are secured to a plate on the inner most cylinder of the upwardly extending system 115. The top plate 258 may also be secured to a U-shaped structure 266 of the housing 256 that wraps around the sides and front of the upwardly extending system 115. The pivot assembly 119 is pivotally coupled to the U-shaped structure 266 of the housing 256 such that the pivot assembly 119 and the rotation assembly 127 are slidable relative to the upwardly extending system 115.

In this way, as the patient support structure 104 changes its angular orientation (i.e., by the head and foot end upwardly extending systems 113, 115 being at different elevations relative to each other), the housing 256 may passively translate via the sliding assembly 260 along a longitudinal axis that is generally parallel with the rail 109.

In one embodiment, the longitudinal translation compensation assembly 117 is only on top of the foot end support structure 108. In one embodiment, the longitudinal translation compensation assembly 117 is on both the top of the foot end support structure 108 and the head end support structure 106. In one embodiment, the longitudinal translation compensation assembly 117 is only on the head end support structure 106.

As discussed previously, the rotation assembly 127 may include a shaft 121 that is rotationally coupled to a linear actuator 107. As seen in FIG. 2C, extension and retraction of an arm of the linear actuator 107 causes linear movement of a rail 268 that engages with the shaft 121 of the rotation assembly 127. Thus, as arm of the linear actuator 107 extends and retracts, the arm causes the shaft 121 to rotate, thus, rotating the patient support structure 104 (not shown in FIG. 2C).

Figure 2E:
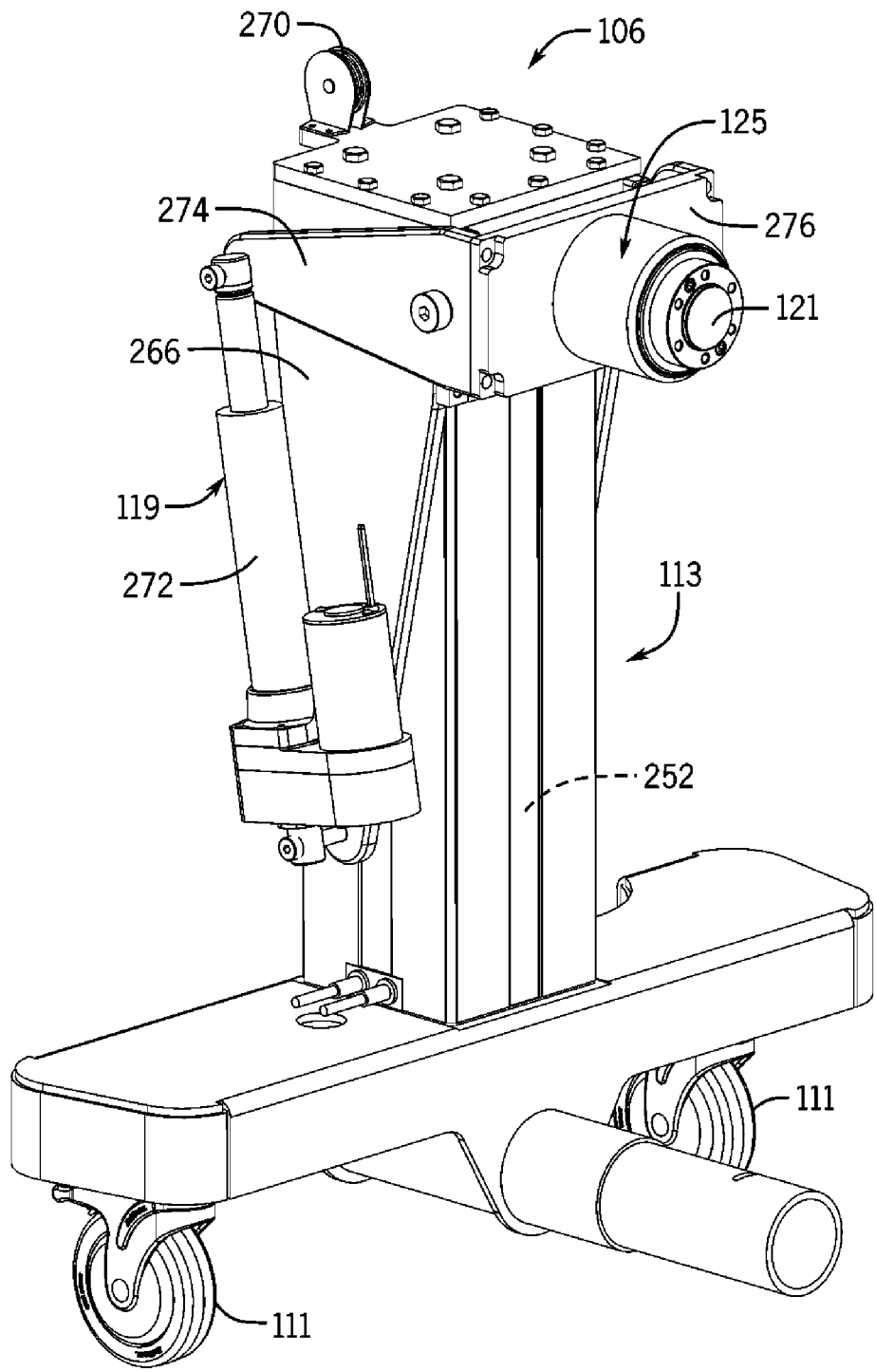
FIG. 2E depicts a perspective view of the head end support structure, in one embodiment.

In an embodiment, as seen in FIG. 2E, which depicts a perspective view of the head end support structure 106, the rotation assembly 125 including the shaft 121 are not actively driven. That is, the shaft 121 rotates passively in response to rotation caused by the rotation assembly 127 at the foot end support structure 108. As seen in FIG. 2E, a pulley 270 of a traction system may be included at the top of the upwardly extending system 113.

Referring to FIGS. 2C and 2D, the pivot assembly 119 on the foot end support structure 108 includes linear actuators 272 that are coupled at a lower end to the U-shaped structure 266 that surrounds the sides and back of the structure 108. Opposite the lower end, an upper end of the linear actuators 272 are coupled to a pivot bracket 274 that is pivotally coupled to a roll plate 276 at a joint. The rotation assembly 127 is coupled to the roll plate 276 such that, as the linear actuators 272 extend and retract, the pivot brackets 274 pivot about their respective joints, and angle the roll plate 276 and the rotation assembly 127, which in turn angles the patient support structure 104 (not shown).

As seen in FIG. 2E, the pivot assembly 119 includes one actuator 272 that is similarly coupled at a lower end to the U-shaped structure 266 that surrounds the sides and back of the structure 106. Opposite the lower end, an upper end of the linear actuator 272 is coupled to a pivot bracket 274 that is pivotally coupled to a roll plate 276 at a joint. The rotation assembly 125 is coupled to the roll plate 276 such that, as the linear actuator 272 extends and retracts, the pivot brackets 274 pivot about their respective joints, and angle the roll plate 276 and the rotation assembly 125, which in turn angles the patient support structure 104 (not shown). While one actuator 272 is shown on the head end support structure 106 and two actuators 272 are shown on the foot end support structure 108, in certain embodiments, a different number of actuators 272 may be included depending on the application of the table 100, the strength of the actuators 272, and other possible factors.

The pivot assemblies 119 at the head and foot end support structures 106, 108, respectively, may be configured to maintain coaxial alignment of a roll axis associated with each of the shafts 121 of the rotation assemblies 125, 127. In this way, the surgical table 100 may operate with or without the outer frame members 130, 132 of the outer frame 112 (the outer frame members 130, 132 may alternatively be referred to as side rails). That is, the outer frame members 130, 132 may be optional features to be used depending on the type of surgical procedure to be performed. For example, in certain instances, a surgeon may need to attach certain structures to the table 100, and, thus, one or both of the outer frame members 130, 132 may be included so as to serve as an attachment point for one or more accessories (e.g., retractor, robotic assembly, side board/lateral support board).

In an embodiment of the table 100 without actuators 272 on the end support structures 106, 108, at least one of the frames 130, 132 of the outer frame 112 may be needed to maintain coaxial alignment of the roll axes of the shafts 121 of the rotation assemblies 125, 127. But, in an embodiment with actuators 272 on one or more of the end support structures 106, 108, the surgical table 100 may function with two, one, or none of the frames 130, 132 of the outer frame 121 since the actuators 272 may hold its respective portion of the patient support structure 104 at a given angle.

In certain instances, the pivot assemblies 119 may alternatively not include actuators and, thus, facilitate passive pivoting via elevation of the end support columns 113, 115, as described in U.S. Provisional Patent Application No. 62/516,939, filed Jun. 8, 2017, entitled "PRONE AND LATERAL SURGICAL TABLE," among other applications incorporated by reference.

As seen in FIGS. 1, 2A, and 3-8, the patient support structure 104 may include a side head support 129 for supporting a side of the patient's head when the patient is positioned in a lateral position. In some embodiments, the side head support 129 can be configured to be coupled with the head end plate 116. In other embodiments, the side head support 129 may be coupled to the patient support structure 104 through a cantilevered or extendable bar 141. The head support 129 may be adjusted on either side of the patient support structure 104 and at any height or angle such that the head support 129 provides support for the patient's head when the patient support 104 is rotated about ninety degrees such that the patient is in the lateral position. The side head support 129 may have a generally circular shape, but it is contemplated that the side head support 129 may have any shape that is capable of supporting the patient's head. Further, the size of the side head support 129 can vary based on the patient's size. In some embodiments, the side head support 129 can include a pad or cushion, as seen for example in the figures.

As seen in FIGS. 1, 2A, and 3-8, the surgical table 100 further includes a patient support structure 104. The patient support structure 104 may include a removable outer frame 112, an upper body support structure 114, a lower body support structure 110, and a removable lateral support board 134 coupled to the outer frame 112. The upper body support structure 114 supports a torso or upper body support assembly and is cantilevered off of the head end plate 116. The upper body support structure 114 does not directly connect with the lower body support structure 110; rather, there is a gap between the two structures 114, 110.

The outer frame 112 may include a left lateral side member 130, and a right lateral side member 132. The right and left lateral side members 130, 132 are spaced apart from each other. The right and left lateral side members 130, 132 are rigid members that extends between the opposed end support structures 106, 108. A head end portion of the right and left lateral side members 130, 132 angles underneath the upper body support structure 114. Foot ends of the right and left lateral side members 130, 132 are coupled to the foot end plate 118, while head ends of the right and left lateral side members 130, 132 are coupled to the head end plate 116.

Figure 8:
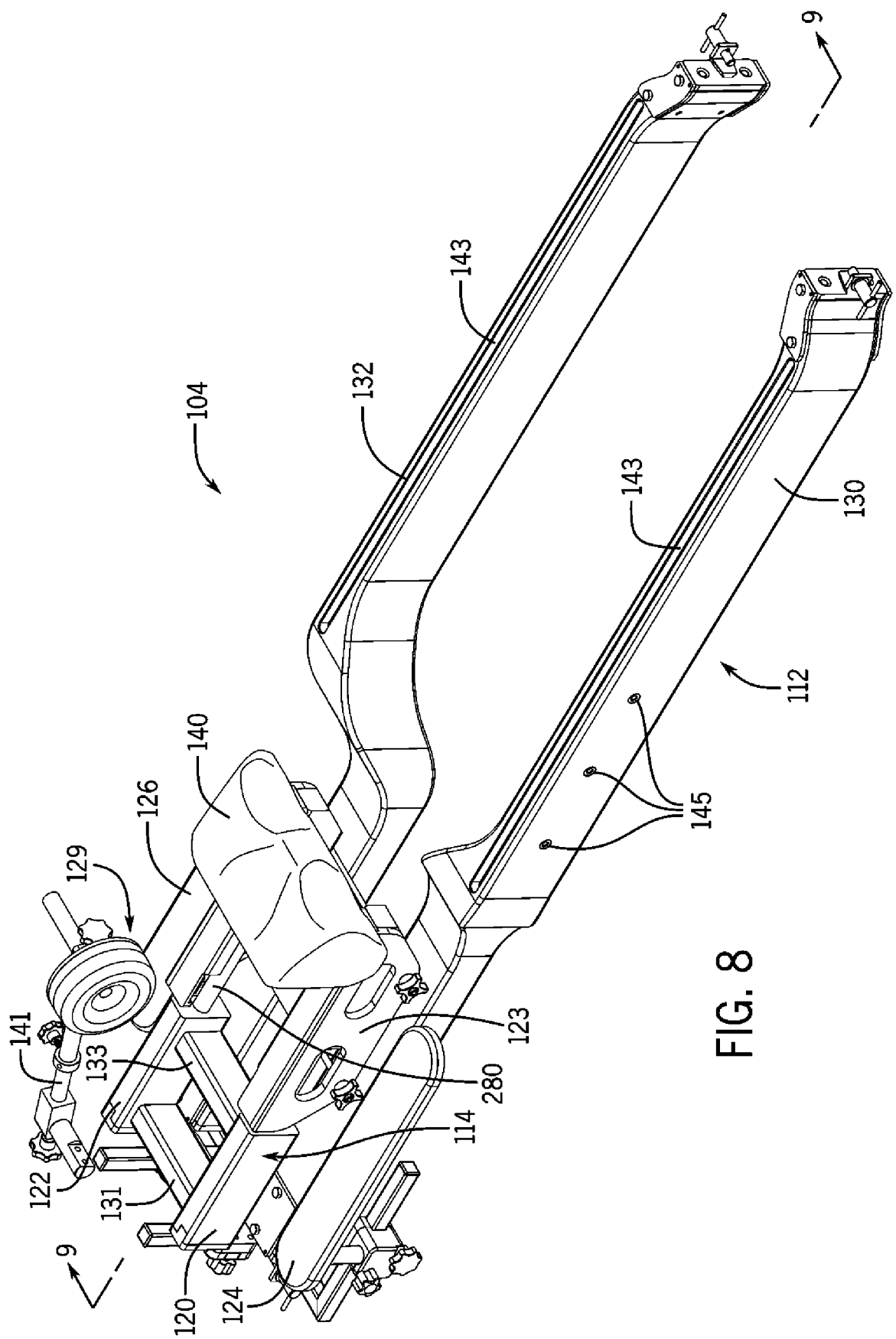
FIG. 8 depicts a perspective view of an outer frame for prone and lateral positioning, in one embodiment.
Figure 9:
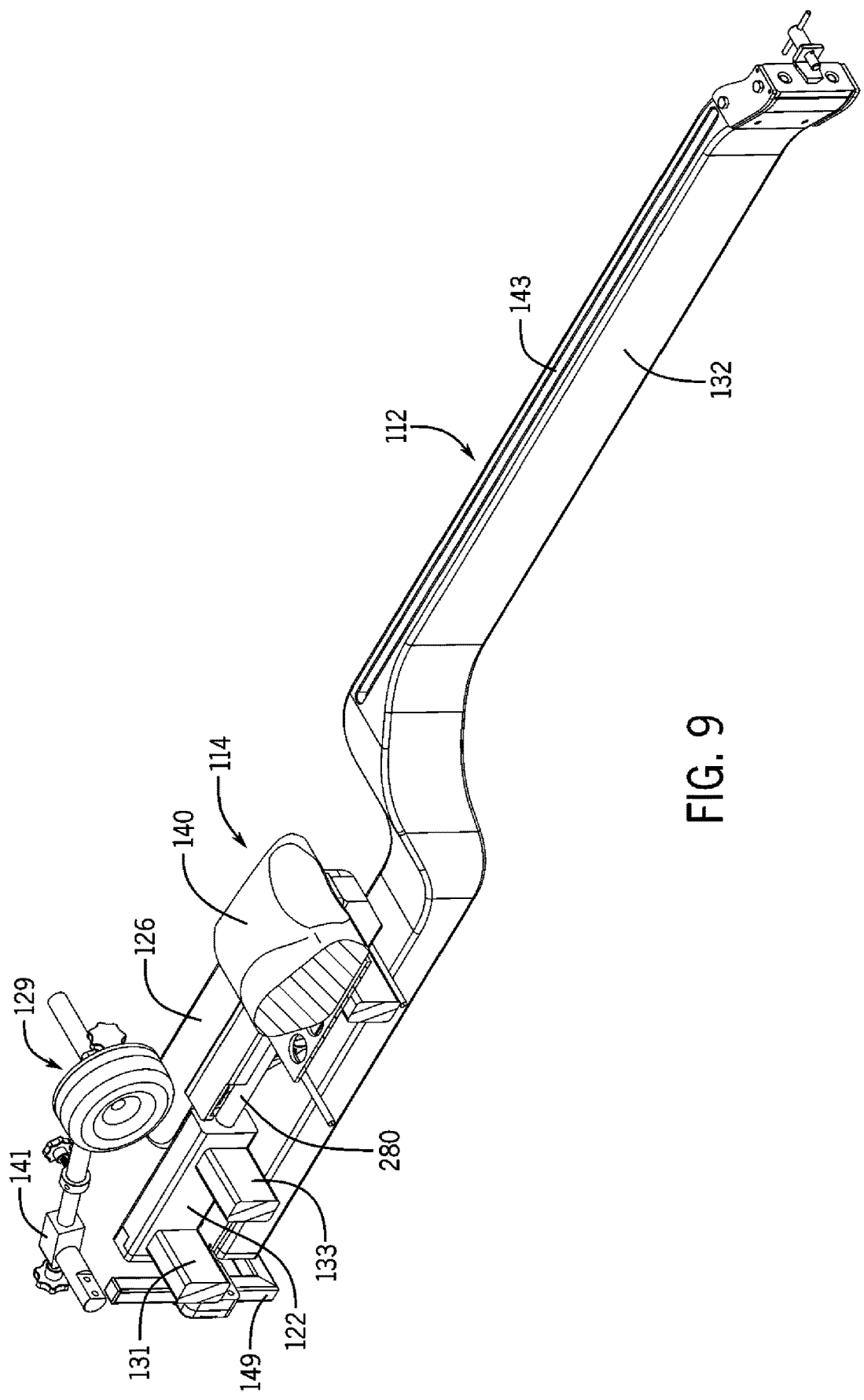
FIG. 9 depicts a perspective view of a right lower body support member and a portion of a right upper body support member, in one embodiment.
Figure 10:
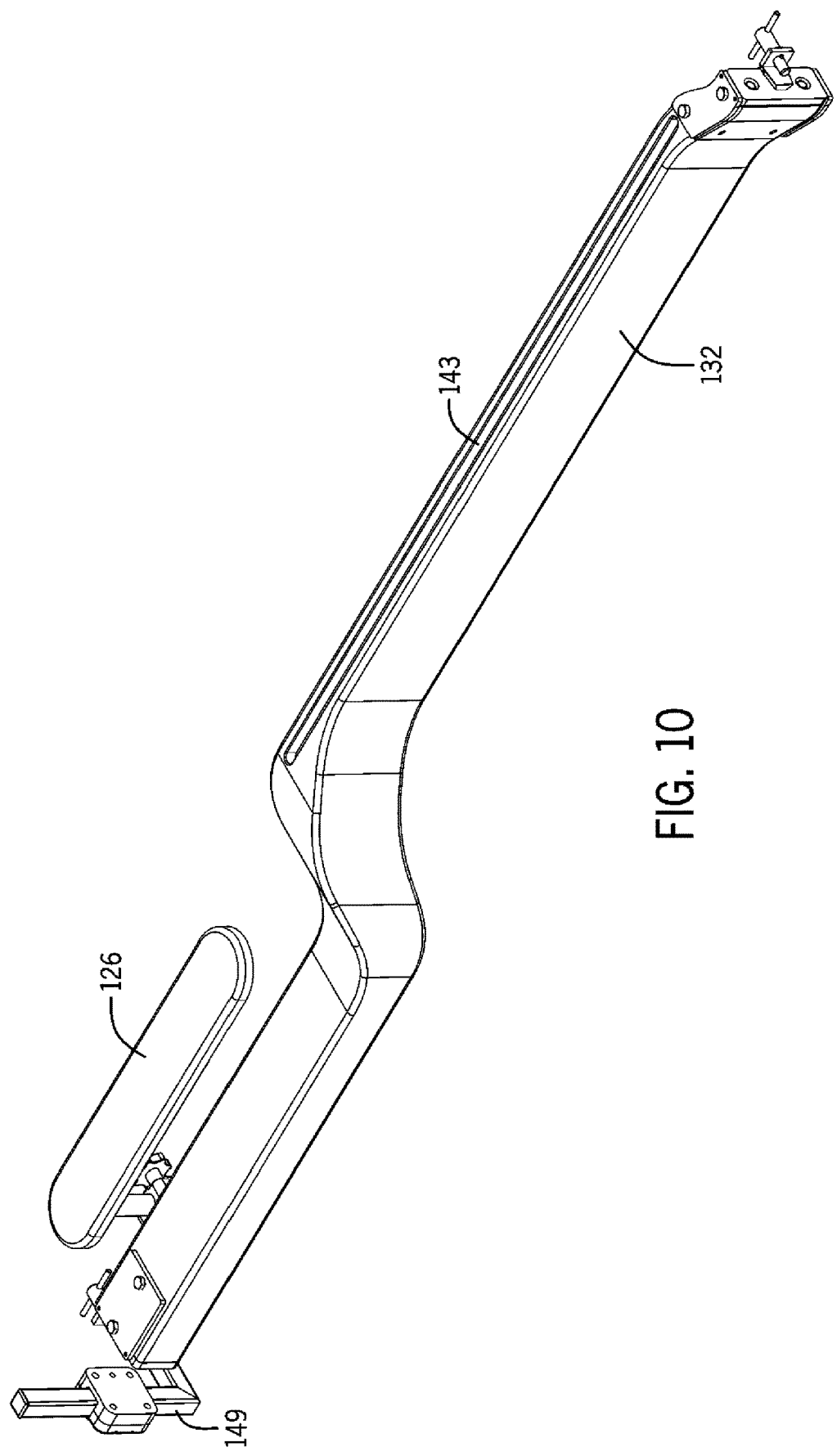
FIG. 10 depicts a perspective view of a right lower body support member, in one embodiment.

As seen in FIGS. 9 and 10, the right and left lateral side members 130, 132 are wider at the foot end than they are at the head end. The right and left lateral side members 130, 132 are rigid in that they do not articulate; rather, they define a stiff structure and can be of hollow or solid construction. The lateral side members 130, 132 may be formed of a single piece of radiolucent material such as by molding. Non-limiting examples of radiolucent materials include carbon fiber and PEEK. The left and right lateral side members 130, 132 are contoured in three planes so as to provide better access for the assisting surgeon in some cases. As seen in FIGS. 8 and 9, the foot end of the right lateral side member 132 is higher than the head end such that the head end of the right lateral side member 132, as seen in FIG. 8, dips below the right upper body support member 122.

As seen in FIGS. 3-5 and 8-10, the left lateral side member 130 and the right lateral side member 132 each may include groove or slot 143 formed in the top and/or bottom surfaces of the members. The lateral side members 130, 132 may further include two or more openings 145 or attachment points on the outer surfaces. The openings 145 or attachment points may be used to secure a support board bracket assembly 139, as further discussed below. The openings 145 or attachment points may also be used to mount an accessory to the outer frame 112. An accessory mounted to the side of the left or right lateral side member 130, 132 provides easy, convenient access to the accessory by the surgeon. In an embodiment, the openings 145 may be configured for receiving an anchoring mechanism to secure the support board bracket assembly 139 or any other accessory to the outer frame 112. The anchoring mechanism may be any mechanism configured to connect with the openings 145 or attachment points, such as a set screw or bolt.

Figure 25:
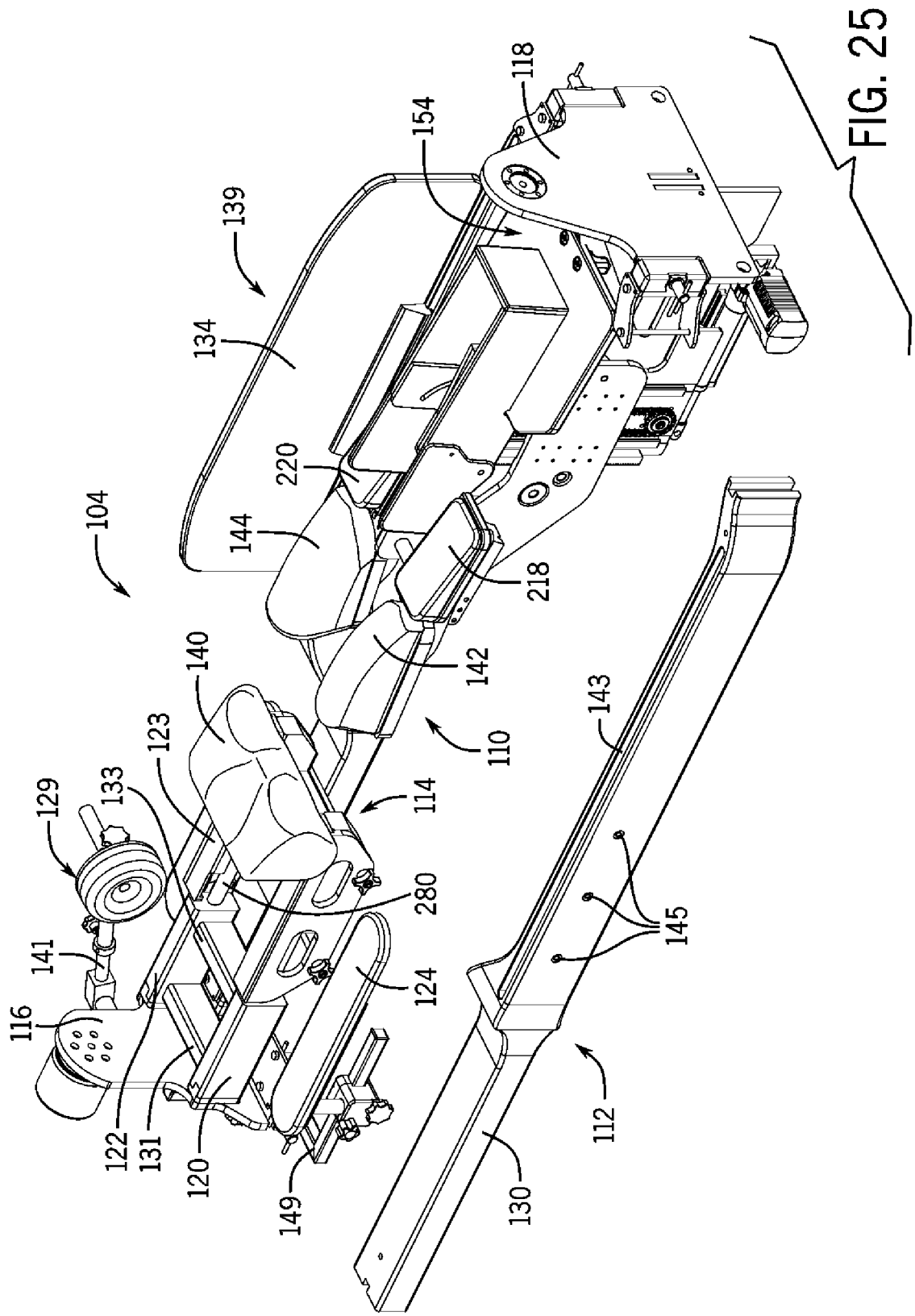
FIG. 25 depicts a perspective view of a patient support structure with a lower body support member removed, in one embodiment.

As seen in FIG. 25, the left lateral side member 130, the right lateral side member 132, or both may be removable from the patient support structure 104. More particularly, the head end of the side members 130, 132 may be removed from the head end plate 116 and the foot end of the members 130, 132 may be removed from the foot end plate 118. The removable lateral side members 130, 132 provide access to the patient's midsection during a lateral surgical approach, among other approaches. One of the right or left lateral side members 130, 134 may be removed from the patient support structure 104 to provide access to an area of the patient (e.g., abdominal) without being encumbered by the patient support structure 104 on a lateral aspect. For example, when the patient is positioned laterally with his or her right side supported against the pad of the right lower body support section 138 and the lateral support board 134, the left lateral side member 130 may be removed. In this example, the surgeon has increased access to the patient's anatomy, in particular, the left flank and left lower abdominal quadrant for anterior surgical approaches, such as to insert interbody spacers or cages. In particular, the foot end of the left lateral side member 130 is decoupled from the foot end plate 118 and the head end of the left lateral side member 130 is decoupled from the head end plate 116. In this way, the foot and head end support structures 106, 108 are still coupled together by the patient support structure 104 via the right lateral side member 132 on the right side of the patient support structure 104. In this arrangement, a surgeon may approach the patient from the left side in an unencumbered fashion to perform a particular surgical procedure. It is noted that either the right or the left lateral side member 130, 132 may be removed to facilitate surgery on either side of the patient. In certain instances, both the right and left lateral side members 130, 132 may be removed. In such an arrangement the upper body support structure 114 and the lower body support structure 110 may still be maintained in an orientation relative to each other as if one or more of the lateral side members 130, 132 were still coupled to the base 102 by way of powered angulation mechanisms (i.e., actuators maintain coaxial alignment of the roll axes) at the head and foot ends of the table 100. In a frame arrangement where a lateral side member of the outer frame 112 is not removed, the surgeon may be impeded from access to the patient's body by the outer frame 112 structure being in the way. Thus, the outer frame 112 with the removable lateral side members 130, 132 may provide improved access to the patient's midsection for lateral approaches, such as to perform surgeries on the spine.

Once one of the lateral support members 130, 132 is removed, an upper leg member 146, 148 on the side of the table 100 where the lateral support member 130, 132 was removed may be pivoted, slid, or removed from its previous position underneath the patient's pelvis, as will be described herein. Moving of the upper leg member 146, 148 and the attached pad 142, 144 increases the access to the surgical site when the patient is in the lateral position, among others.

Figure 3:
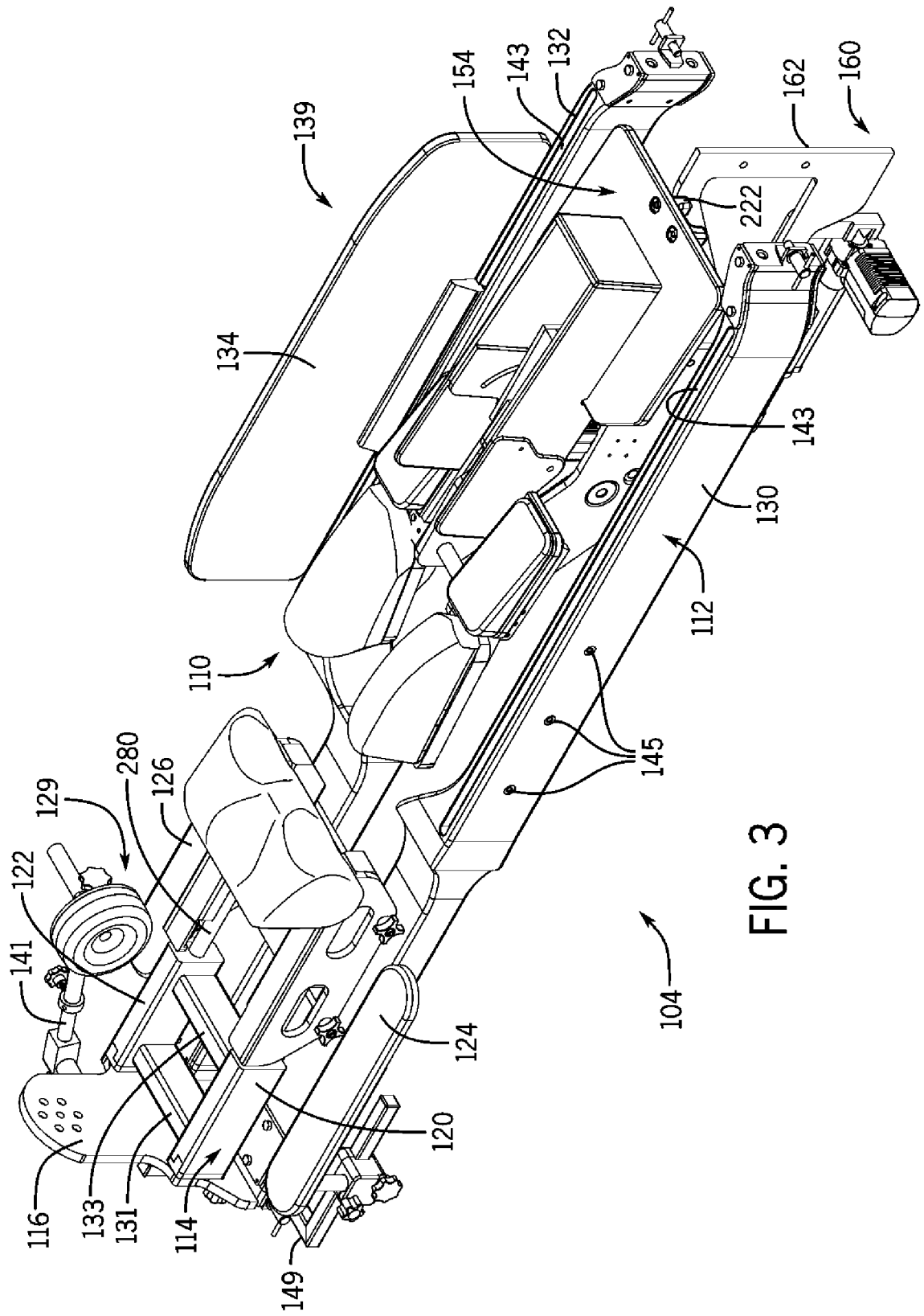
FIG. 3 depicts a perspective view of a portion of a surgical table for prone and lateral positioning, in one embodiment.

As seen in FIGS. 1 and 3, among others, the patient support structure 104 includes a removable and adjustably positioned support board 134 or member to support a patient in a lateral position. The lateral support board 134 may couple with the right or left lower body support members 130, 132 of the outer frame 112 though a groove or slot 143 formed in the top and/or bottom surfaces of the lateral side members 130, 132 and/or the openings 145 on the outer surfaces. In an embodiment, the lateral support board 134 may couple to either the left or right lateral side member 130, 132 through the groove 143 and openings 145 along the lateral side members 130, 132.

Figure 12:
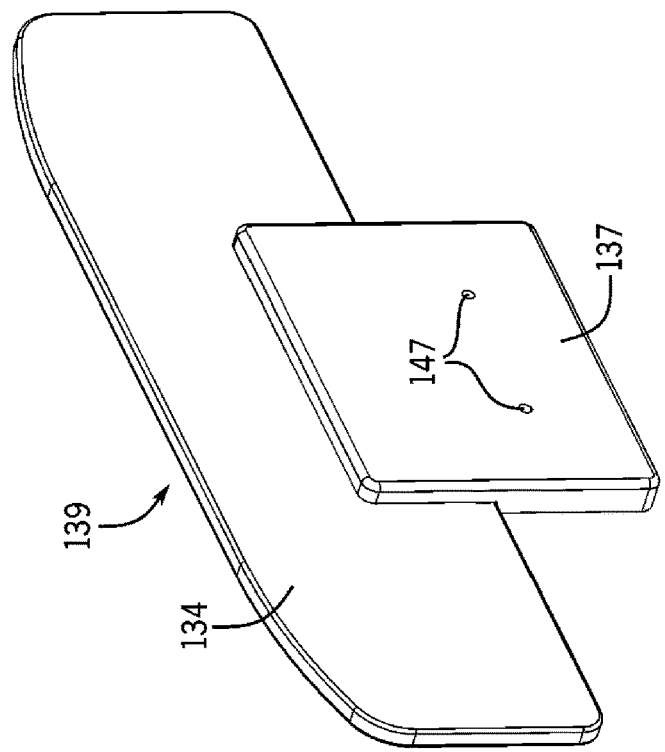
FIG. 12 depicts a back perspective view of a support board bracket assembly, in one embodiment.
Figure 11:
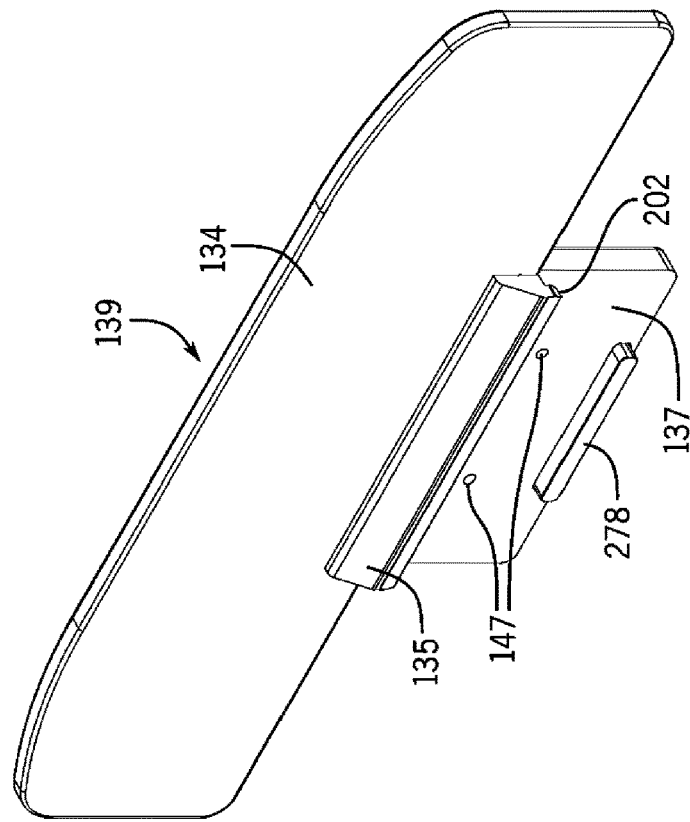
FIG. 11 depicts a front perspective view of a support board bracket assembly, in one embodiment.
Figure 13:
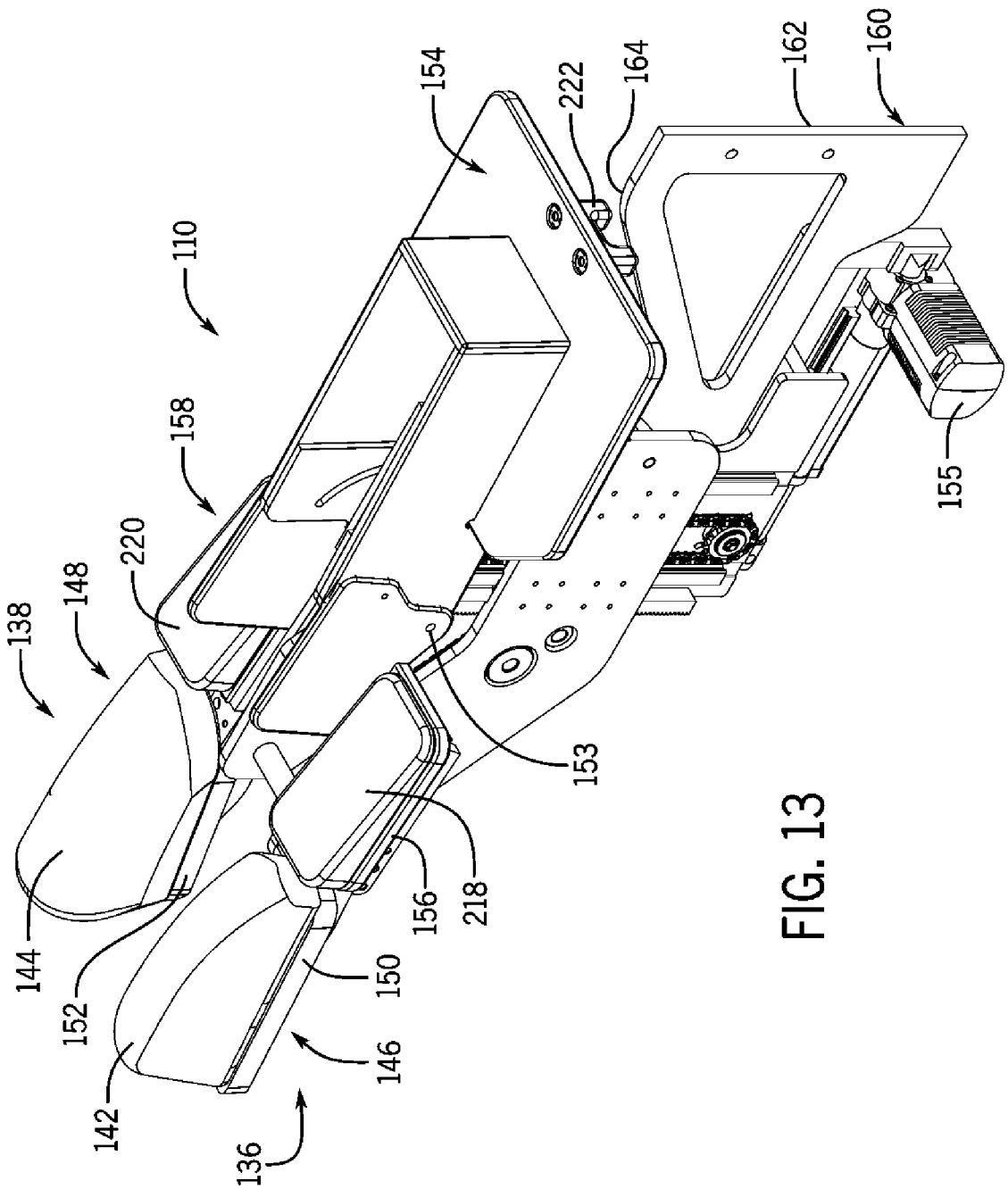
FIG. 13 depicts a perspective view of a lower body support structure for prone and lateral positioning, in one embodiment.
Figure 14:
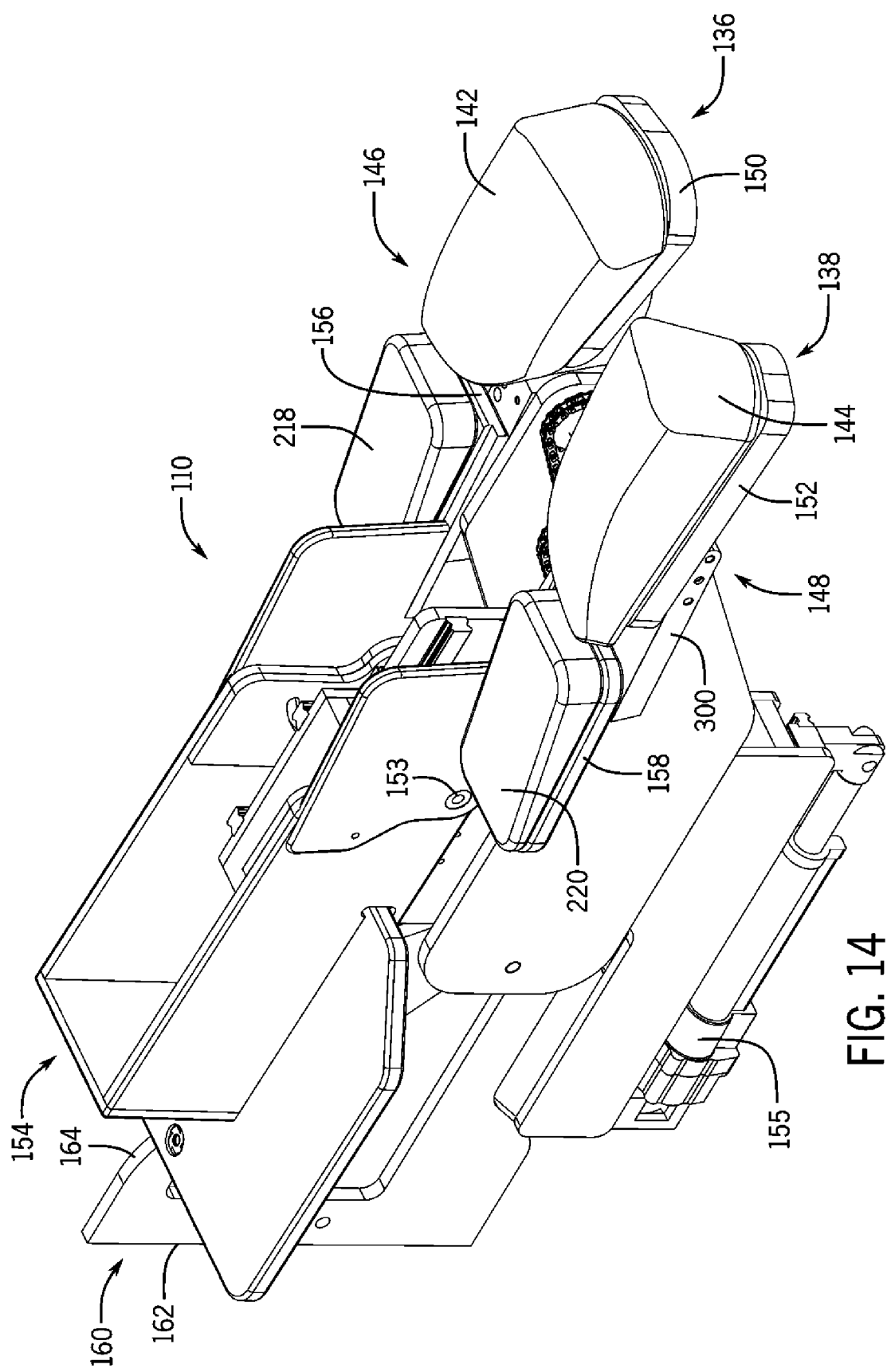
FIG. 14 depicts a perspective view of a lower body support structure for prone and lateral positioning, in one embodiment.

A support board bracket assembly 139, as seen in FIGS. 11 and 12, includes the lateral support board 134, a medial bracket structure 135, and a lateral bracket structure 137. In an embodiment the medial bracket structure 135, the lateral bracket structure 137, or both may be integral with the lateral support board 134. The medial bracket structure 135 includes a protrusion 202 on a bottom side that fits within the groove 143 of the top surface of the right or left lateral side member 130, 132. The medial bracket structure 135 may also include a lateral extending portion that matches and fits within an opening on a bottom side of the support board 134. The support board bracket assembly 139 further includes a lateral bracket structure 137 that engages with the medial bracket structure 135 to sandwich the lateral support board 134 therebetween. As seen in FIGS. 11 and 12, the lateral bracket structure 137 includes at least two openings 147 for receiving an anchoring mechanism, such as a set screw or bolt. The openings 147 are sized and dimensioned to correspond with openings 145 on the outer surface of the lateral side member 130, 132. The lateral bracket structure 137 may also include a lateral protrusion 278 that fits below the bottom edge of the lateral support members 130, 132. An anchoring mechanism, such as a set screw, may be inserted and secured through both the openings 147 of the lateral bracket support structure 137 and the openings 145 of the lateral side member 130, 132.

It is noted that the lateral bracket structure 137 extends vertically along a lateral surface of the support board 134 so as to resist outward or lateral pivoting of the support board 134 relative to the left or right lateral side member 130, 132. In this way, the medial and lateral bracket structures 135, 137 are prevented from twisting relative to the left or right lateral side member 130, 132 via the protrusion 202 of the medial bracket structure 135 fitting within the groove on the top surface of the lateral side member 130, 132 and the lateral bracket structure 137 being secured to the outer surface of the lateral side member 130, 132 with an anchoring mechanism.

It is noted that the support board bracket assembly 139 may be secured to the left or right lateral side member 130, 132 at any point along the length of the groove 143 of the lateral side member 130, 132. To facilitate this, the groove 143 of the top surface of the right or left lateral side member 130, 132 may extend the full length or any portion thereof of the side members 130, 132. Similarly, the openings 145 on the left and right lateral side members 130, 132 may extend the full length or any portion thereof of the side members 130, 132 so the support board bracket assembly 139 may be positioned at any point along the length of the lateral side members 130, 132.

Stated differently, the left and right lateral side members 130, 132 may include more than two openings 145 on the outer surface to accommodate positioning the support board bracket assembly 139 at more than one location along the length of the support structure to accommodate the size and shape of the patient. The left and right lateral side members 130, 132 are configured so that the support board bracket assembly 139 can be easily attached and detached from the left or right lateral side members 130, 132 even with the surgical drapes in place. It is understood that the lateral support board 134 is only attached and detached with the patient support structure 104 and the patient in a substantially prone position.

The lateral support board 134 may further include contoured support pads or cushions of varying sizes. The support pads may be removable by hook and loop fasteners or other mechanisms. The support pads may also be positionable on any desired part of the lateral support board 134. In certain surgical procedures, such as a prone-only procedure, the lateral support board 134 may be removed from the surgical table 100. In certain surgical procedures, such as prone-lateral-prone surgical procedures, the lateral support board 134 may be employed only during the lateral portion of the procedure and thereafter be released and removed for the prone portions of the procedure without having to re-drape the patient, and thereby providing access for the surgical assistant if one is needed.

As seen in FIGS. 4-8, the upper body support structure 114 may include a pair of left and right upper body support members 120, 122 that are coupled with and cantilevered off of the head end plate 116. The support members 120, 122 reside above a head end of the right and left lateral side members 130, 132. The upper body support structure 114 may also include a tray 123 that slides on and extends between the pair of upper body support members 120, 122. A torso or chest pad 140 may be positioned on the tray 123, and a pair of left and right arm supports 124, 126 may be coupled to the head end plate 116 through adjustable bars.

The pair of upper body support members 120, 122 of the upper body support structure 114 may extend longitudinally from the head end plate 116 and relative to the outer frame 112. In such a way, once the tray 123 and the pad 140 are locked onto the pair of upper body support members 120, 122, the pair of upper body support members 120, 122 may be extended or retracted via actuators 280 and locked at an appropriate longitudinal orientation relative to the pelvic pads 142, 144 for a given patient's trunk height. Alternatively, the pair of left and right upper body support members 120, 122 may be fixed relative to the head end plate 116, and only the tray 123 and attached pad 140 and arm supports 124, 126 may be adjusted along a longitudinal length of the left and right upper body support members 120, 122.

Figure 4:
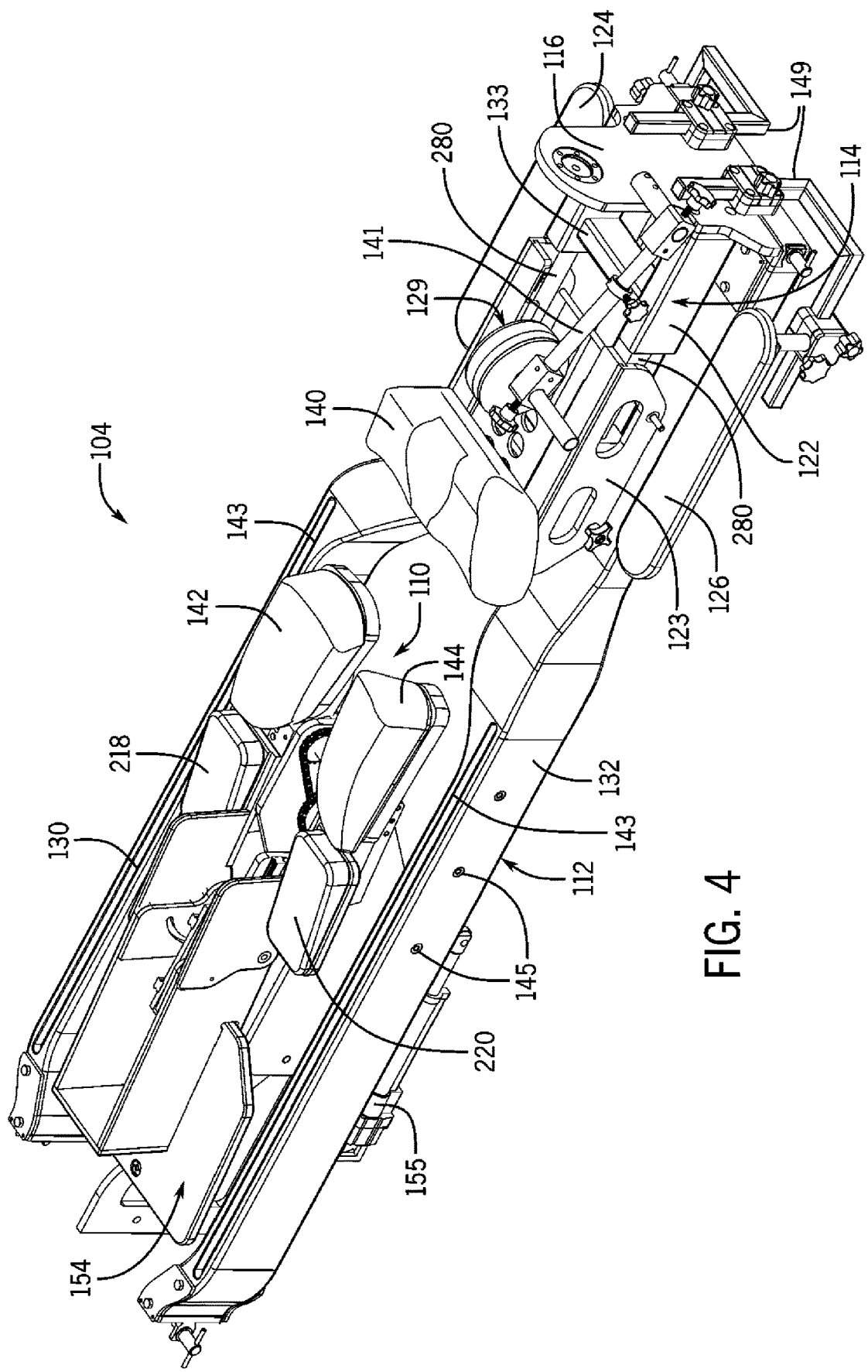
FIG. 4 depicts a perspective view of a patient support structure for prone and lateral positioning, in one embodiment.
Figure 5:
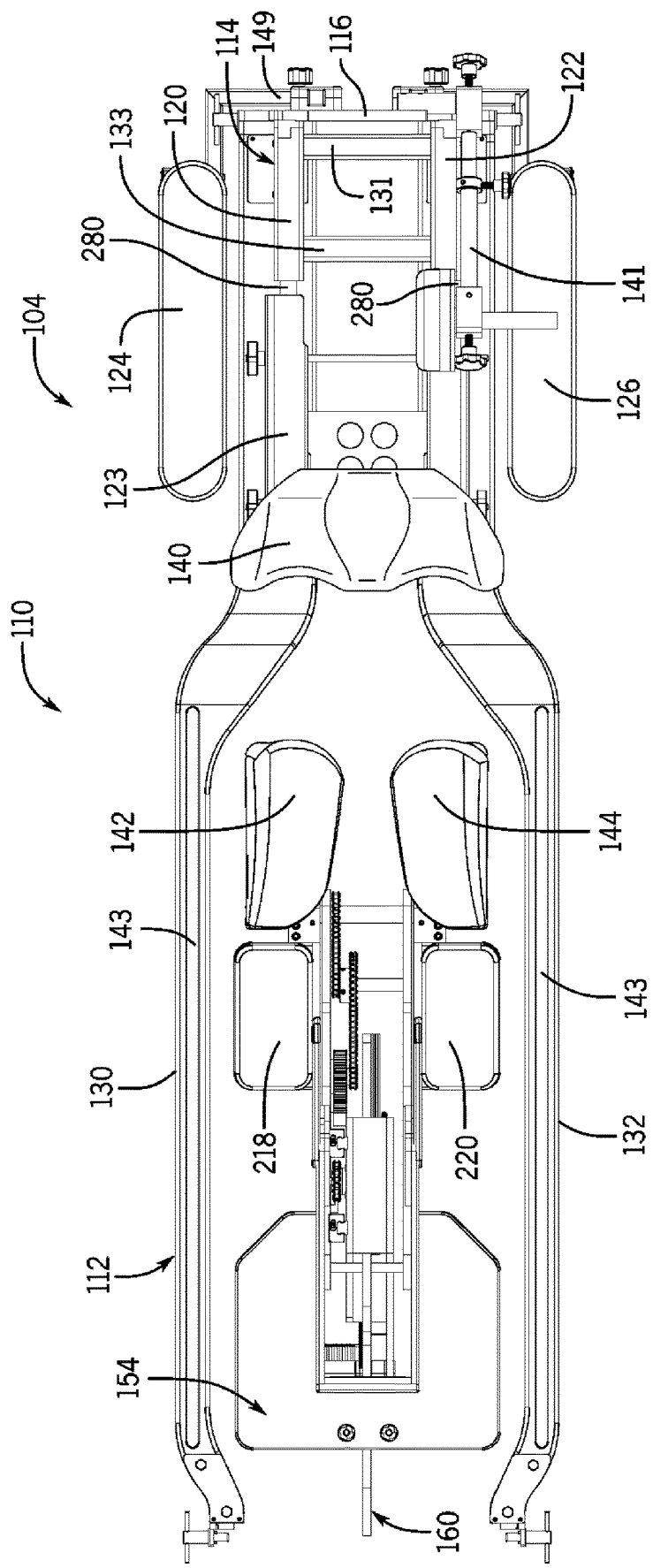
FIG. 5 depicts a top view of a patient support structure for prone and lateral positioning, in one embodiment.
Figure 6:
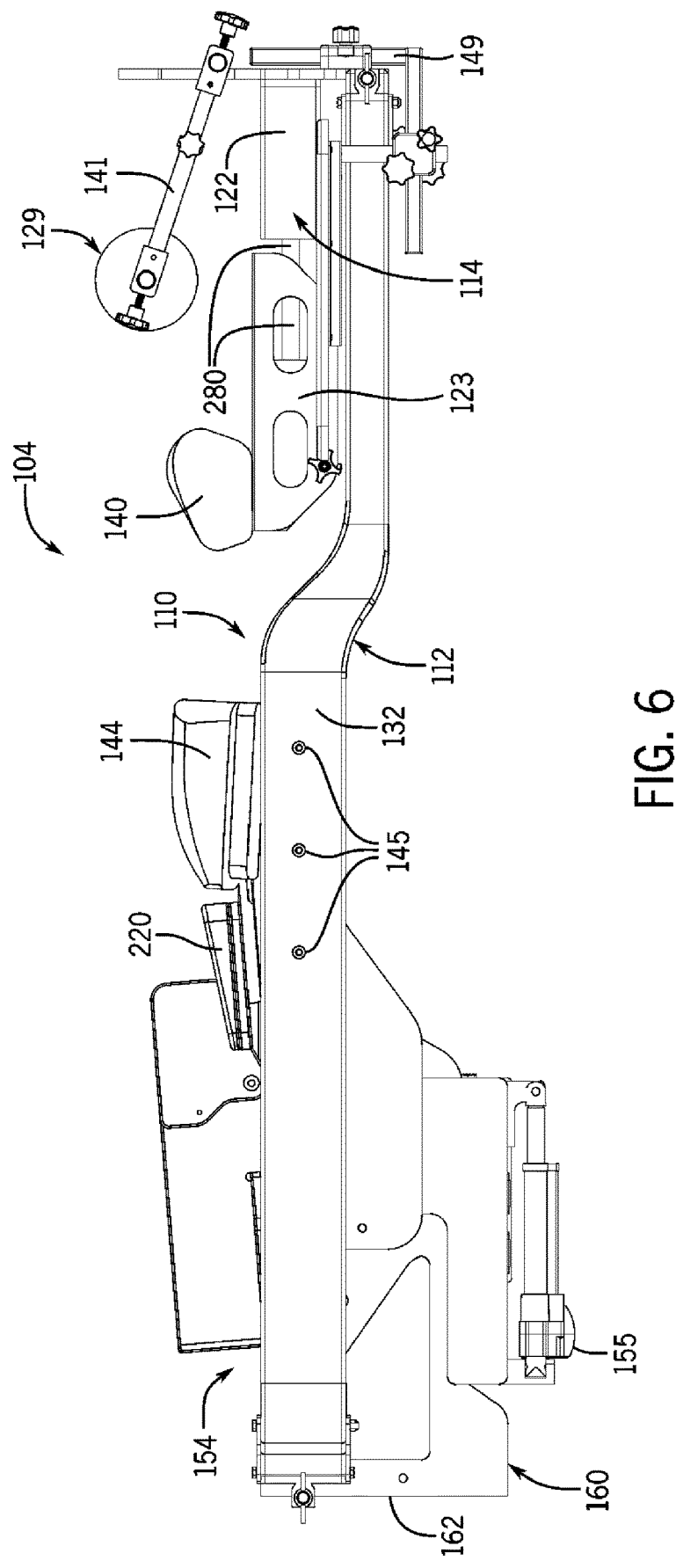
FIG. 6 depicts a right side view of a patient support structure for prone and lateral positioning, in one embodiment.
Figure 7:
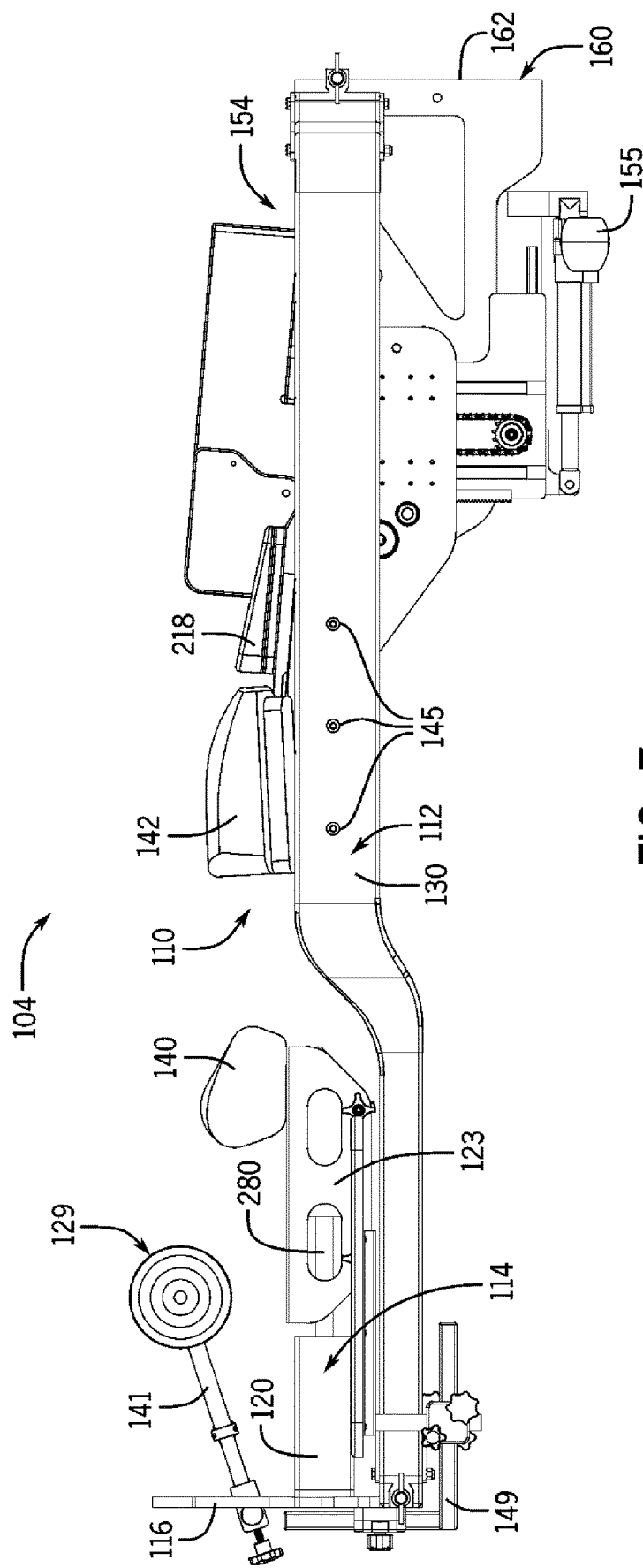
FIG. 7 depicts a left side view of a patient support structure for prone and lateral positioning, in one embodiment.

The right and left upper body support members 120, 122 may be coupled to a head end plate 116 at a first end, where the head end plate 116 is further coupled to the head end rotation assembly 125. The right and left upper support members 120, 122 are cantilevered off of the head end plate 116 such that a second end of the right and left upper support members 120, 122 are unattached to another portion of the patient support structure 104 or the base 102. The upper body support structure 114 further includes a pair of cross bracing members 131, 133 extending between right and left upper support members 120, 122. The left and right arm supports 124, 126 may extend from the upper body support members 120, 122 or may be supported by or cantilevered from a bracket 149 secured to the head end of the lateral side members 130, 132, as seen in FIG. 4.

In an embodiment, and as seen in FIGS. 9 and 10, the left arm support 124 may be supported from a bracket 149 secured to the head end plate 116 and the right arm support 126 may be supported from a bracket 149 secured to head end plate 116. The left arm support 124 and the right arm support 126 may include pads. In various examples, the pads may be removable and attached to the left and right arm supports 124, 126 by Velcro® or another hook and loop-type fastener. The tray 123 may be slidable along the right and left upper support members 120, 122 and locked at an appropriate longitudinal orientation for a given patient's trunk height. Cushions, pillows, or the like may be used on the tray 123 to support the patient's head. In various examples, the cushions may be removable and attached to the tray 123 by Velcro® or another hook and loop-type fastener.

As seen in FIGS. 1, 2A, and 3-4, among others, the surgical table 100 includes a lower body support structure 110 positioned within the lateral support members 130, 132 of the outer frame structure 112. The lower body support structure 110 of the surgical table 100 supports the patient's lower body including the pelvis and lower limbs. The lower body support structure 110 may move the patient's lower body through various positions including flexion and extension.

As further seen in FIGS. 13-15A, the lower body support structure 110 includes a right lower body support section 138 and a left lower body support section 136. The right and left lower body structure sections 138, 136 are substantially a mirror-image of each other. The right and left lower body support structure sections 138, 136 each include an upper leg member 146, 148 which each include a pelvic support member 150, 152 and a thigh support member 156, 158. The right lower body support structure section 138 also includes a right leg portion of a lower leg support assembly 154. The left lower body support structure section 136 also includes a left leg portion of a lower leg support assembly 154. In an embodiment, the thigh support members 156, 158 may be a single member that spans from the left lower body support section 136 to the right lower body support section 138. Alternatively, the thigh support members 156, 158 may be separate members.

Pelvic pads 142, 144 are attached to the pelvic support members 150, 152, and thigh pads 218, 220 are attached to the thigh support members 156, 158, respectively. The left and right upper leg members 146, 148 pivot relative to the lower leg support assembly 154 at a joint 153 and, thus, allow the patient's pelvis to pivot and translate (move along an arc of motion) during articulation or movement of the lower body support structure 110 relative to the outer frame 112 so that a distance between the chest pad 140 and a proximal point on the pelvic pads 142, 144 does not substantially change, as further described herein. The lower leg support assembly 154 may be a single member that spans from the left lower body support section 136 to the right lower body support section 138. The lower leg support assembly 154 may be locked or fixed in a position or rotation at the joint 153 with each of the upper leg members 146, 148. In an embodiment, the lower leg support assembly 154 may be coupled to the foot end plate 118.

Figure 15A:
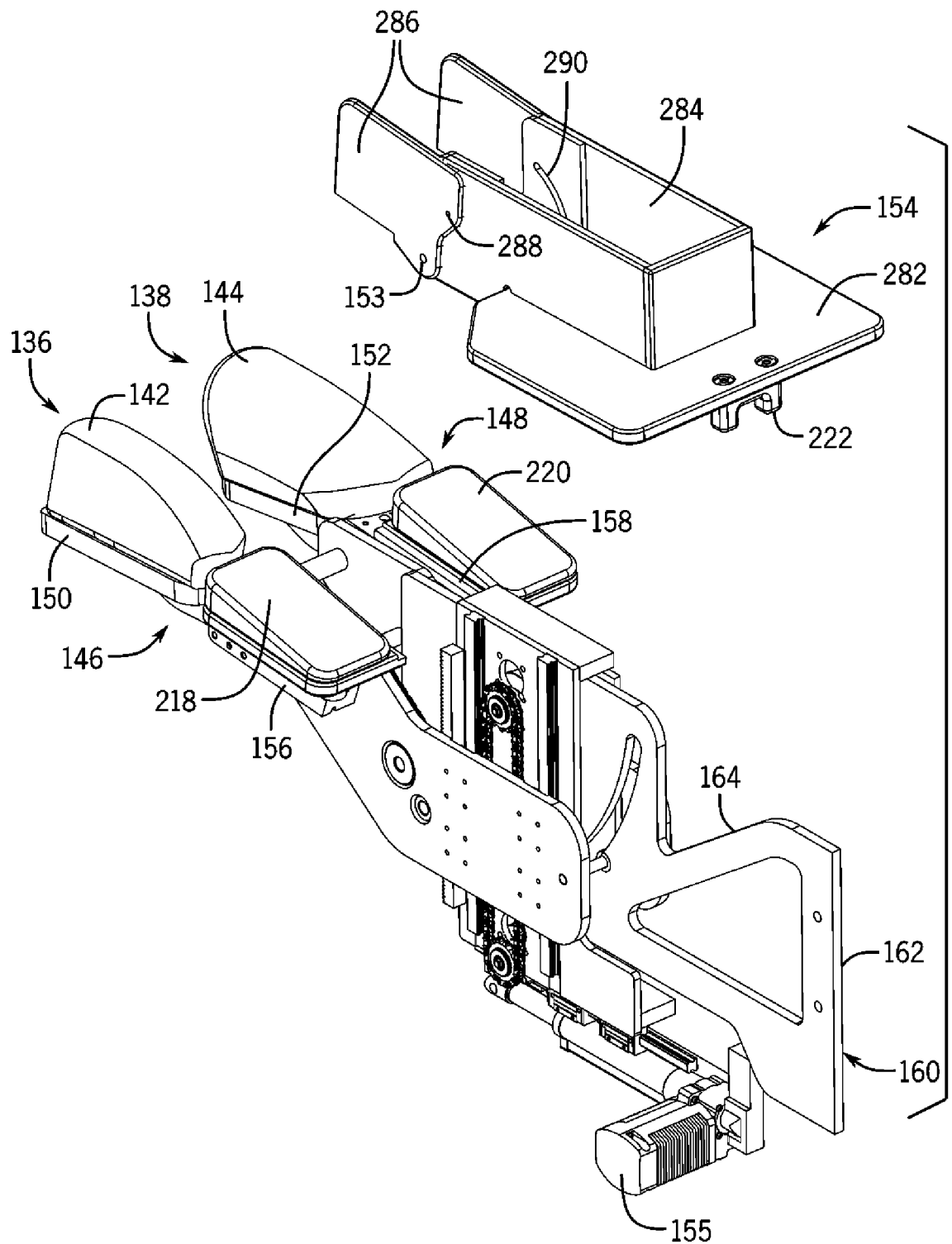
FIG. 15A depicts a perspective view of a lower body support structure for prone and lateral positioning with the lower leg assembly removed, in one embodiment.
Figure 15B:
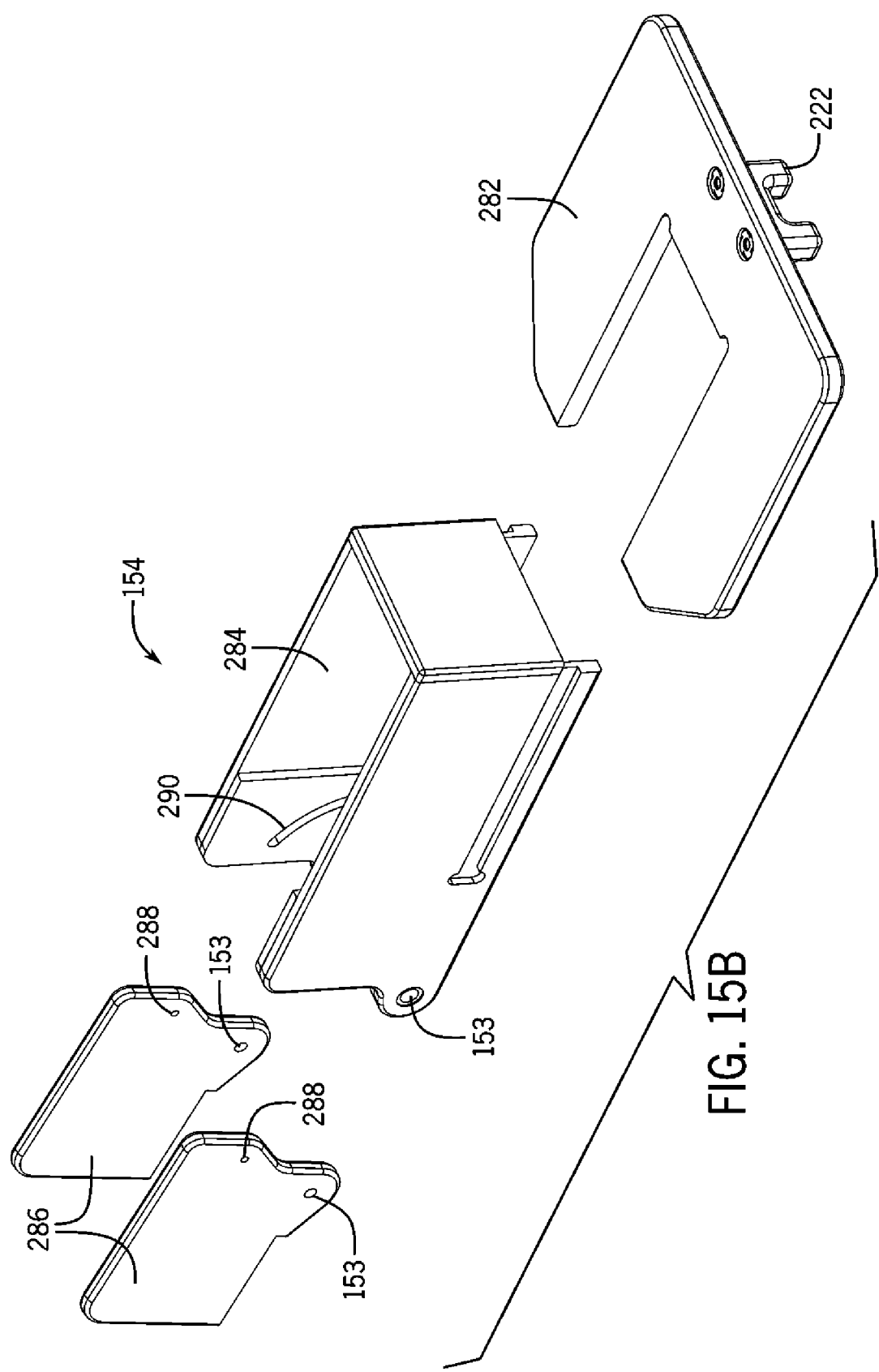
FIG. 15B depicts an exploded perspective view of the lower leg assembly, in one embodiment.

As seen in FIGS. 15A and 15B, lower leg support assembly 154 may include a guide 222 that couples to a foot end of the lower leg support assembly 154 and that slidingly engages a ramped section 164 of a central support structure 160. The guide 222 may be a U-shaped bracket that sandwiches a portion of the ramped section 164 of the central support structure 160 and guides movement of the lower leg support assembly 154 during articulation of the lower body support structure 110. That is, the lower leg support assembly 154 may be free to pivot at the joint 153, but may be constrained in pivoting by the interaction of the guide 222 against the ramped section 164.

The lower leg support assembly 154 may also include a lower leg plate 282, a lower leg housing 284, and a pair of lower leg extensions 286. The lower leg plate 282 couples with the lower leg housing 284, and they are collectively pivotal relative to the pair of lower leg extensions 286 via the pair of pivots 153. A pin 288 extending through the lower leg extension 286 may be received within an arcuate slot 290 on the lower leg housing 284 such that rotation about the joints 153 is restrained by the length of the slot 290.

As seen in FIGS. 13-14, and 16-18, the lower body support structure 110 may include the central support structure 160 between the left lower body support section 136 and the right lower body support section 138. The central support structure 160 is cantilevered off of the foot end plate 118. More particularly, the central support structure 160 angles downward at the ramped section 164 and extends towards the head end while being coupled in between the right and left lateral side members 130, 132 on the foot end plate 118. In other words, the central support structure 160 does not directly connect to the head end of the base 102 or the upper body support structure 114, but instead extends to about a midway point between the head end and foot end of the base 102. The central support structure 160 supports the left and right lower body support structure sections 136, 138 such that the frame sections 136, 138 move relative to the central support structure 160.

As seen in the figures, the central support structure 160 includes a foot end section 162, a ramped or angled section 164, and a lower body support section 128. The ramped or angle section 164 supports the guide 222 of the lower leg support assembly 154 as it slides thereon.

As seen in the figures and in certain instances, the lower body support structure 110 and, in particular, the central support structure 160 is not coupled to the outer frame 112 of the patient support structure 104; rather, the central support structure 160 is supported off of the foot end support structure 108 and foot end plate 118 in a cantilevered fashion by the foot end section 162 of the central support structure 160. In certain instances, the motor end of the linear actuator 155 may be coupled with the central support structure 160, or, alternatively, the motor end of the linear actuator 155 may be coupled with the foot end support structure 108 at, for example, the foot end plate 118.

In an embodiment, the central support section 128 of the central support structure 160 has a generally planar structure. The central support section 128 is engaged with the left and right lower body support sections 136, 138 such that the left and right lower body support sections 136, 138 are movable relative to the central support structure 160.

The left lower body support section 136 may include a left outer translation panel 292 and a left inner translation panel 294. Similarly, the right lower body support section 138 may include a right outer translation panel 296 and a right inner translation panel 298. The left inner translation panel 294 and the right inner translation panel 298 may collectively be referred to as the inner translation structure 294, 298. And the left outer translation panel 292 and the right outer translation panel 296 may collectively be referred to as the outer translation structure 292, 296. Collectively, the inner and outer translation structures 294, 298, 292, 296 along with the linear actuator 155 and related components may be referred to as a lower body translation and rotation structure, which facilitates movement (horizontal and vertical translation, and rotation) of the pelvic pads 142, 144 towards and away from the chest pad 140 with little or no vertical movement of a virtual pivot point/axis associated with the pelvic pads 142, 144.

Figure 22A:
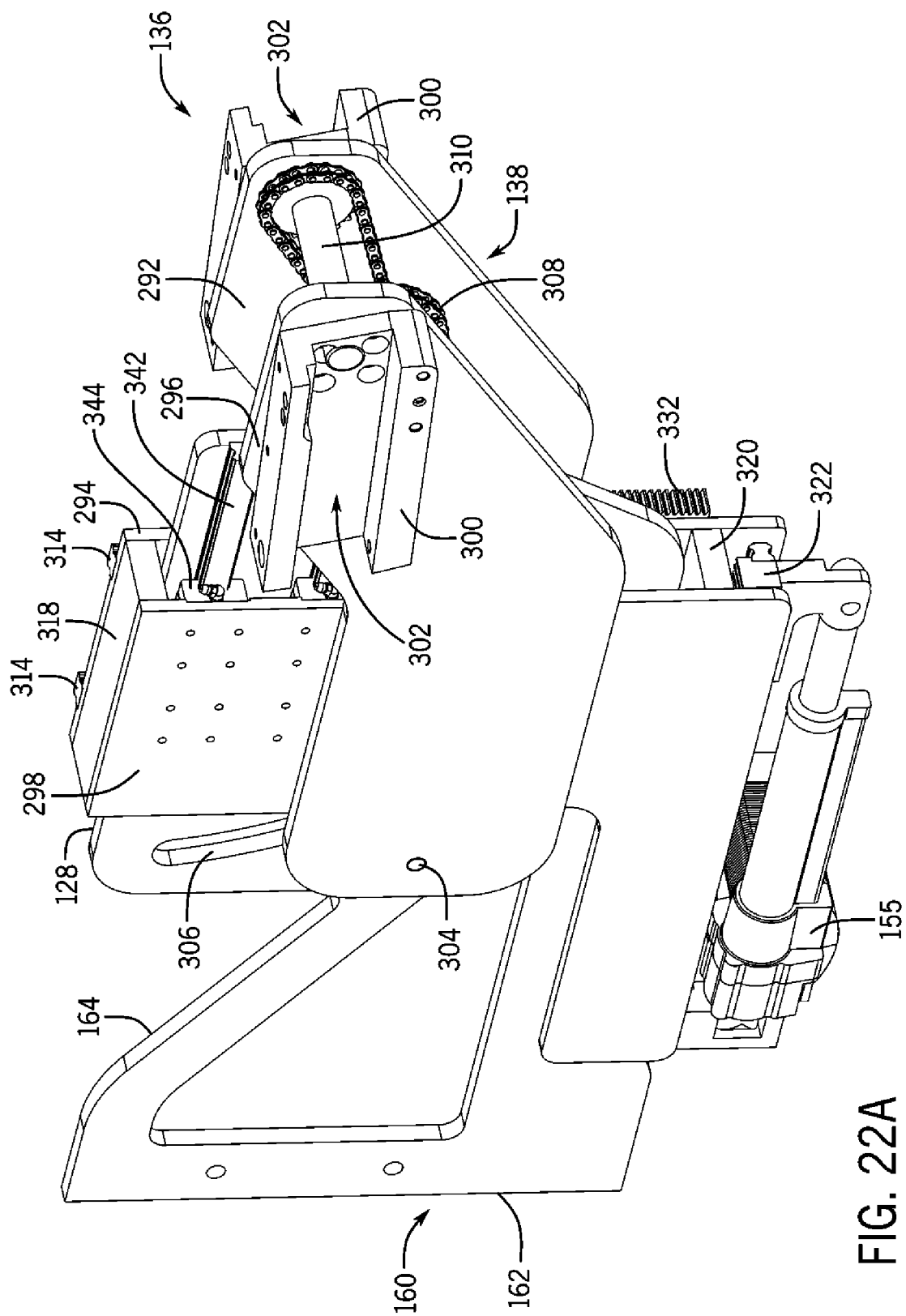
FIG. 22A depicts a perspective view of a right side of the central support structure for prone and lateral positioning showing the rotation of the upper leg mounting bracket, in one embodiment.

The left lower body support section 136 may include an upper leg mounting bracket 300 rotatably coupled to the left outer translation panel 292 (described further in reference to FIG. 22A). The upper leg mounting bracket 300 may include a slot 302 for receiving a portion of the left pelvic support member 150 therein. The right lower body support section 138 may include an upper leg mounting bracket 300 rotatably coupled to the right outer translation panel 296. The upper leg mounting bracket 300 may include a slot 302 for receiving a portion of the right pelvic support member 152 therein. As will be described in reference to FIGS. 23-24, the left and right pelvic support members 150, 152 are pivotal about a pin or axle extending through the slot 302 so as to permit the support members 150, 152 to be moved away from the patient's pelvis away from the surgical area.

Figure 16:
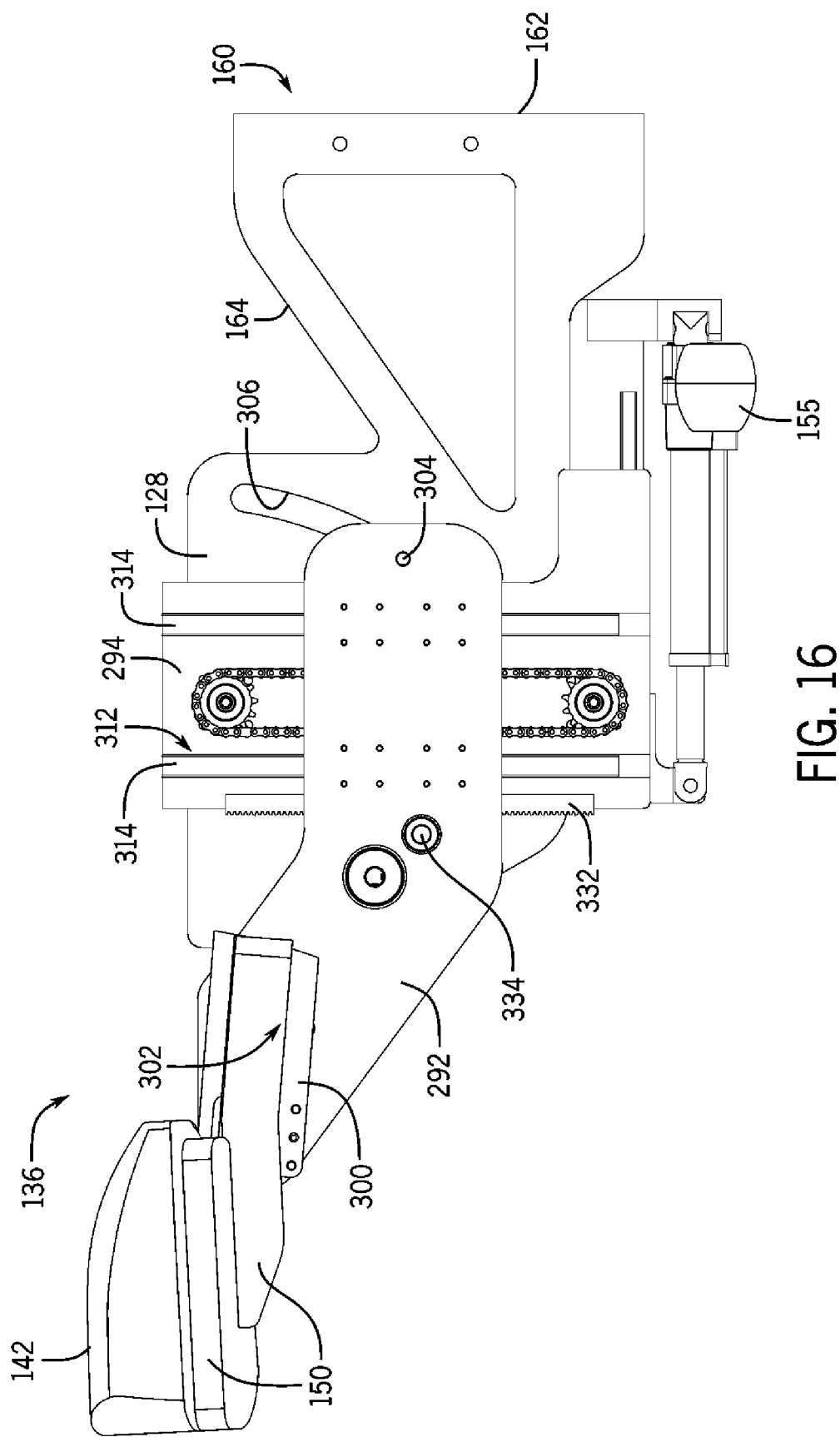
FIG. 16 depicts a left side view of a portion of a lower body support structure for prone and lateral positioning, in one embodiment.
Figure 17:
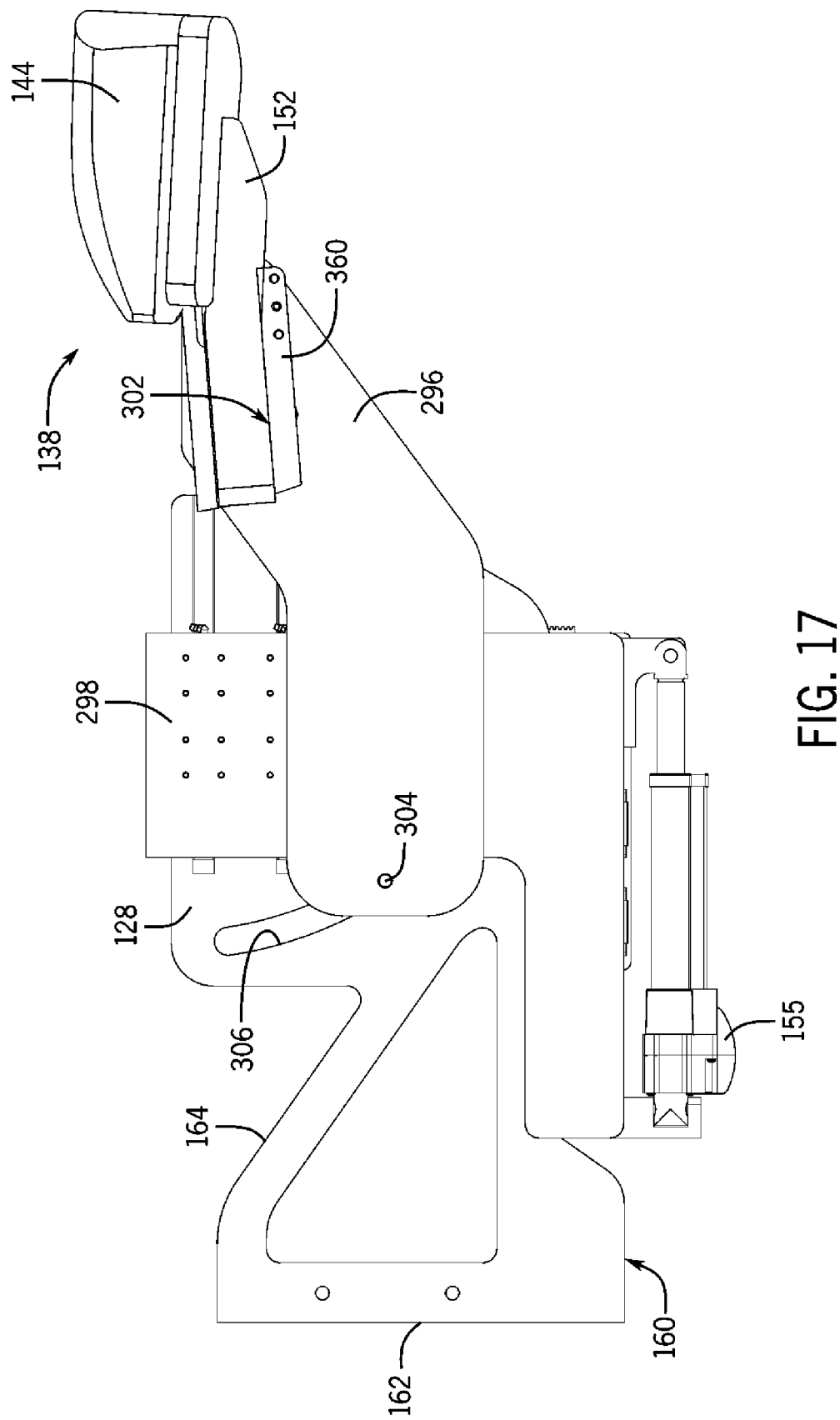
FIG. 17 depicts a right side view of a portion of a lower body support structure for prone and lateral positioning, in one embodiment.
Figure 18:
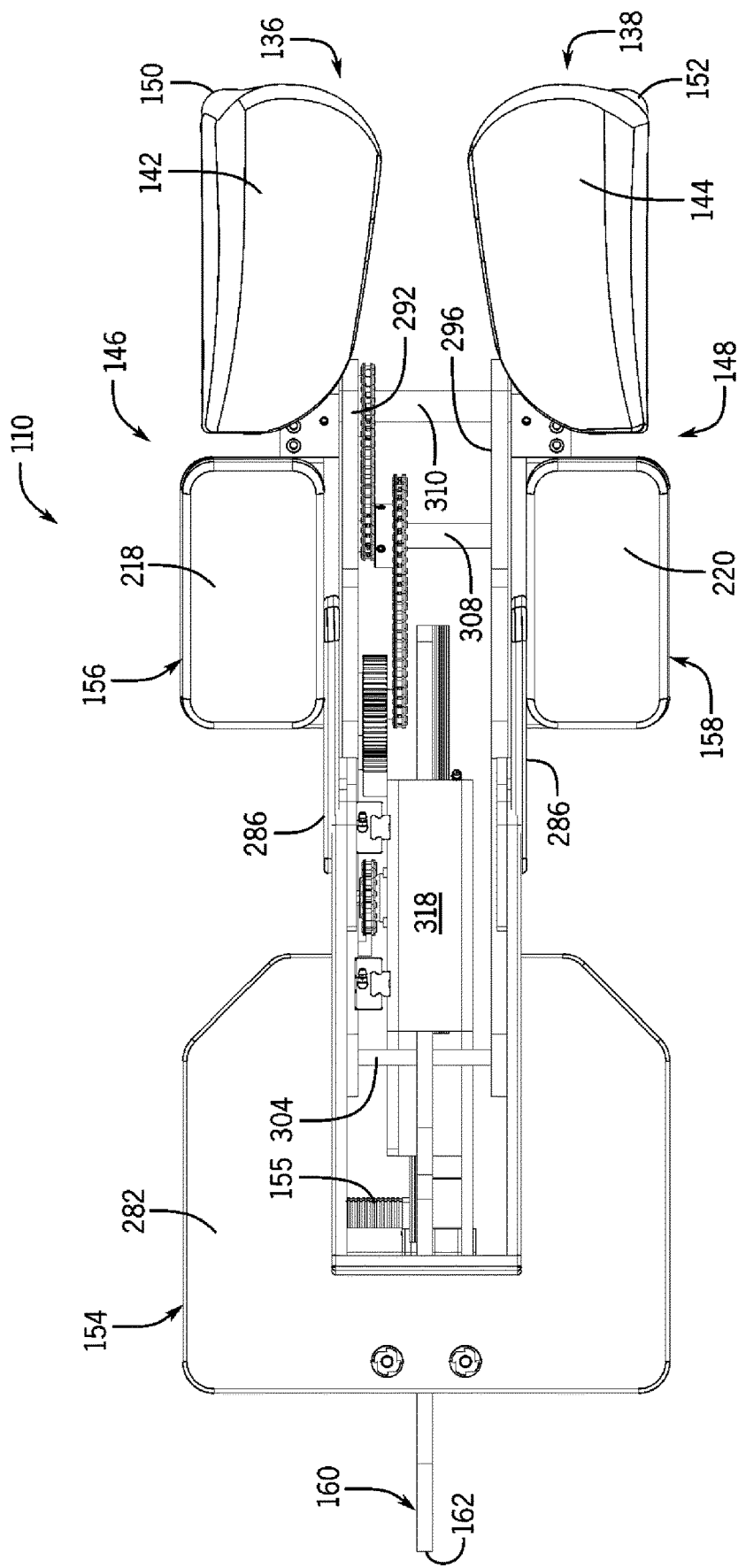
FIG. 18 depicts a top view of a lower body support structure for prone and lateral positioning, in one embodiment.

As seen in FIGS. 16-18, the left and right outer translation panels 292, 296 are coupled together at a foot end by an axle 304 that is fitted within an arcuate slot 306 in the central support section 128 of the central support structure 160. At a head end, the left and right outer translation panels 292, 296 are also coupled together by a first shaft 308, and a second shaft 310, as best seen in FIGS. 18-20.

The left and right outer translation panels 292, 296 are slidingly coupled to the left and right inner translation panels 294, 298 via a vertical linear rail system 312. More particularly, the vertical linear rail system 312 includes rails 314 coupled in a vertical fashion to the left inner translation panel 294 and guides or carriages 316 coupled to an inner surface of the left outer translation panel 292. The guides 316 ride in a linear fashion on the corresponding rails 314 such that the left and right outer translation panels 292, 296 vertically translate relative to the left and right inner translation panels 294, 298. And because the left and right outer translation panels 292, 296 are constrained in their vertical translation by the axle 304 in the slot 306 of the central support section 128, the left and right outer translation panels 292, 296 also translate horizontally, as will be discussed subsequently.

Figure 19:
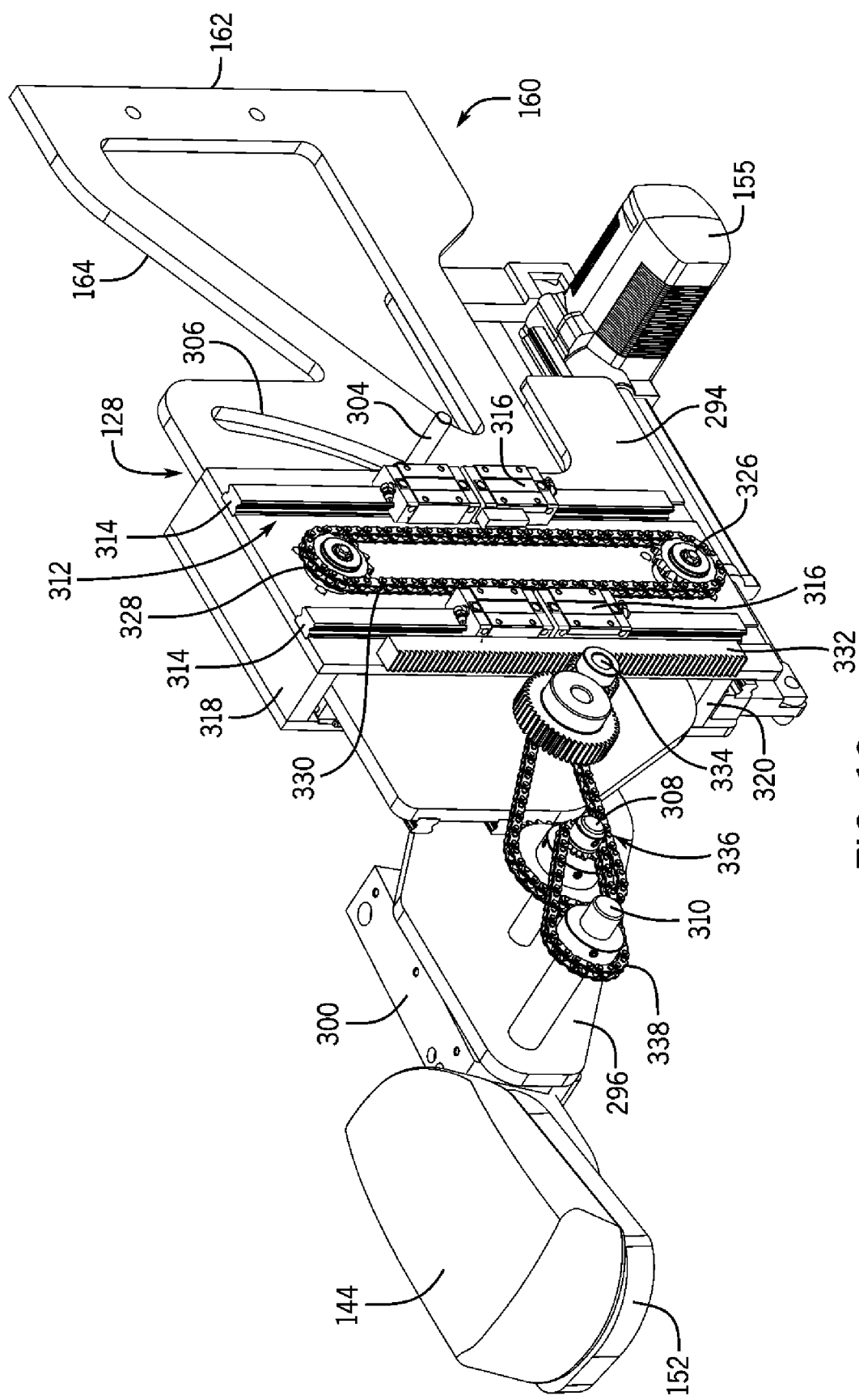
FIG. 19 depicts a perspective view of a left portion of the central support structure for prone and lateral positioning along with a portion of the right lower body support structure, in one embodiment.
Figure 20:
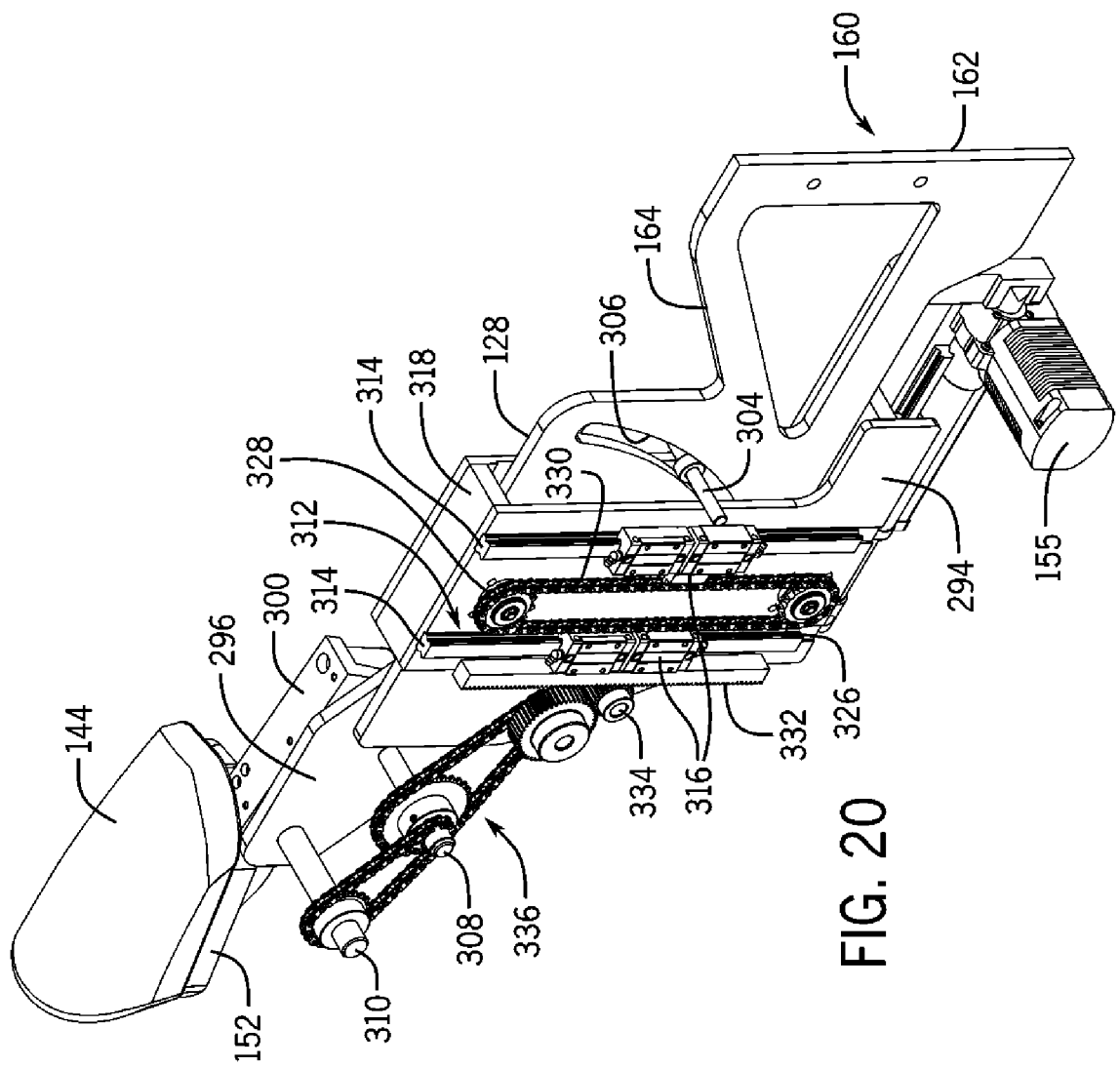
FIG. 20 depicts a perspective view of a left portion of the central support structure for prone and lateral positioning along with a portion of the right lower body support structure, in one embodiment.

As seen in FIGS. 19-21, the left and right inner translating panels 294, 298 are coupled together via a top member 318 and a bottom member 320. As best seen in FIG. 21, the linear actuator 155 is coupled at a motor end to a bottom end of the left and right inner translating panels 294, 298, and an opposite end is coupled to a toothed rack 322 that is, in turn, engaged with a pinion gear 324. So, as the arm of the actuator 155 extends and retracts, the rack 322 also extends and retracts, which rotates the pinion gear 324. Opposite the pinion gear 324, as seen in FIGS. 19 and 20, a driver sprocket 326 is rotationally linked with the pinion gear 324. The driver sprocket 326 is linked with a driven sprocket 328 via a chain 330. A right segment of the chain 330 is coupled with the guides 316 on the right, as seen in FIGS. 19 and 20, and a left segment of the chain 330 is not coupled to the guides 316 adjacent it (because the left segment of the chain 330 moves in an opposite direction from the right segment). Thus, as the chain 330 is rotated, the guides 316 are translated vertically on the rails 314.

Also as seen in FIGS. 19 and 20, a vertical rack 332, adjacent the guides 316 coupled to the chain 330, is mounted to the left inner translating panel 294. A pinion gear 334 is engaged with the rack 332 and also the left outer translating panel 292. The pinion gear 334 is connected through a gear system 336 that ultimately couples a chain 338 to the first shaft 308 and the second shaft 310. As described previously, the second shaft 310 couples to the left and right upper leg mounting brackets 300 through the left and right outer translating panels 292, 296, respectively, so the mounting brackets 300 are pivotal relative to the panels 292, 296 when the shaft 310 rotates.

Thus, rotation of the mounting brackets 300 (and thus the left and right pelvic support members 150, 152) is caused by vertical translation or movement of the left and right outer translating panels 292, 296, which causes the pinion gear 334 to rotate against the rack 332, which causes the gear system 336 to operate, which causes the second shaft 310 to rotate. And, as described previously, the linear actuator or motor 155 may begin the process by extending or retracting the arm so as to rotate the pinion gear 324, which causes the driver sprocket 326 to rotate, which causes the chain 330 to rotate, which raises the guides 316 (on the right segment of the chain 330), which raises the left and right outer translating panels 292, 296.

Turning to FIGS. 17 and 21, the left and right inner translating panels 294, 298 are slidingly coupled to the central support section 128 of the central support structure 160 via a horizontal linear rail system 340. More particularly, the horizontal linear rail system 340 includes rails 342 coupled in a horizontal fashion to the right side of the central support section 128 and guides or carriages 344 coupled to an inner surface of the right inner translation panel 298. In this way, the left and right inner translating panels 294, 298 may slide in a horizontal direction (between the head end and foot end) via the horizontal linear rail system 340 to cause the left and right outer translating panels 292, 296, and, ultimately, the left and right pelvic support structures 150, 152 and the attached pads 142, 144 to also translate horizontally towards and away from the upper body support structure 114.

In certain instances, the left and right inner translating panels 294, 298 may translate horizontally relative to the central support structure 160, while not moving vertically. In certain instances, the left and right outer translating panels 292, 296 may translate horizontally via the horizontal movement of the left and right inner translating panels 294, 298. The left and right outer translating panels 292, 296 may also vertically translate via the vertical linear rail system 312 that couples the outer translating panels 292, 296 to the inner translating panels 294, 298. The combined vertical and horizontal movement or translation of the left and right outer translating panels 292, 296 causes the left and right pelvic support structures 150, 152 and the attached pads 142, 144 to move accordingly. And as described previously, the vertical movement of the left and right outer translating panels 292, 296 may cause rotation of the left and right pelvic support structures 150, 152 and the attached pads 142, 144. This combined vertical movement, horizontal movement, and rotational movement of the pelvic support structures 150, 152 and pads 142, 144 may be accomplished while the upper body support structure 114 remains unmoved or still relative to the head end support structure 106. Thus, the lower body support structure 110 may facilitate sliding in at least two dimensions and rotating along at least one axis.

Turning to FIG. 22A, which depicts a perspective view of the central support structure 160, the inner translation structure 294, 298, and the outer translation structure 292, 296, the mounting brackets 300 are rotationally coupled with the second shaft 310, which is driven by the chain 338, which is ultimately driven by the linear actuator 155. As described previously, the mounting brackets 300 may receive a portion of the pelvic support members 150 within the slots 302 of the brackets. Thus, as the brackets 300 are rotated via the linear actuator 155, the pelvic support members 150 and the attached pads 144, 142, as well as the thigh support members 156, 158 and the attached pads 218, 220, which are attached to the top of the brackets 300, also rotate.

Figure 22B:
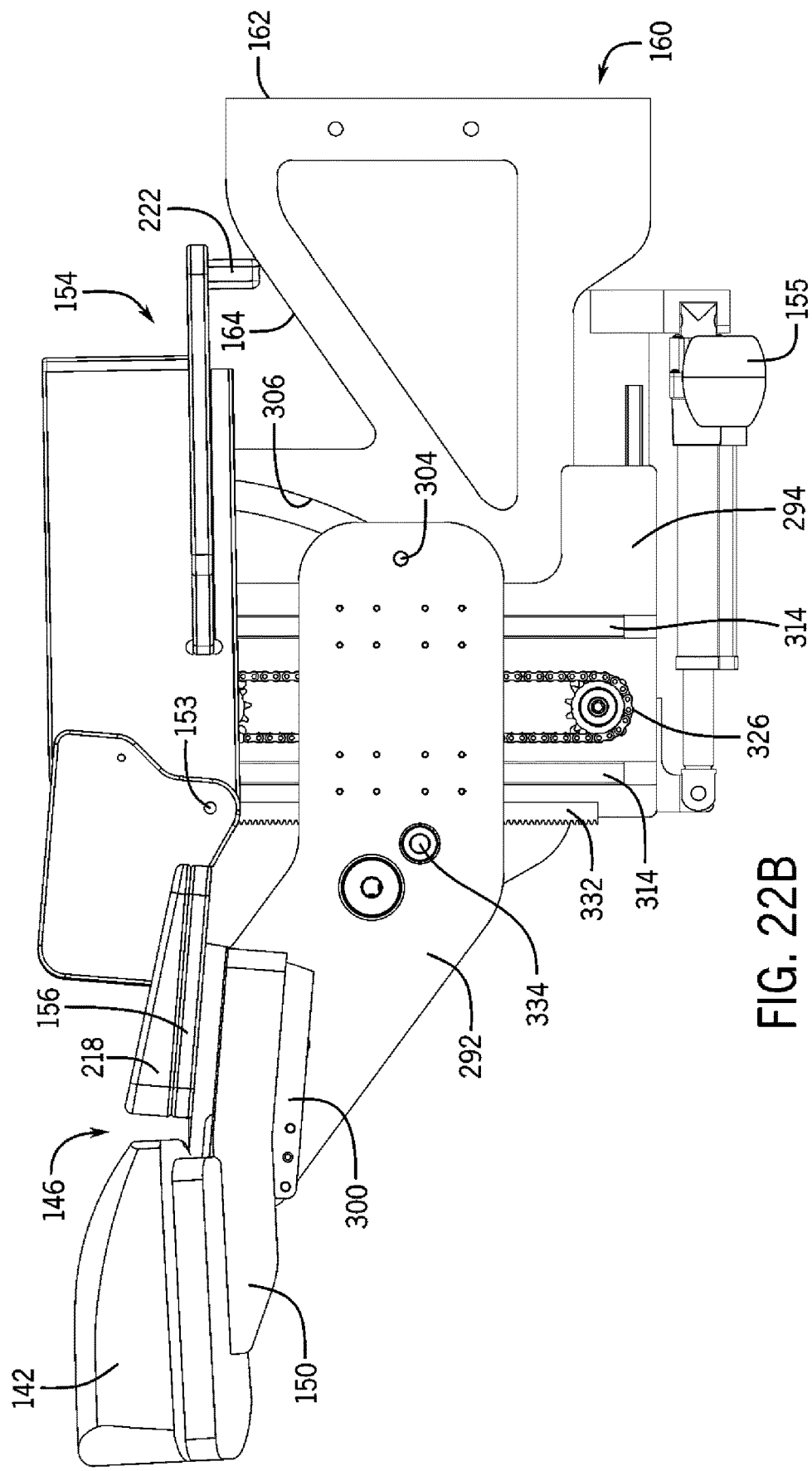
FIG. 22B depicts a left side view of the lower body support structure in a neutral position, in one embodiment.
Figure 22C:
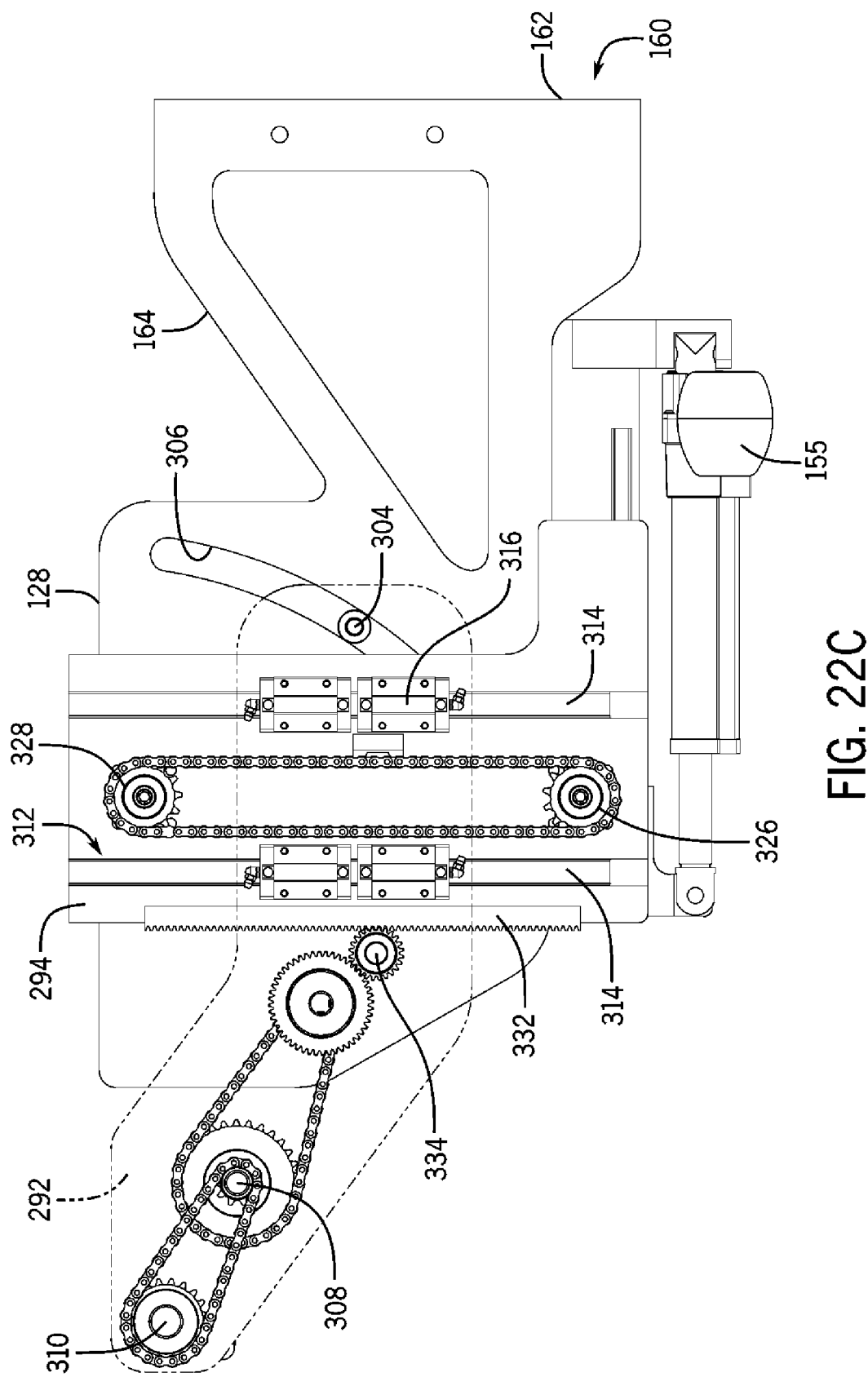
FIG. 22C depicts a left side view of a portion of the lower body support structure in a neutral position with the left lower leg panel shown transparently, in one embodiment.
Figure 22D:
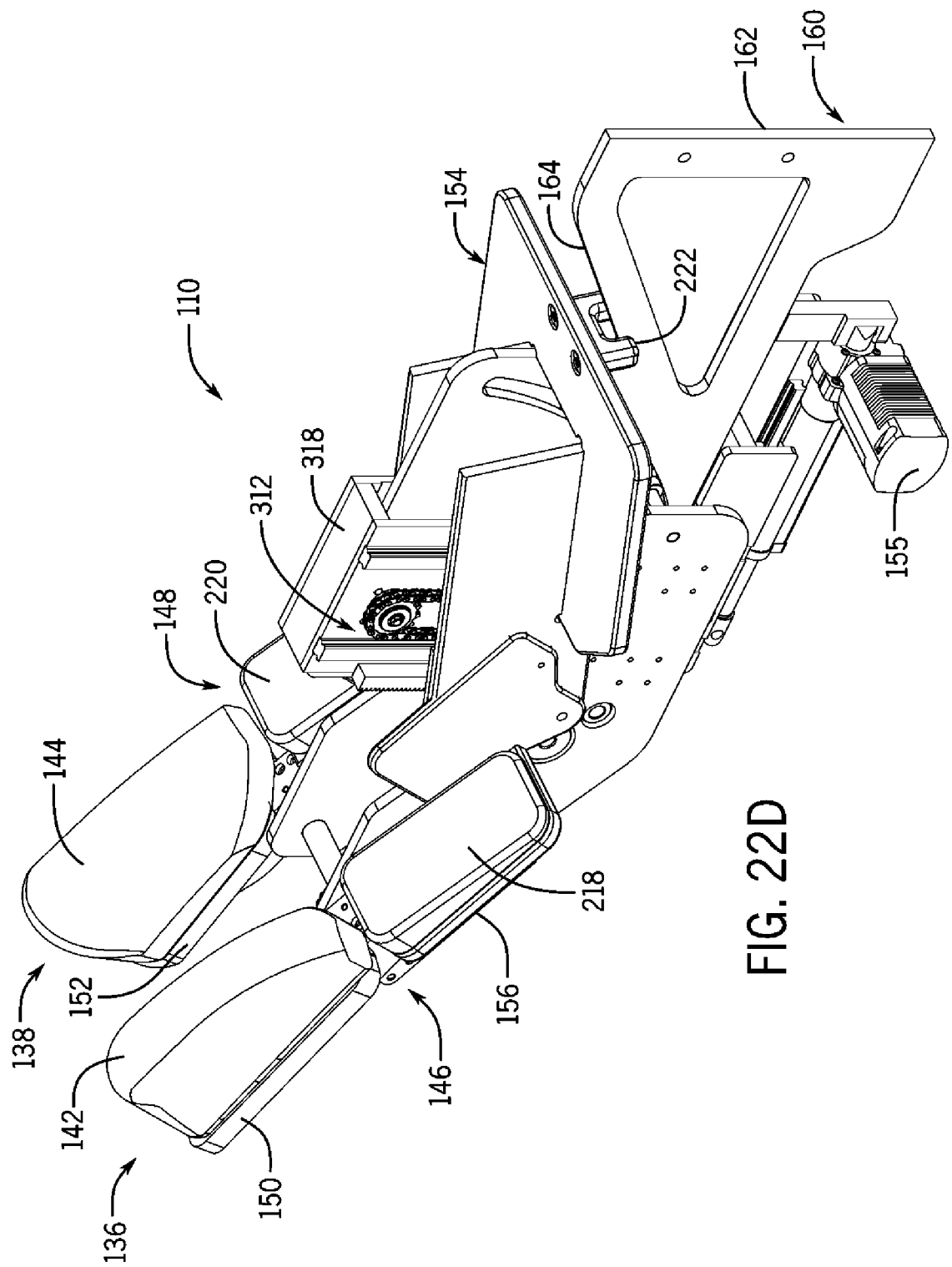
FIG. 22D depicts a perspective view of the lower body support structure in a flexed position, in one embodiment.
Figure 22E:
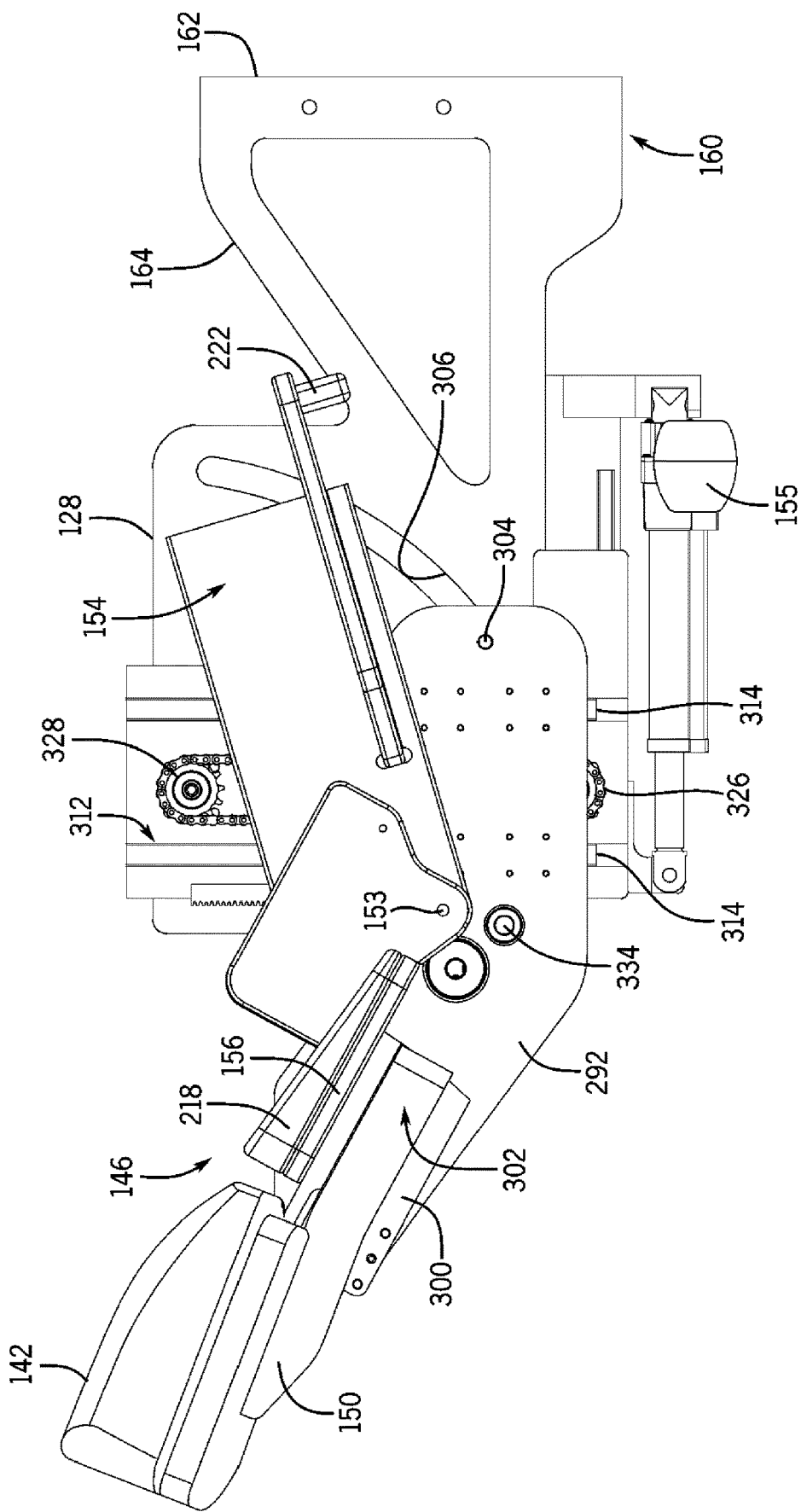
FIG. 22E depicts a left side view of the lower body support structure in the flexed position, in one embodiment.
Figure 22F:
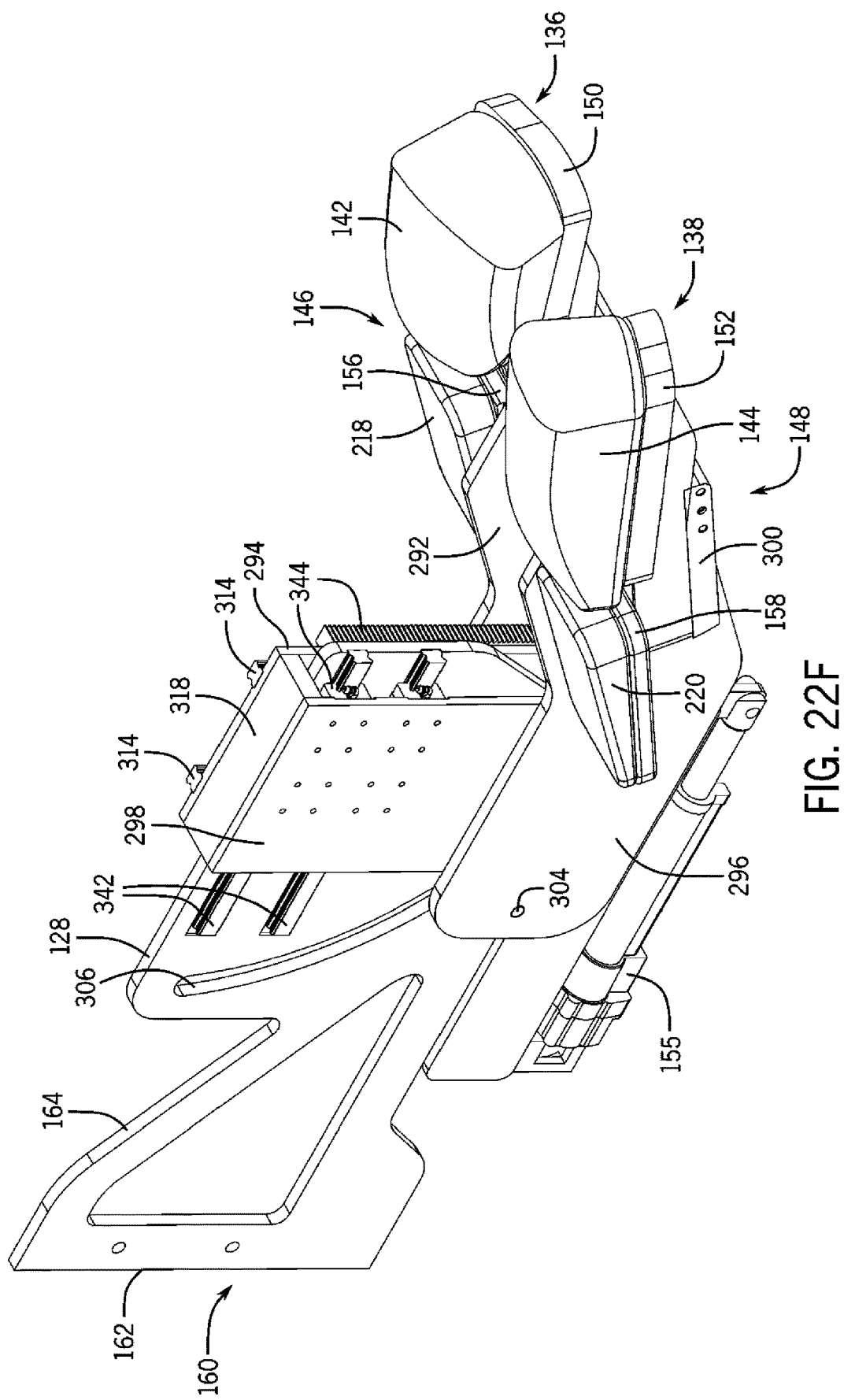
FIG. 22F depicts another perspective view of the lower body support structure in the flexed position, in one embodiment.
Figure 22G:
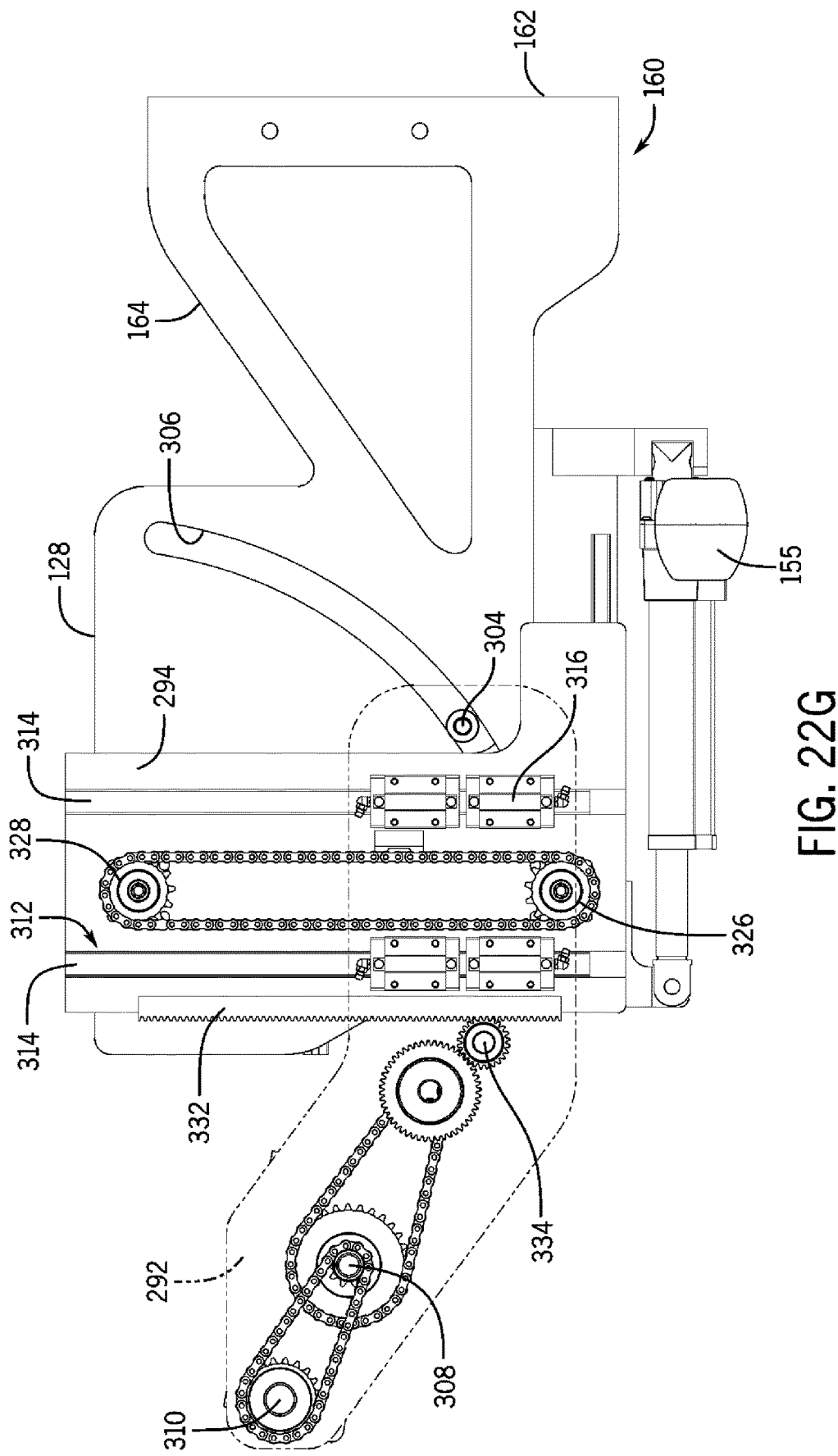
FIG. 22G depicts a left side view of a portion of the lower body support structure in a flexed position with the left lower leg panel shown transparently, in one embodiment.

Next, FIGS. 22B and 22C will be compared with FIGS. 22D-22G. FIGS. 22B and 22C depict, respectively, a side view of the lower body support structure 110 with the lower body support structure sections 138, 136 in a neutral position, and a side view of the central support structure 160, the inner translation structure 294, 298, and the outer translation structure 292, 296 in the neutral position, where the outer translation structure 292, 296 is shown transparently. FIGS. 22D-22G depict, respectively, a perspective view of the lower body support structure 110 with the lower body support structure sections 138, 136 in a flexed position, a side view of the lower body support structure 110 with the lower body support structure sections 138, 136 in the flexed position, another perspective view of the lower body support structure 110 with the lower body support structure sections 138, 136 in the flexed position, and a side view of the central support structure 160, the inner translation structure 294, 298, and the outer translation structure 292, 296 in the flexed position, where the outer translation structure 292, 296 is shown transparently.

Referring to FIGS. 22B and 22C, the upper leg member 146 including the pelvic support member 150 and the attached pad 142, the thigh support member 156 and the attached pad 218, and the lower leg support assembly 154 are generally level or parallel with each other in the neutral position. In the neutral position, as seen in FIG. 22B, the guide 222 contacts the ramped section 164 of the central support structure 160 near a top or foot end thereof. Additionally, in the neutral position, the pelvic pads 142 and the pelvic support member 150 are generally level with the ground. In this position, the outer translation structure 292, 296 is vertically positioned about halfway between the driver and driven sprockets 326, 328. Also in the neutral position, the axle 304 that is fitted within the arcuate slot 306 in the central support section 128 of the central support structure 160 is positioned about at a midpoint between the ends of the slot 306. Additionally, the pinion gear 334 is positioned about halfway up the rack 332 in the neutral position.

Referring to FIGS. 22D-22G, the lower body support structure sections 138, 136 of the lower body support structure 110 are shown in a flexed position. As seen in the figures, the pelvic support members 150, 152 and the thigh support members 156, 158, as well as the attached pads 142, 144, 218, 220, are generally level with each other, but these support members 150, 152, 156, 158 are angled relative to the lower leg support assembly 154 such that a patient positioned thereon would be positioned in flexion. The lower body support assembly 154 is pivoted relative to the support members 150, 152, 156, 158 about the joint 153. To facilitate positioning the patient in flexion, the linear actuator 155 is extended such that the inner translation structure 294, 298 is moved towards a head end of the central support structure 160. In this orientation, the guide 222 slides down towards a head end of the ramped section 164, the axle 304 slides towards a head end of the arcuate slot 306, the pinion gear 334 translates down the rack 332, and the outer translation structure 292, 296 translates downward. Thus, as seen in a comparison of the lower body support structure sections 138, 136 in the neutral and flexed positions, in particular a comparison of FIGS. 22B and 22E, a distance between the foot end section 162 and the pelvic pads 142, 144 is shorter in the neutral position than in the flexed position. Accordingly, the pelvic pads 142, 144 will be closer to the chest pad 140 in the flexed position, as compared to the neutral position.

While not shown in the figures, the lower body support structure sections 138, 136 of the lower body support structure 110 may be positioned in an extended position. To facilitate positioning the patient in extension, the linear actuator 155 is retracted such that the inner translation structure 294, 298 is moved towards a foot end of the central support structure 160. In the extended position, the guide 222 slides up towards a foot end of the ramped section 164, the axle 304 slides towards a top or foot end of the arcuate slot 306, the pinion gear 334 translates up the rack 332, and the outer translation structure 292, 296 translates upward.

Figure 23:
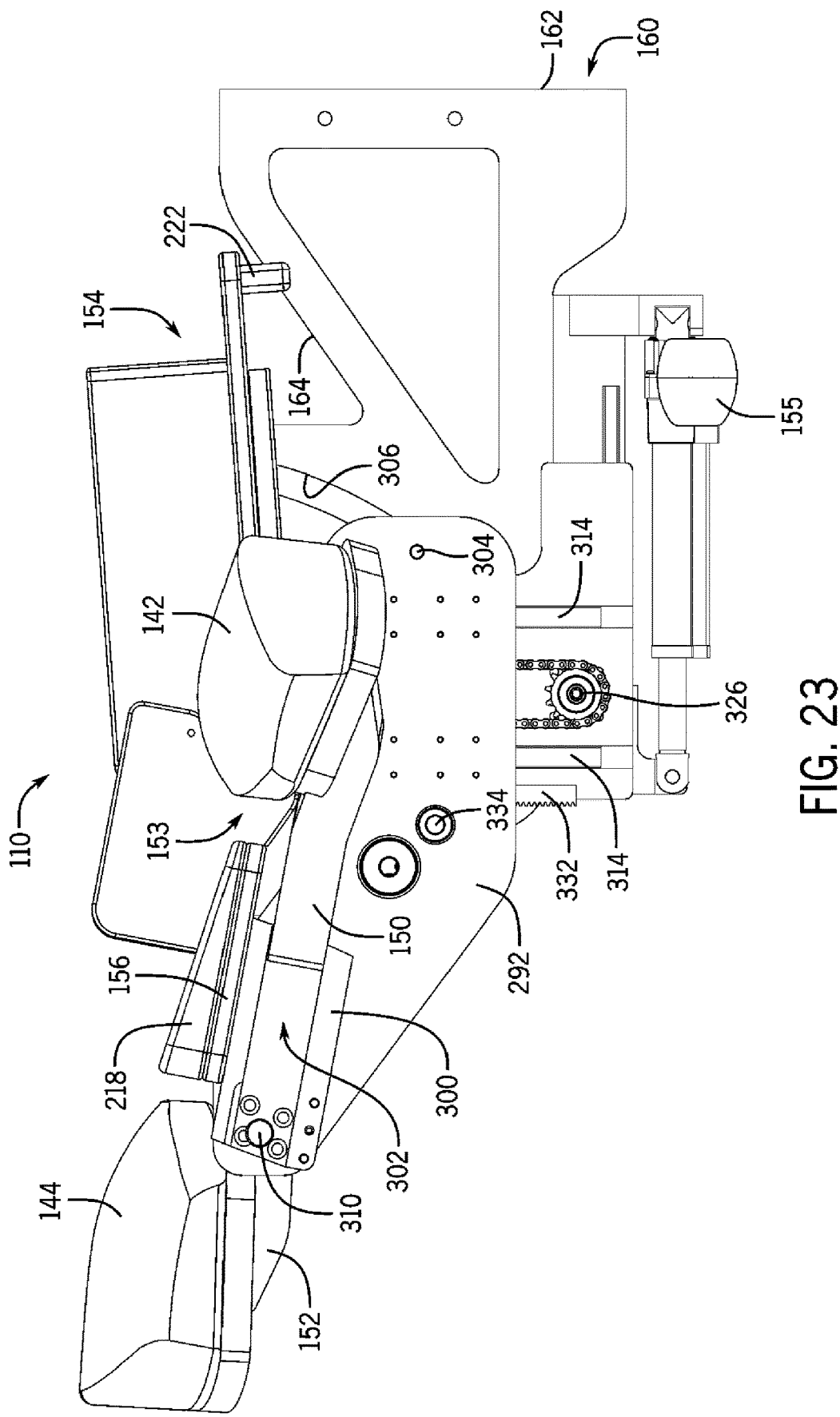
FIG. 23 depicts a side view of a lower body support structure with a left upper leg member pivoted about an axle in the left upper leg mounting bracket, in one embodiment.
Figure 24:
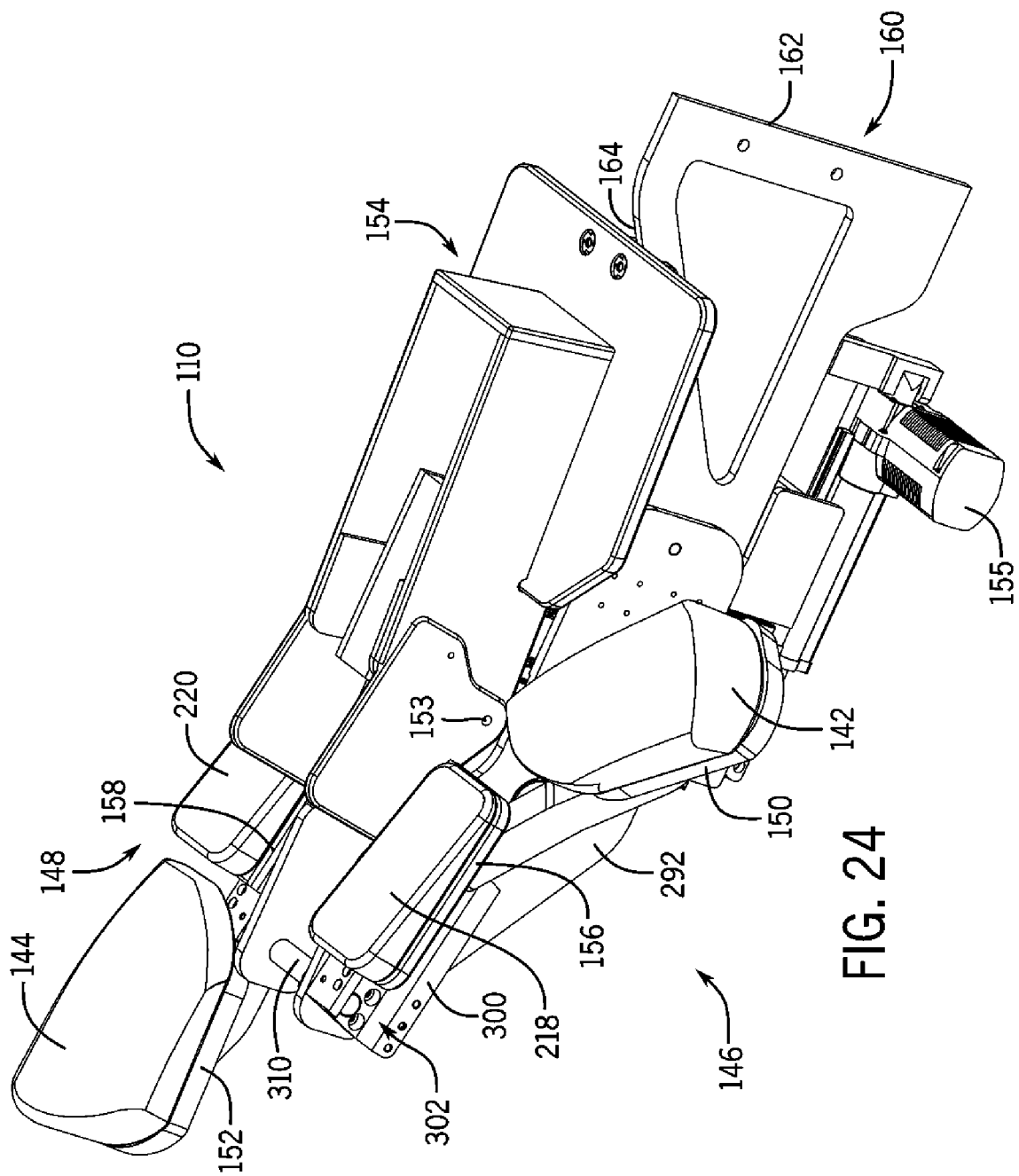
FIG. 24 depicts a perspective view of the lower body support structure with a left upper leg member pivoted about an axle in the left upper leg mounting bracket, in one embodiment.

As seen in FIGS. 23-24, which are, respectively a side view of the lower body support structure 110, and a perspective view of the lower body support structure, the left pelvic support member 150 and attached pad 142 may be rotated about a pin 346 extending vertically through a foot end of the mounting bracket 300. In this way, the left pelvic support member 150 is moved from its original position beneath a left anterior portion of the patient's pelvis so that the left anterior portion of the pelvis is accessible for a surgical procedure. As opposed to being pivotal relative to the mounting bracket 300, the pin 346 may be removed from extending through the bracket 300 and the support member 150 so the support member 150 and pad 142 may be removed from being coupled with the table 100. When needed again, the pelvic support member 150 and pad 142 may be reattached to the table 100 by inserting the pelvic support member 150 back within the slot 302 of the mounting bracket 300 and the pin 346 may be reinserted through the bracket 300 and support member 150. The pelvic support member 150 may be secured in its original position within the slot 302 by a mechanical mechanism such as a friction fit arrangement, magnets, latch, or lock, as described in U.S. Provisional Patent Application No. 62/516,939, filed Jun. 8, 2017, entitled "PRONE AND LATERAL SURGICAL TABLE", which is hereby incorporated by reference in its entirety. While FIGS. 23 and 24 only depict the left pelvic support member 150 rotated about the left mounting bracket 300, the right pelvic support member 152 may be rotated about the right mounting bracket 300 as well.

Figure 34:
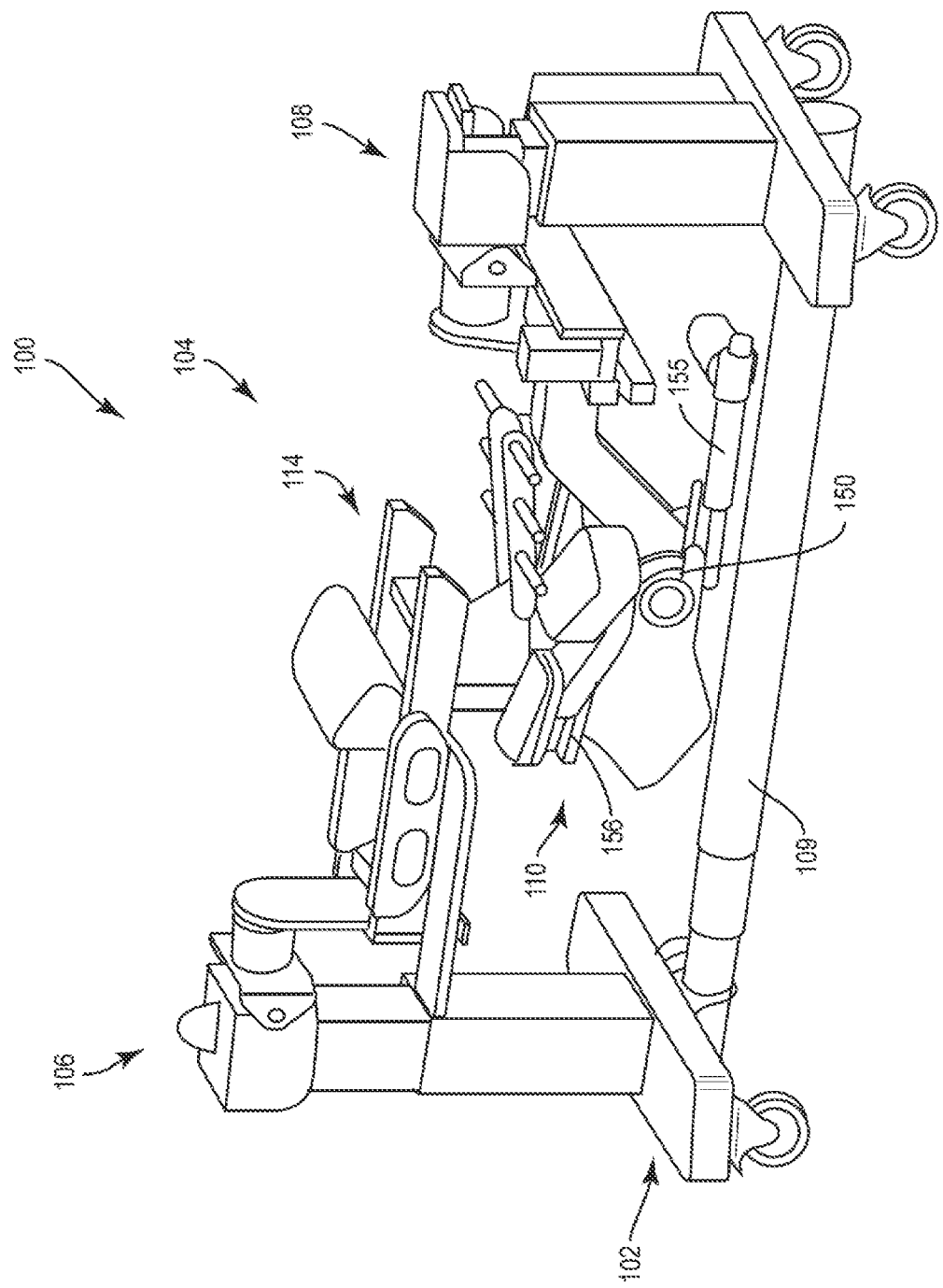
FIG. 34 depicts a perspective view of a surgical table in a stored state, in one embodiment.

In certain instances, as seen in FIG. 34, both the right and left pelvic support members 150, 152 may be rotated about their respective mounting brackets 300 to position their attached pads 140, 142 behind (i.e., towards the foot end of) their respective thigh support members 156, 158.

As seen in the figures, left and right pelvic pads 142, 144, as well as the thigh pads 218, 220, may be removably coupled with the top sides of the pelvic support members 150, 152 of the upper leg members 146, 148. In non-limiting examples, the left and right pelvic pads 142, 144 may be coupled to the pelvic support members 150, 152 via Velcro®, or by a hook and loop fastener. Other attachment mechanisms are possible and contemplated herein. In an embodiment, the left and right pelvic pads 142, 144 may be coupled with the pelvic support members when the patient is in a prone position and he upwardly oriented pelvic pad may be moved away from the patient's pelvis when the patient is rotated in a lateral position. For example, when lateral support board 134 is on the right lateral side member 132 and the patient is rotated laterally on their right side, the left pelvic pad 142 may be removed or moved out of the way to provide the surgeon further access to the patient. In an embodiment, left and right thigh pads may be removably coupled with the top sides of the thigh support members 156, 158 of the upper leg members 146, 148. In non-limiting examples, the left and right thigh pads may be coupled to the thigh support members 156, 158 via Velcro®, or by a hook and loop fastener. Other attachment mechanisms are possible and contemplated herein.

As seen in the figures, the left pelvic support member 150 may match the size of the right pelvic support member 152. In this way, for prone positioning an overall length of the left pelvic support member 150 and left pelvic support pad 142 may be the same size as the right pelvic support member 152 and the right pelvic support pad 144. Alternatively, for example, the right upper leg member 148 of the right lower body support section 138 may be larger than the left upper leg member 146 of the left lower body support section 136. In particular (although not shown in the figures), the right pelvic support member 152, beneath the right pelvic pad 144, on the right lower body support section 138 may be elongated and extend further towards the head end than the left pelvic support member 150 of the left lower body support section 136. The left pelvic support member 150 may be increased in length through the use of an extension member which uses slots and particularly shaped members extending from the extension that fit into the slots. The right pelvic pad 144 may be a single pad or of a multiple pad configuration. In the case of multiple pads, the right pelvic pad 144 may include two or three individual pads that form the pad. The right pelvic pad 144 may, however, be reduced in size to the same size as the left pelvic pad 142 by removing one or two of the other pelvic pads. Thus, the right and left pelvic pads 144, 142 may be the same size, or the right pelvic pad 144 may be larger by the addition of one or two additional pelvic pads to the right pelvic support member 152, wherein the pads can be of different sizes and shapes.

For a prone-only surgical procedure, the right and left pelvic pads 142, 144 may be similarly sized. For a surgical procedure involving lateral positioning, or in addition to prone positioning, the left pelvic pad 142 may be reduced in size to provide more room or space for surgical access to the left lower abdominal region. For instance, in prone positioning, the lower body support structure 110 may function to pivot the patient into flexion and extension in such a way as to eliminate the need for a trunk translator or torso trolley. If the frame had a fixed axis hinge, for example, the patient's torso would need to translate across the head end section of the patient support structure 104 when the head end section articulates relative to a foot end section about the hinge. This may be partly because the biomechanical axes of angulation or rotation for the patient's spinopelvic unit positioned on and above the table hinge is much more complex than what a simple pivot-only hinge can account for. Thus, the surgical table 100 described herein and in the applications incorporated by reference include an lower body support structure 110 that articulates relative to the outer frame 112 in a pre-determined type of arcuate motion that involves pivoting and translating about a fixed axis at or near the head end portion of the pelvic pads 142, 144 so that the patient's torso and intubated head remain stationary during movement involving flexion and extension of the lumbopelvic unit.

For a prone-only surgical procedure using the surgical table 100, among others, the lower body support structure 110 may be positioned such that the patient is in flexion, extension, or a neutral prone position. The outer frame 112 may be as described above and may have one, both, or none of the lateral side members 130, 132 removed. When the table is in a neutral prone position, the patient's legs are lying in the same plane as their upper body and torso. The lower leg support 154 is positioned such that the patient's leg will lie in a straight line. When the patient is in an extended position, the cylinder of the linear actuator is retracted further than when the table is in the neutral position. In the flexed position, the upper leg members 146, 148 are angled such that an end of the lower leg support assembly 154, nearest the patient's hip is lower than an opposite end, nearest the foot. The joint that joins the upper and lower leg members may include a stop feature that locks rotation of the leg members beyond a certain point.

Reference is now made to FIGS. 26-33, which show an embodiment of the surgical table 100 situated in various exemplary positions for a surgical procedure. FIG. 34 shows the surgical table 100 in a stored configuration with the right and left lateral support members 130, 132 removed from the patient support structure 104. The telescoping rail 109 of the base 102 is retracted such that the end support structures 106, 108 are moved closer to each other than when the lateral support members 130, 132 are coupled to the end support structures 106, 108. The end support structures 106, 108 are elevated to different heights relative to each other so that a portion of the central support structure 160 is positioned underneath the upper body support members 120, 122 of the upper body support structure 114.

The following description describes methods of performing a spinal surgery. Alternatively, the following description may describe a method of using the surgical table in a surgical procedure. In particular, the steps may include: positioning the patient in a prone position on a patient support structure 104 comprising a chest pad 140 and a pair of pelvic pads 142, 144 comprising a first pad 142 and a second pad 144, the first pad 142 configured to support a first side of the pelvis, the second pad 144 configured to support a second side of the pelvis; rolling the patient into a lateral decubitus position such that the pair of pelvic pads 142, 144 are vertically aligned such that the first pad 142 of the pair of pelvic pads 142, 144 is oriented above the second pad 144 of the pair of pelvic pads; moving the first pad 142 away from the first side of the pelvis of the patient; and delivering an implant into the spine of the patient with the patient in the lateral decubitus position.

Figure 26:
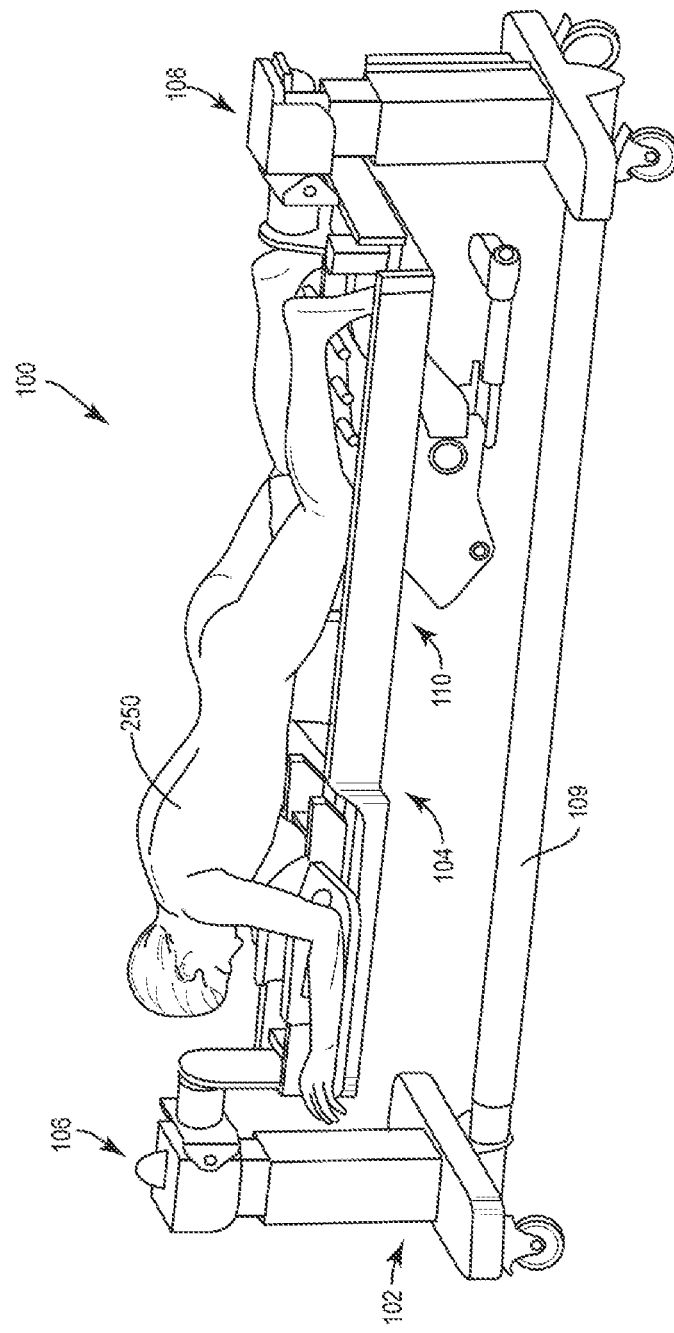
FIG. 26 depicts a perspective view of a surgical table with a patient positioned prone, in one embodiment.

As seen in FIG. 26, which is an isometric view of the surgical table 100 with the patient support structure 104 in a neutral position, a patient 250 is brought to the operating room on a gurney (not shown) and is rolled into a prone position on the patient support structure 104. The patient 250 is positioned by the surgeon and/or the surgical staff into a neutral position, as shown in the figure.

Figure 27:
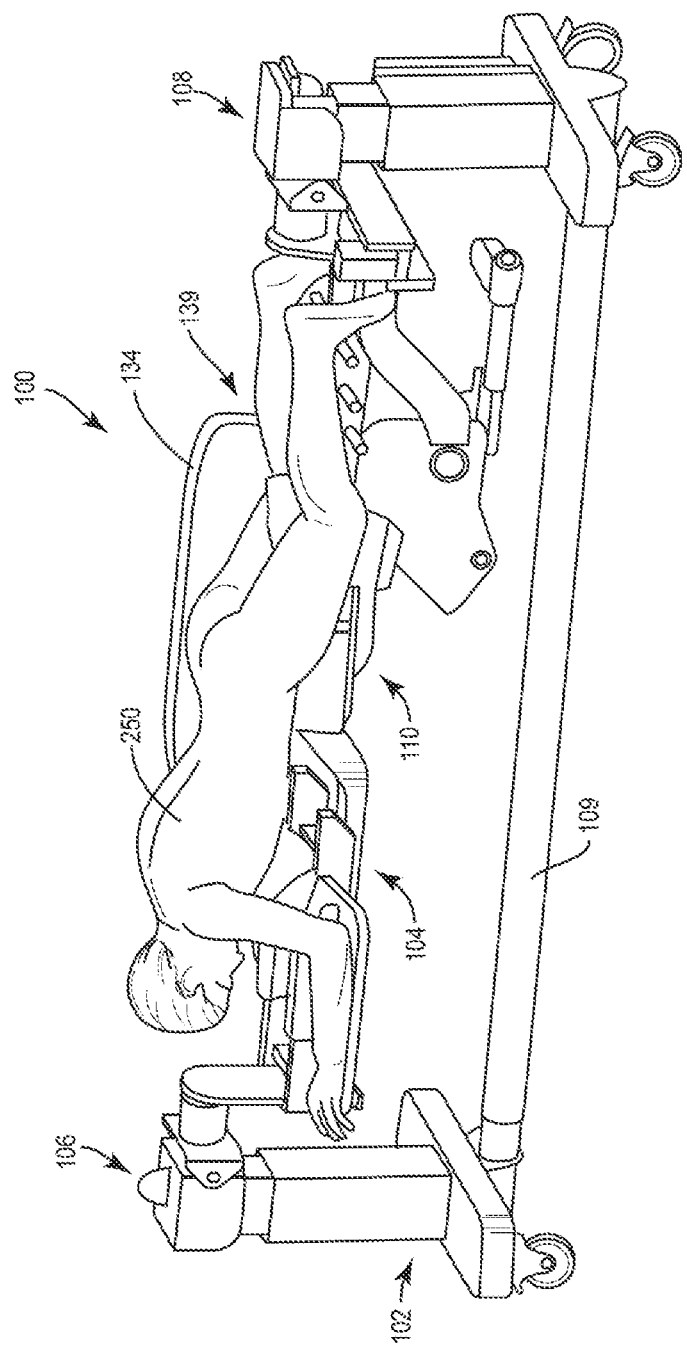
FIG. 27 depicts a perspective view of a surgical table with a lateral support board attached thereto with a patient positioned prone, in one embodiment.

Depending on the surgical procedure and the desired access point to the surgical site, one of the lateral side members are removed and lateral support board is positioned on the remaining lateral side member, as seen in FIG. 27. In the particular exemplary procedure, the left lateral side member 130 is removed and the lateral support board 134 is coupled to the right lateral side member 132.

Figure 28:
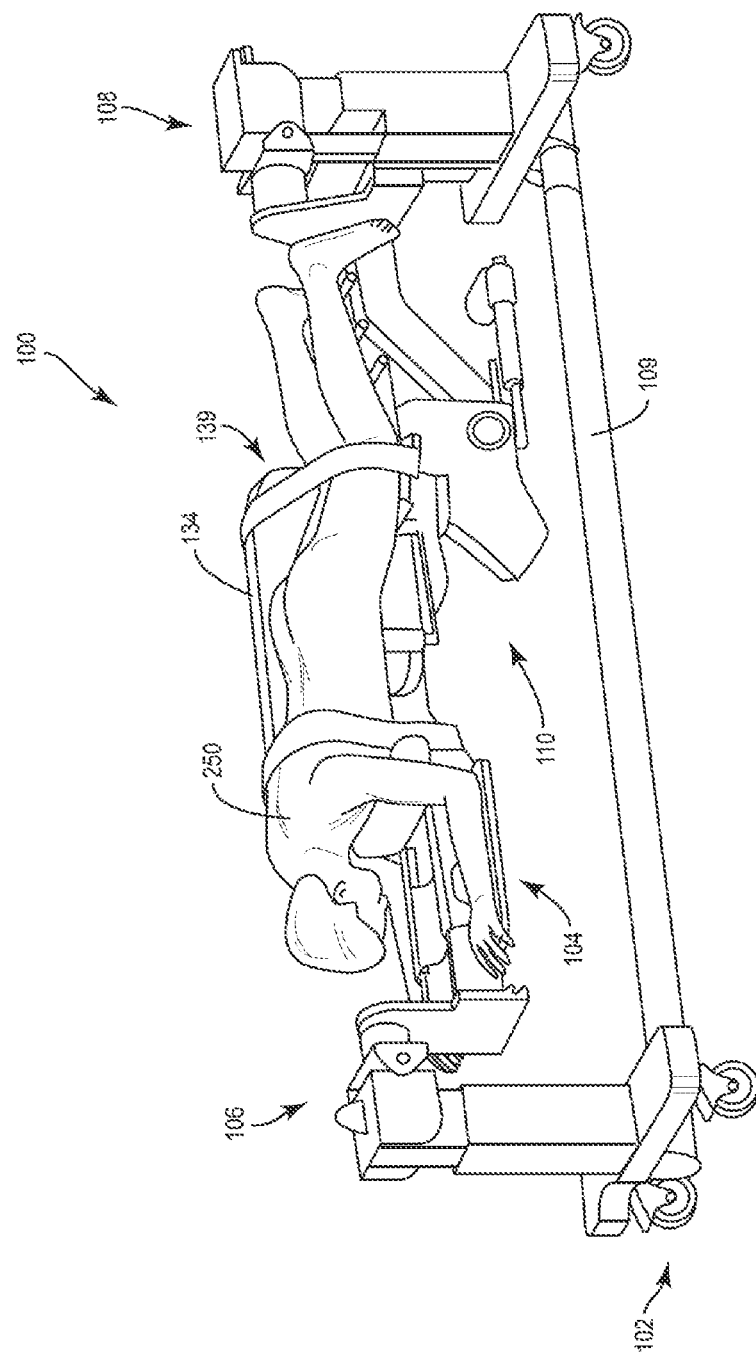
FIG. 28 depicts a perspective view of a surgical table with a lateral support board attached thereto with a patient positioned prone and with straps around the patient and table, in one embodiment.

The patient 250 is then secured to the patient support structure 104 via straps that are fitted around the patient 250 and the patient support structure 104, as seen in FIG. 28. In certain instances, the straps may be positioned around the knee region and, more specifically, around the thigh support members 156, 158 and the lateral support board 134. Additionally, one or more straps may be positioned around the torso region, and more specifically, around the upper body support members 120, 122 and the lateral support board 134.

Figure 29:
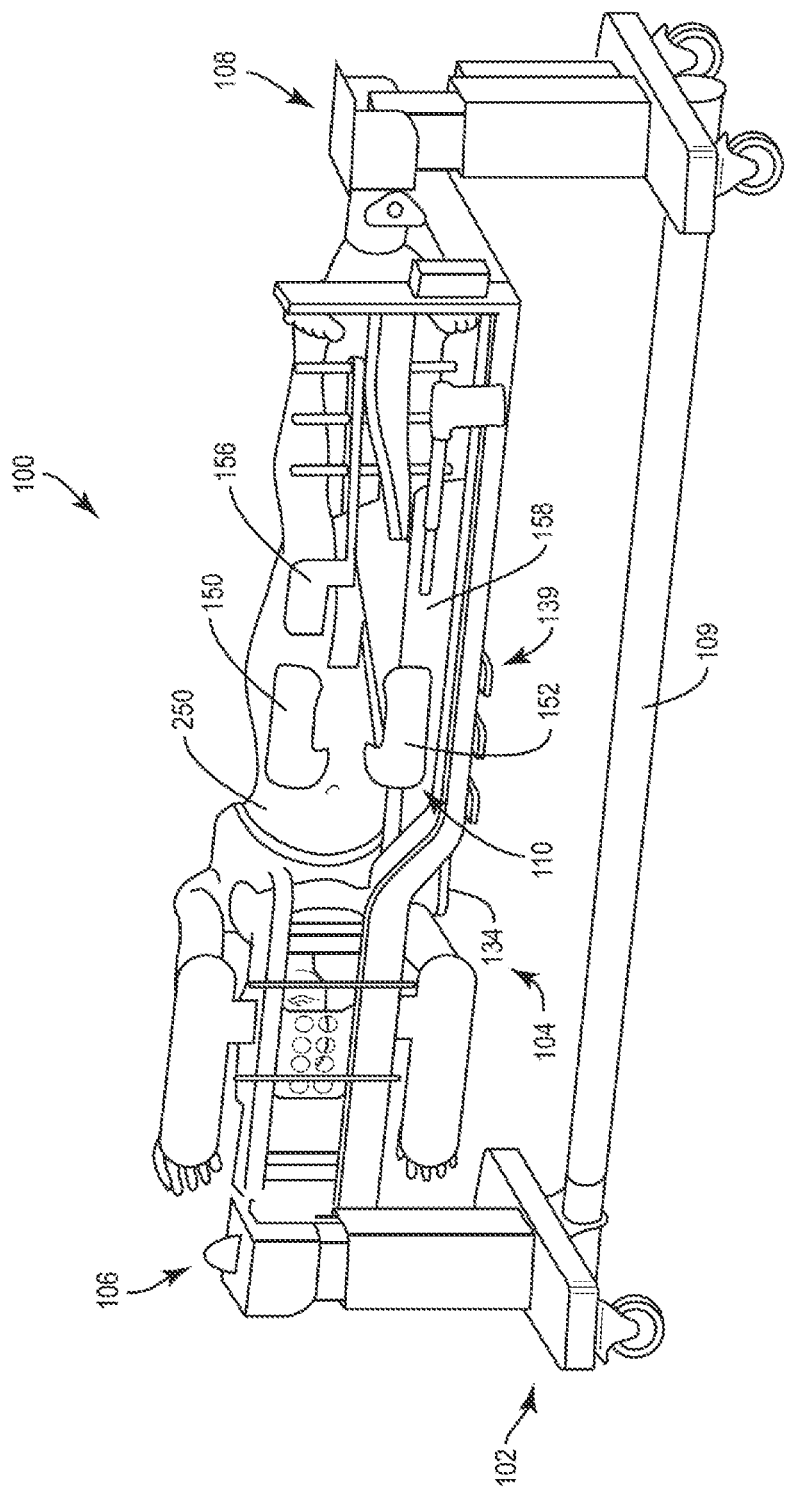
FIG. 29 depicts a perspective view of a surgical table with a patient positioned in a lateral position, where the table is rolled about ninety degrees, in one embodiment.

Next, as seen in FIG. 29, the patient support structure 104, including the patient 250, may be rolled or tilted about ninety degrees such that the lateral support board 134 is at the bottom or lowest point of the patient support structure 104 and the patient 250 is in a lateral decubitus position.

Figure 30:
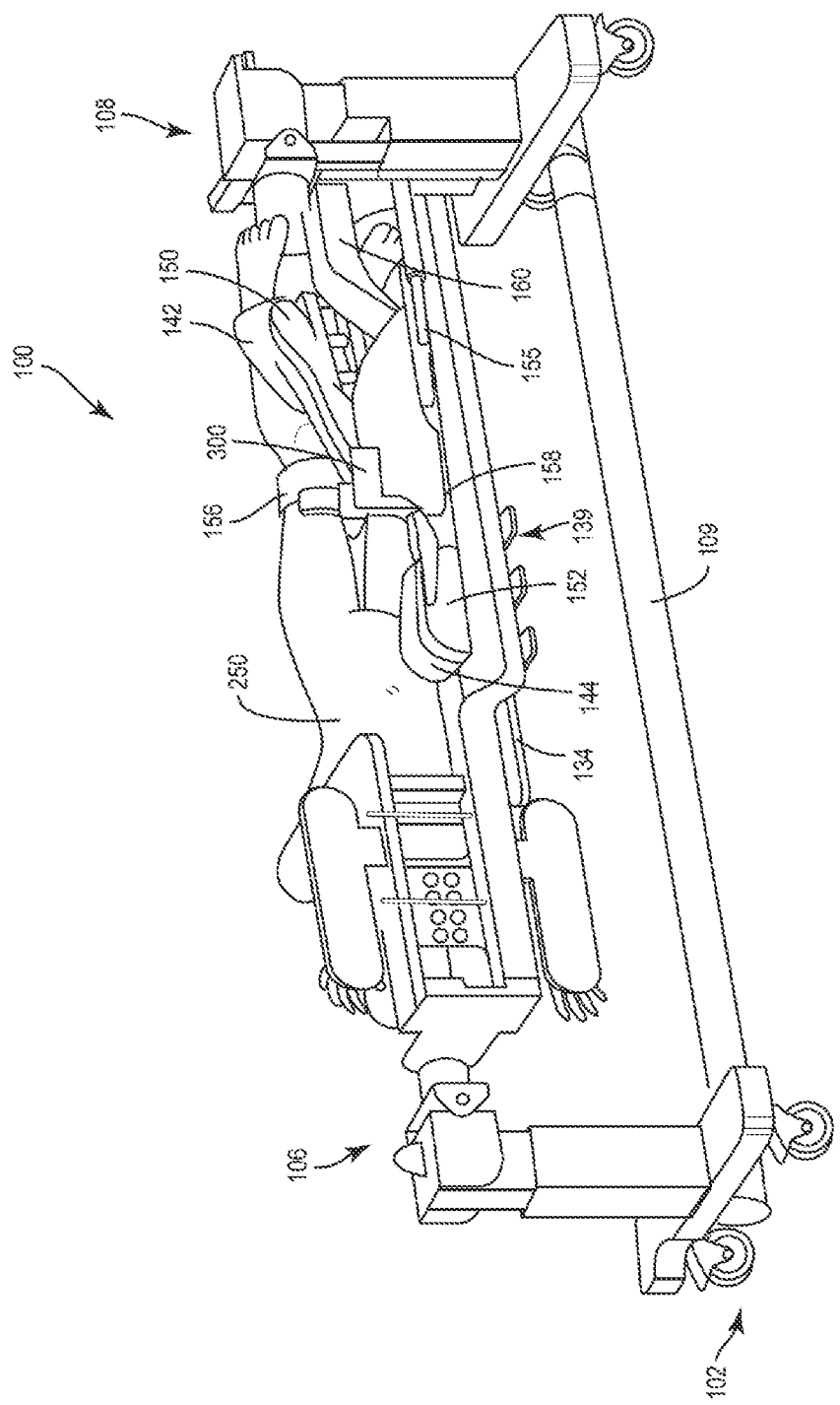
FIG. 30 depicts another perspective view of a surgical table with a patient positioned in a lateral position, where the table is rolled about ninety degrees and the left upper leg member is pivoted about the left upper leg mounting bracket, in one embodiment.
Figure 31:
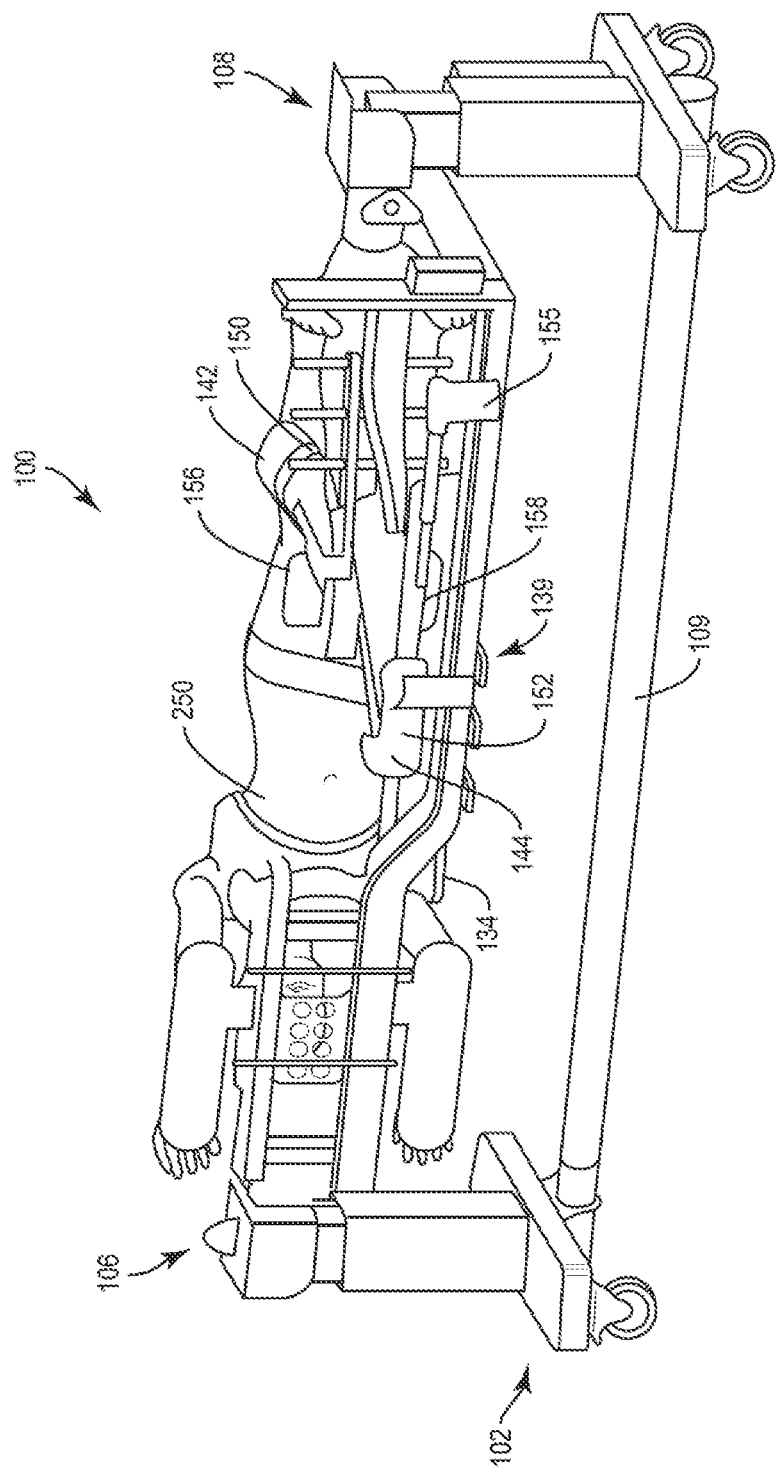
FIG. 31 depicts another perspective view of a surgical table with a patient positioned in a lateral position, where the table is rolled about ninety degrees, and where an incision is made into the patient's left anterior abdomen region, in one embodiment.
Figure 32:
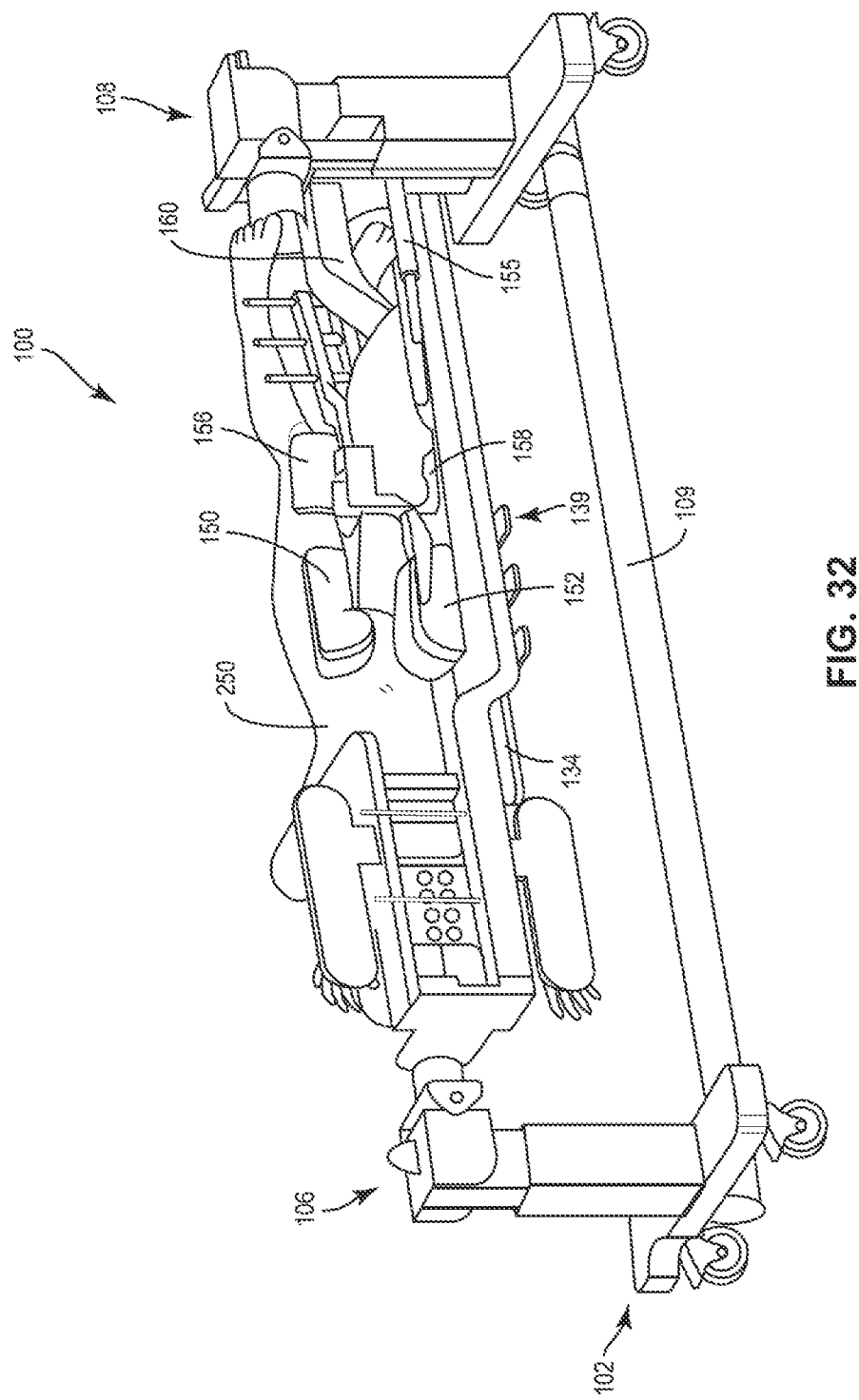
FIG. 32 depicts another perspective view of a surgical table with a patient positioned in a lateral position, where the table is rolled about ninety degrees, the incision is closed, and the left upper leg member is rotated back into its original position over the patient's left anterior pelvis, in one embodiment.
Figure 33:
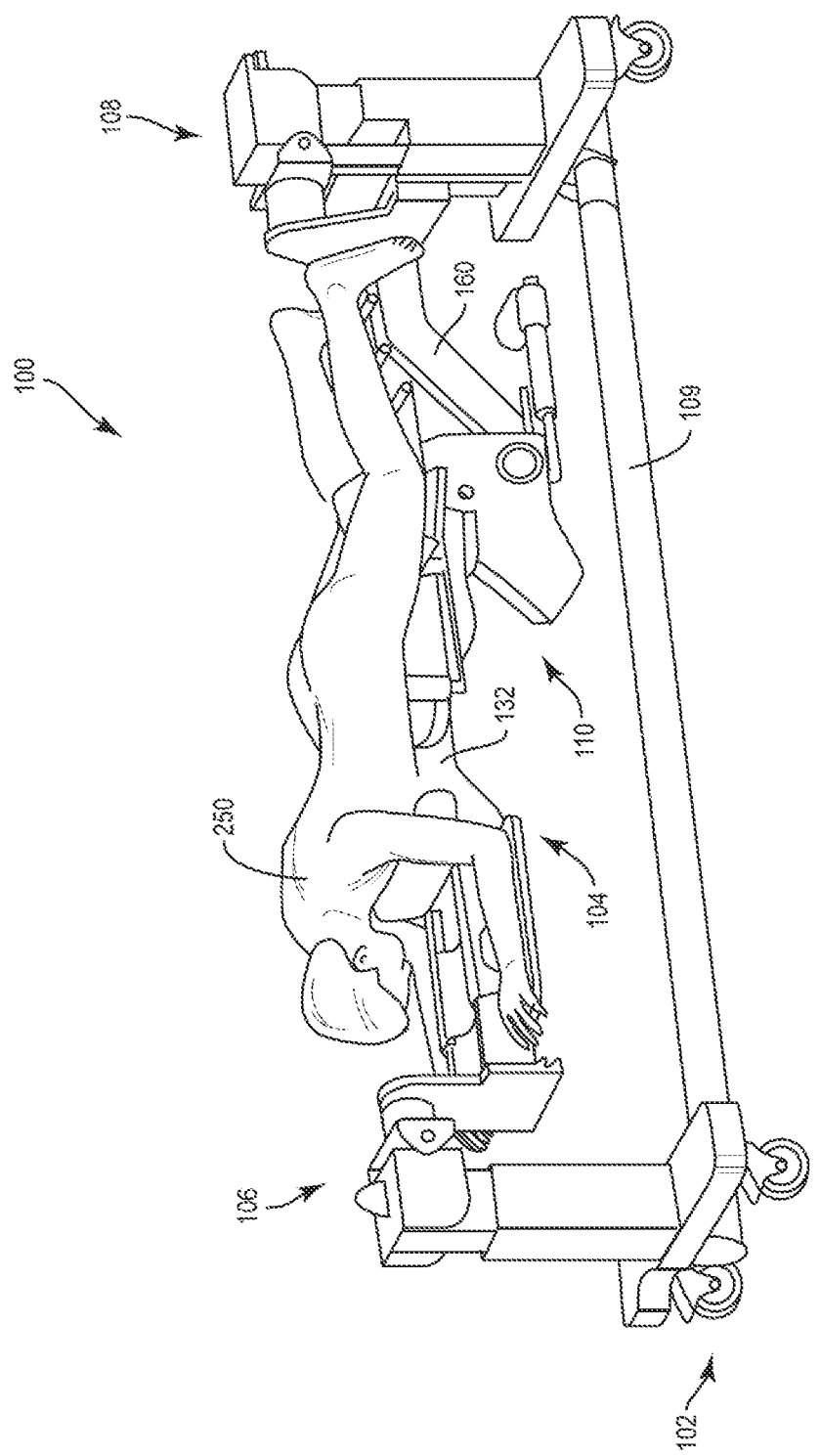
FIG. 33 depicts a perspective view of a surgical table with a patient positioned thereon, and where the patient is rolled to a prone position from a lateral position, in one embodiment.

Once the patient 250 is in the lateral decubitus position, the left pelvic support member 150 on the open side of the patient support structure 104 may be pivoted within the left lateral slot 172 and pivoted laterally about a joint that couples the upper leg member 146 and the U-shaped carriage 168, as seen in FIG. 30. The left pelvic support member 150 may be pivoted out of the way of the surgical site and an additional strap may be positioned on the patient 250 around the gluteus maximus area. The surgeon may then make an incision in the patient 250, as seen by the incision line (dotted line) in FIG. 31. The surgery may continue with the patient in this orientation. And upon closing the incision, the gluteus maximus strap may be removed and the left pelvic support member 150 may be pivoted or rotated back into position to abut the patient's left hip region, as seen in FIG. 32. The patient support structure 104 may then be rotated or tilted back to the neutral position and the lateral support board 134 may be removed from the right lateral side member 132, as seen in FIG. 33.

Also provided herein is a method of positioning a patient on the patient support structure 104 of the surgical table 100. The method may further include inserting a spinal implant into the patient's spine once the patient is properly positioned on the surgical table 100. The patient may be positioned prone on the patient support structure 104 and the patient's arms may be stabilized on a pair of arm supports. The patient may then be rolled into a lateral decubitus position so that one pelvic pad is oriented upwardly over the other pelvic pad. The upwardly oriented pelvic pad may then be moved away from the patient's pelvis. After at least the patient's flank is sterilely prepped and draped, the surgeon may make an incision therein so as to proceed to insert the implant into the patient's spine. The surgeon may then close the incision and move the pelvic pad back into position with respect to the patient's pelvis after a sterile cover is placed over the pelvic pad. The patient may be rolled back into a prone position. In some embodiments, at least one of the lateral side members may be removed from the patient support structure before or after the patient is positioned on the table.

In certain instances, a particular surgical procedure may require the patient 250 to be in a flexed or extended position. The patient 250 may be positioned in a flexed position with the head with the head end support structure 106 positioned lower than the foot end support structure 108. It is noted that the roll axes may be maintained in parallel or coaxial alignment in such a position. When the patient 250 is in an extended position, the head end support structure 106 may be positioned higher than the foot end support structure 108. In the extended position, the roll axes may be coaxially aligned as well.

In a collapsed or stored state, as seen in FIG. 34, the right and left lateral side members 130, 132 are removed, the head end support structure 106 is an extended position, the foot end support structure 108 is in a retracted position, the foot and head end support structures 106, 108 are moved nearer each other via collapsing of the telescoping cylinder or rail 109 of the base 102 that connects the end support structures 106, 108, and the right and left pelvic support members 150, 152 are pivoted laterally outward. The surgical table 100 may be stored or transported in this orientation. The surgical table 100 may be moved or rolled on the wheels 111 of the base 102.

Figure 35:
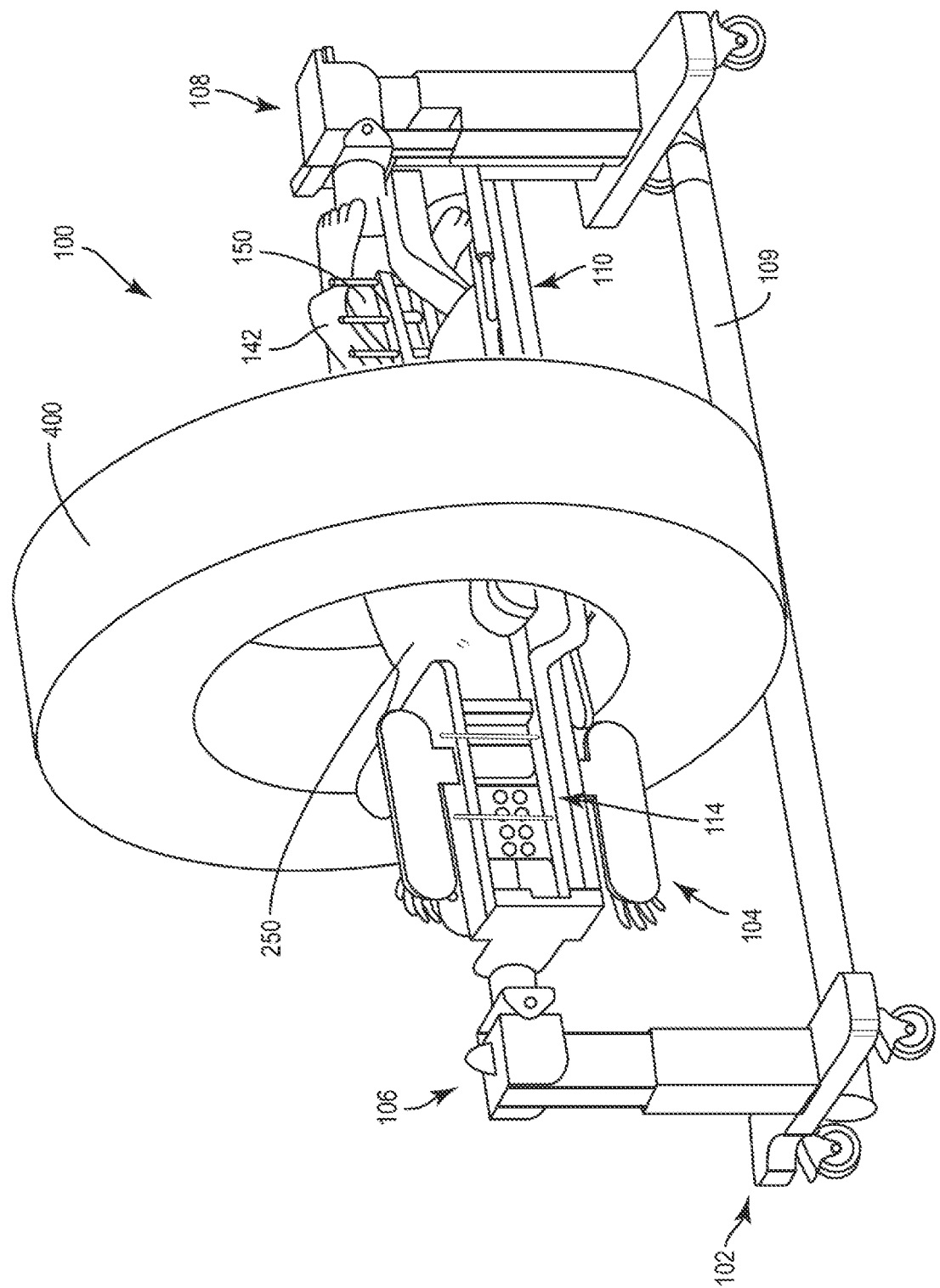
FIG. 35 depicts a perspective view of a surgical table with a patient positioned in a lateral decubitus position, where the table and patient are within an opening of an imaging machine, in one embodiment.

As seen in FIG. 35, the surgical table 100 may be used in conjunction with an imaging system. For example, the patient 250 may be positioned in lateral decubitus with the patient support structure 104 rotated about ninety degrees and a donut of an O-arm imaging system 400 positioned around the patient and patient support structure 104 for intra-operative imaging. In an embodiment, the head and foot end support structure may be raised or extended to accommodate the O-arm imaging system.

Figure 38:
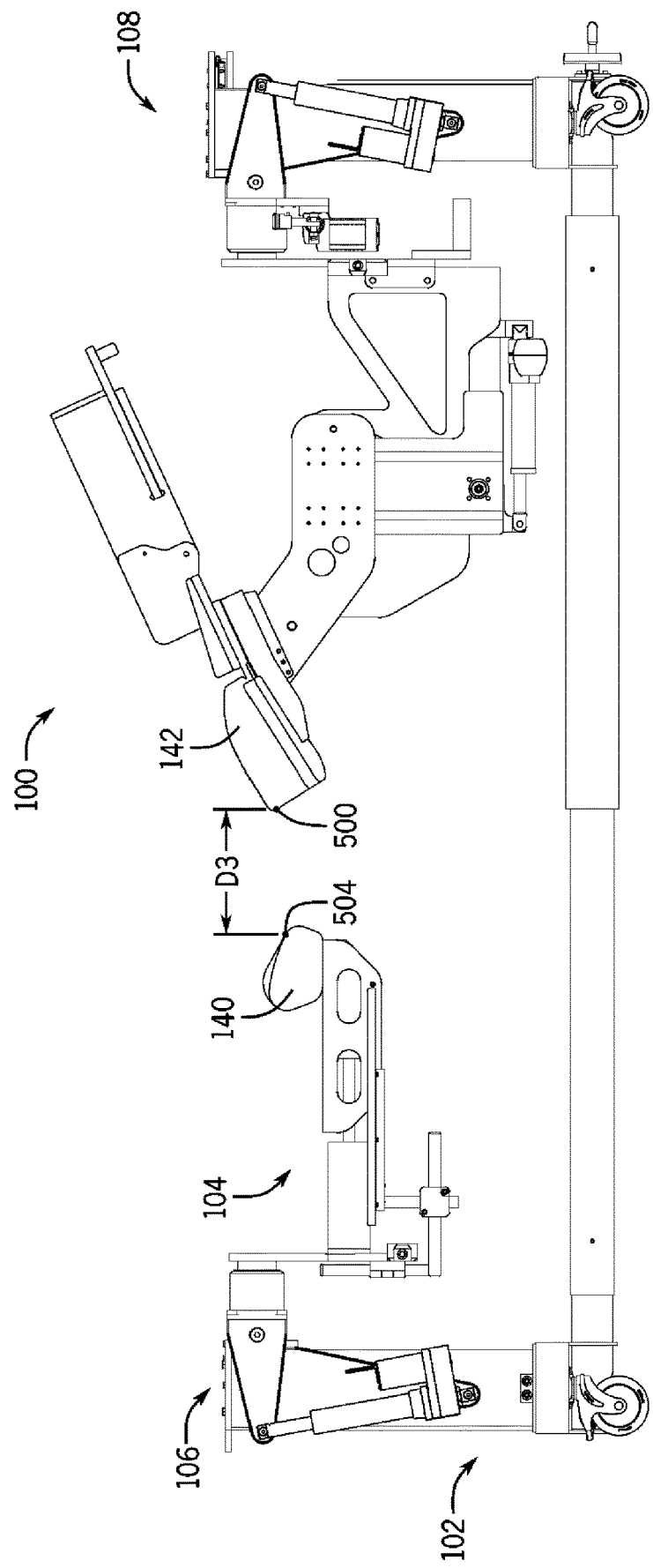
FIG. 38 depicts a side view of a surgical table with a patient support structure in an extended position.

FIGS. 36-38 depict, respectively, side views of a surgical table 100 with the patient support structure 104 in a neutral position, a flexed position, and an extended position. As seen in the figures, the pelvic pads 144, 142 rotate about a virtual pivot axis 500 defined by a pair of virtual pivot points on each of the pelvic pads 144, 142. While the pelvic pads 144, 142 may rotate about a mechanical pivot axis 502 defined as an axis extending through the second shaft 310, the virtual pivot axis of the pelvic pads 144, 142 encompasses the vertical and horizontal translation, as well as the rotation of the pelvic pads 144, 142 about the mechanical pivot axis 502. Stated differently, the pelvic pads 144, 142 may rotate about the mechanical pivot axis 502, but when rotation of the pelvic pads 144, 142 is combined with vertical and horizontal translation, the combined effect of the rotation, horizontal translation, and vertical translation of the pelvic pads 144, 142 results in the pelvic pads 144, 142 rotating about a virtual pivot axis 500 that is positioned near the distal end of the pelvic pads 144, 142.

As seen in FIG. 36, which shows the patient support structure 104 in a neutral position, a proximal point 504 on the chest pad 140 is spaced apart from a point extending through the virtual pivot axis 500 a distance of D1. As seen in FIG. 37, which shows the patient support structure 104 in a flexed position, the proximal point 504 on the chest pad 140 is spaced apart from a point extending through the virtual pivot axis 500 a distance D2. In certain instances, distance D2 is less than distance D1. In certain instances, the difference between distances D2 and D1 may be about 1.75 inches in a horizontal direction. Stated differently, when the patient support structure 104 moves from a neutral position to a flexed position, the virtual pivot axis 500 moves horizontally towards a point on the chest pad 140 (or any other fixed point connected to the head end support structure 106) about 1.75 inches. As seen by a comparison of FIGS. 36 and 37, the virtual pivot axis 500 moves closer to the proximal point 504 on the chest pad 140 in a horizontal direction, but either does not move at all or does not move a substantial distance in the vertical direction when the patient support structure 104 transitions from the neutral position to the flexed position. In certain instances, the pelvic pads 144, 142 may rotate about 35 degrees about the virtual pivot axis 500 when the patient support structure 104 transitions from the neutral position to the flexed position, as seen in FIG. 37. In certain instances, for every 10 degrees of angulation of the pelvic pads 144, 142 about the mechanical pivot axis 502, the virtual pivot axis 500 translates horizontally about 0.5 inch.

Referring to FIG. 38, which depicts the patient support structure 104 in an extended position, a proximal point 504 on the chest pad 140 is spaced apart from a point extending through the virtual pivot axis 500 a distance of D3. In certain instances, distance D3 is greater than distance D1. In certain instances, distance D3 is greater than distance D2. In certain instances, the difference between distances D3 and D1 may be about 1.25 inches in a horizontal direction. In certain instances, the difference between distances D3 and D2 may be about 3 inches in a horizontal direction. That is, a total amount of horizontal translation of the pelvic pads 144, 142 when moving between extended, neutral, and flexed positions may be about 3 inches, where the pelvic pads 144, 142 move about 1.75 inches in a first horizontal direction from a neutral position, and where the pelvic pads 144, 142 move about 1.25 inches in a second horizontal direction (opposite the first direction) from the neutral position. In certain instances, the first horizontal direction may be towards the chest pad 140 when moving from the neutral position to the flexed position. In certain instances, the second horizontal direction may be away from the chest pad 140 when moving from the neutral position to the extended position.

It is noted that the "horizontal direction" may mean parallel or generally parallel with the rail 109 or with a roll axis extending through the shafts 121 of the roll assemblies 127, 125. The "vertical direction" may mean perpendicular to the horizontal direction or perpendicular with a plane defined by the floor. It is foreseen that while certain dimensions are described herein, but other dimensions may be possible and contemplated within the scope of the present disclosure.

Stated differently, when the patient support structure 104 moves from a neutral position to a flexed position, the virtual pivot axis 500 moves horizontally away from a point on the chest pad 140 (or any other fixed point connected to the head end support structure 106) about 1.25 inches. As seen by a comparison of FIGS. 36 and 38, the virtual pivot axis 500 moves away from to the proximal point 504 on the chest pad 140 in a horizontal direction, but either does not move at all or does not move a substantial distance in the vertical direction when the patient support structure 104 transitions from the neutral position to the extended position. In certain instances, the pelvic pads 144, 142 may rotate about 25 degrees about the virtual pivot axis 500 when the patient support structure 104 transitions from the neutral position to the extended position, as seen in FIG. 38. In certain instances, for every 10 degrees of angulation of the pelvic pads 144, 142 about the mechanical pivot axis 502, the virtual pivot axis 500 translates horizontally about 0.5 inch.

Although various representative embodiments of the present disclosure have been described above with a certain degree of particularity, those skilled in the art could make numerous alterations to the disclosed embodiments without departing from the spirit or scope of the inventive subject matter set forth in the specification. All directional references (e.g., top, bottom, front, back, proximal, distal, upper, lower) are only used for identification purposes to aid the reader's understanding of the embodiments of the present disclosure, and do not create limitations, particularly as to the position, orientation, or use of the disclosure unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed or articulate relation to each other.

It is intended that all matter contained in the above description or shown in the accompanying drawings shall be interpreted as illustrative only and not limiting. Changes in detail or structure may be made without departing from the spirit of the disclosure and as defined in the appended claims. For example, different sliding hinge mechanisms and configurations can be used to move the patient, wherein a distance between the chest pad or pads and the head end portion of the pelvic pad or pads remains substantially consistent during flexion and extension, as described herein.

What is claimed is:

1. A surgical table for prone and lateral positioning of a patient, the table comprising:
 a base supported on the floor and comprising a head end support structure, a foot end support structure opposite the head end support structure, a rail connecting the head and foot end support structures, and a longitudinal axis extending between the head and foot end support structures; and
 a patient support structure comprising an upper body support structure supported off of the head end support structure at a first end and a lower body support structure supported off of the foot end support structure at a second end, the upper body support structure comprising a chest pad, the lower body support structure comprising a lower body translation and rotation structure and at least one pelvic pad supported thereon, the at least one pelvic pad rotationally coupled with the lower body translation and rotation structure via a mechanism configured to rotate about a rotation axis that is generally perpendicular to the longitudinal axis, wherein, when the patient support structure changes from a neutral position to a flexed position, the lower body translation and rotation structure is configured to translate the at least one pelvic pad towards the chest pad, and rotate the at least one pelvic pad about the rotation axis,
 wherein the lower body translation and rotation structure is slidably supported on a central support structure that is coupled to the foot end support structure, and
 wherein the lower body translation and rotation structure comprises an inner translation structure and an outer translation structure, the inner translation structure slidably coupled with the central support structure, the outer translation structure slidably coupled with the inner translation structure, the inner and outer translation structures configured to facilitate horizontal and vertical translation of the at least one pelvic pad supported thereon relative to the central support structure.

2. The surgical table of claim 1, wherein the lower body support structure further comprises an actuator configured to cause the lower body translation and rotation structure to translate and rotate the at least one pelvic pad via actuation of the actuator.

3. The surgical table of claim 1, wherein the upper body support structure comprises a third end opposite the first end, the lower body support structure comprising a fourth end opposite the second end, the third and fourth ends define a gap therebetween.

4. The surgical table of claim 1, wherein a combined rotation and translation of the at least one pelvic pad defines the rotation axis about which the at least one pelvic pad is configured to rotate, the rotation axis being configured to maintain a substantially constant height when the patient support structure changes from a neutral position to a flexed position.

5. The surgical table of claim 4, wherein the rotation axis extends transverse through a distal portion of the at least one pelvic pad.

6. The surgical table of claim 1, further comprising a pair of non-hinged outer frame members supported at a head end by the head end support structure and supported at a foot end by the foot end support structure, the pair of non-hinged outer frame members comprising a right lateral side member and a left lateral side member.

7. The surgical table of claim 1, wherein, when the patient support structure changes from the neutral position to an extended position, the lower body translation and rotation structure is configured to translate the at least one pelvic pad away from the chest pad, and rotate the at least one pelvic pad about the rotation axis.

8. A surgical table for prone and lateral positioning of a patient, the table comprising:
 a base supported on the floor and comprising a head end support structure, a foot end support structure opposite the head end support structure, and a rail connecting the head and foot end support structures; and
 a patient support structure comprising an upper body support structure supported off of the head end support structure at a first end, and a lower body support structure supported off of the foot end support structure at a second end, the lower body support structure comprising a right and left lower body support sections and a central support structure, each of the right and left lower body support sections comprising a pelvic support member supporting a pelvic pad, a thigh support member, and a lower leg support assembly, the central support structure coupled to the foot end support structure, the right and left lower body support sections coupled to the central support structure and configured to move relative to the central support structure when moving the patient between flexed and extended positions, wherein the lower body support structure comprises an inner translation structure slidingly coupled to the central support structure and an outer translation structure slidingly coupled to the inner translation structure, wherein the inner and outer translation structures are configured to facilitate vertical and horizontal translation of the right and left lower body support sections relative to the central support structure.

9. The surgical table of claim 8, wherein the patient support structure further comprises a pair of non-hinged outer frame members supported at a head end by the head end support structure and supported at a foot end by the foot end support structure, the pair of non-hinged outer frame members comprising a right lateral side member and a left lateral side member.

10. The surgical table of claim 8, wherein the pelvic support member of the left lower body support section is pivotally coupled with a portion of the left lower body support section so as to pivot laterally outward from the portion of the left lower body support section to provide access to a left anterior portion of the patient.

11. The surgical table of claim 8, wherein the pelvic support member of the right lower body support section is pivotally coupled with a portion of the right lower body support section so as to pivot laterally outward from the portion of the right lower body support section to provide access to a right anterior portion of the patient.

* * * * *